(12) United States Patent
Hua et al.

(10) Patent No.: US 9,879,245 B2
(45) Date of Patent: Jan. 30, 2018

(54) POLYPEPTIDES HAVING BETA-MANNANASE ACTIVITY AND METHODS OF USE

(71) Applicant: Danisco US Inc., Palo Alto, CA (US)

(72) Inventors: Ling Hua, Hockessin, DE (US); Rosalyn Lau, Hayward, CA (US); Steven Le, Palo Alto, CA (US); Zhen Qian, Shanghai (CN); Zheyong Yu, Shanghai (CN)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 14/648,677

(22) PCT Filed: Dec. 2, 2013

(86) PCT No.: PCT/US2013/072589
§ 371 (c)(1),
(2) Date: May 29, 2015

(87) PCT Pub. No.: WO2014/088940
PCT Pub. Date: Jun. 12, 2014

(65) Prior Publication Data
US 2016/0115465 A1 Apr. 28, 2016

(30) Foreign Application Priority Data

Dec. 7, 2012 (WO) ................ PCT/CN2012/086181

(51) Int. Cl.
| | | |
|---|---|---|
| C12N 1/21 | (2006.01) |
| C12N 1/15 | (2006.01) |
| C12N 1/19 | (2006.01) |
| C12N 9/26 | (2006.01) |
| C12N 9/24 | (2006.01) |
| C12P 19/02 | (2006.01) |
| C12P 19/14 | (2006.01) |

(52) U.S. Cl.
CPC ......... *C12N 9/2494* (2013.01); *C12N 9/2491* (2013.01); *C12P 19/02* (2013.01); *C12P 19/14* (2013.01); *C12Y 302/01025* (2013.01); *C12Y 302/01078* (2013.01)

(58) Field of Classification Search
None
See application file for complete search history.

(56) References Cited

U.S. PATENT DOCUMENTS

| | | | |
|---|---|---|---|
| 296,935 A | 4/1884 | Dahl | |
| 4,816,567 A | 3/1989 | Cabilly et al. | |
| 5,010,182 A | 4/1991 | Brake et al. | |
| 5,364,934 A | 11/1994 | Drayna et al. | |
| 5,536,325 A | 7/1996 | Brink | |
| 5,705,369 A | 1/1998 | Torget et al. | |
| 6,409,841 B1 | 6/2002 | Lombard | |
| 6,423,145 B1 | 7/2002 | Nguyen et al. | |
| 6,566,114 B1 * | 5/2003 | Kauppinen .... | C12Y 302/01078 435/183 |
| 6,660,506 B2 | 12/2003 | Nguyen et al. | |
| 6,984,406 B2 | 1/2006 | Cho et al. | |
| 7,045,331 B2 | 5/2006 | Dunn-Coleman et al. | |
| 7,183,093 B2 | 2/2007 | Kauppinen et al. | |
| 8,101,393 B2 | 1/2012 | Gray et al. | |
| 8,679,824 B2 | 3/2014 | Huang et al. | |
| 8,802,388 B2 | 8/2014 | Jones et al. | |
| 8,986,970 B2 | 3/2015 | Jones et al. | |
| 9,040,278 B2 | 5/2015 | Cascao-Pereira et al. | |
| 9,238,806 B2 | 1/2016 | Hill et al. | |
| 9,447,400 B2 | 9/2016 | Bott et al. | |
| 2003/0203466 A1 | 10/2003 | Kauppinen | |
| 2005/0084934 A1 | 4/2005 | Takakura | |
| 2007/0031918 A1 | 2/2007 | Dunson et al. | |
| 2011/0294166 A1 | 12/2011 | Han et al. | |
| 2013/0143277 A1 | 6/2013 | Guitierrez et al. | |
| 2013/0177947 A1 | 7/2013 | Bower et al. | |
| 2013/0337508 A1 | 12/2013 | Fujdala et al. | |
| 2014/0073017 A1 | 3/2014 | Kaper et al. | |
| 2014/0106408 A1 | 4/2014 | Mitchinson et al. | |
| 2014/0134677 A1 | 5/2014 | Mitchinson et al. | |
| 2015/0252343 A1 | 9/2015 | Bower et al. | |
| 2016/0060665 A1 | 3/2016 | Power et al. | |

FOREIGN PATENT DOCUMENTS

| | | | | |
|---|---|---|---|---|
| BE | WO 9909126 A1 * | 2/1999 | ........... | C11D 3/0036 |
| EP | 36776 A2 | 9/1981 | | |
| EP | 362179 A2 | 4/1990 | | |
| EP | 73657 B1 | 12/1990 | | |
| EP | 238023 B1 | 12/1993 | | |
| WO | WO 89/05859 A1 | 6/1989 | | |
| WO | WO 90/13646 A1 | 11/1990 | | |

(Continued)

OTHER PUBLICATIONS

Sang, H. Mechanisms of Development 121:1179-1186, 2004.*
Altschul, et al., "Basic local alignment search tool," Journal of Molecular Biology, 1990, vol. 215, pp. 403-410.
Altschul, et al., "Local alignment statistics," Methods in Enzymology, 1993, vol. 266, pp. 460-480.
Araujo, et al., "Hemicellulases of *bacillus* species: preliminary comparative studies on production and properties of mannanases and galactanases," Journal of Applied Bacteriology, 1990, vol. 68, pp. 253-261.
Aro, et al., "ACEII, a Novel Transcriptional Activator Involved in Regulation of Cellulase and Xylanase Genes of Trichoderma reesei*," The Journal of Biological Chemistry, 2001, vol. 276, pp. 24309-24314.

(Continued)

*Primary Examiner* — David Steadman

(57) ABSTRACT

The present compositions and methods relate to a beta-mannanase from *Bacillus hemicellulosilyticus*, polynucleotides encoding the beta-mannanase, and methods of make and/or use thereof. Formulations containing the beta-mannanase are suitable for use in hydrolyzing lignocellulosic biomass substrates, especially those comprising a measurable level of galactoglucomannan (GGM) and/or glucomannan (GM).

11 Claims, 14 Drawing Sheets

(56) References Cited

FOREIGN PATENT DOCUMENTS

| | | | |
|---|---|---|---|
| WO | WO 2004/033646 A2 | 4/2004 | |
| WO | WO 2004/081185 A2 | 9/2004 | |
| WO | WO 2005/001036 A2 | 1/2005 | |
| WO | WO 2005/069762 A2 | 8/2005 | |
| WO | WO 2006/110901 A3 | 10/2006 | |
| WO | WO 2009009142 A2 | 1/2009 | |
| WO | WO 2010/141779 A1 | 12/2010 | |
| WO | WO 2011038019 A2 * | 3/2011 | ............ C12N 9/2402 |
| WO | WO 2011/091260 A2 | 7/2011 | |
| WO | WO 2014/088934 | 6/2014 | |
| WO | WO 2014/088935 | 6/2014 | |
| WO | WO 2014/088937 | 6/2014 | |

OTHER PUBLICATIONS

Bennett & Lasure, "More gene manipulations in fungi," Academic Press, 1991, pp. 70-76.

Bewley, "Molecular cloning of a cDNA encoding a (1-4)-β-mannan endohydrolase from the seeds of germinated tomato (*Lycopersicon esculentum*)," Planta, 1997, vol. 203, pp. 454-459.

Carter, et al., "Improved oLigonticleolide site-directed mutagenesis using M13 vectors," Nucleic Acids Research, 1985, vol. 13, pp. 4331-4443.

Chang, A., et al., "Phenotypic expression in *E. coli* of a DNA sequence coding for mouse dihydrofolate reductase," Nature, 1978, vol. 275, pp. 617-624.

Chang, S. et al. "High frequency transformation of Bacillus subtilis protoplasts by plasmid DNA." Molecular Genetics and Genomics, vol. 168, 1979, pp. 111-115.

Chothia, "The nature of the accessible and buried surfaces in proteins," Journal of Molecular Biology, 1976, vol. 150, pp. 1-14.

McCutchen, et al. "Characterization of Extremely Thermostable Enzymatic Breakers (a-1,6-Galctosidase and b-1, 4 Mannanase) from the Hyperthermophilic Bacterium Thermotoga neapolitana 5068 for Hyrdolysis of Guar Gum" Biotechnology Bioengineering, 1996, vol. 52, pp. 332-339.

De Boer, et al. "The tac promoter: a functional hybrid derived from the trp and lac promoters." Proceedings of the National Academy of Sciences, USA, 1983, vol. 80(1), pp. 21-25.

Deutscher, "Rethinking your purification procedure," Methods in Enzymology, 1980, vol. 182, pp. 779-780.

Dutta, et al., "Endo-f1-mannanase activity present in cell wall extracts of lettuce endosperm prior to radicle emergence," Plant Physiology, 1997, vol. 113, pp. 155-161.

Emanuelsson, et al., "Locating proteins in the cell using targetp, signalp and related tools," Nature Protocols, 2007, vol. 2, pp. 953-971.

Freer, "Kinetic characterization of a β-glucosidase from a yeast, candida wickerhamii*," The Journal of Biological Chemistry, 1993, vol. 268, No. 13, pp. 9337-9342.

Goeddel, et al., "Synthesis of human fibroblast interferon by *E. coli*," Nucleic Acids Research, 1980, vol. 8, pp. 4057-4075.

Goeddel, et al., Direct expression in *Escherichia coli* of a DNA sequence coding for human growth hormone, Nature, 1979,281 pp. 544-548.

Gould, "Alkaline peroxide delignification of agricultural residues to enhance enzymatic saccharification," Biotechnology and Bioengineering, 1984, vol. 26, pp. 46-52.

Halstead, et al., "K-Galactosidase A from *Pseudomonas fuorescens* subsp. cellulosa: cloning, high level expression and its role in galactomannan hydrolysis," FEMS Microbiology Letters, 2000, vol. 192, pp. 197-203.

Henrissat & Cairoch, "Updating the sequence-based classification of glycosyl hydrolases," Biochemical Journal, 1996, vol. 316, pp. 695-696.

Henrissat, B. "A classification of glycosyl hydrolases based on amino acid sequence similarities," Biochemical Journal, 1991, vol. 280, pp. 309-316.

Hess, et al., "Cooperation of Glycolytic Enzymes," Advances in Enzyme Regulation, vol. 7, pp. 149-167, 1968.

Hitzeman, et al., "Isolation and characterization of the yeast 3-phosphoglycerokinase gene (PGK) by an immunological screening technique," The Journal of Biological Chemistry, 1980, vol. 255, pp. 2073-2080.

Holland, et al., "Isolation and identification of yeast messenger ribonucleic acids coding for enolase, glyceraldehyde-3-phosphate dehydrogenase, and phosphoglycerate kinase," Biochemistry, 1978, vol. 17, pp. 4900-4907.

Hsiao, et al., "High-frequency transformation of yeast by plasmids containing the cloned yeast ARG4 gene," Proceedings of the National Academy of Sciences, USA, 1979, vol. 76, No. 8,pp. 3829-3833.

International Search Report and Written Opinion from PCT Application No. PCT/US2013/072589 (Pub. No. WO 2014/088940 A2), mailed on Feb. 27, 2014.

Jones, "Proteinase mutants of *Saccharomyces cerevisiae*," Genetics, 1977, vol. 85, pp. 23-33.

Kingsman, et al., "Replication in *Saccharomyces cerevisiae* of plasmid, PBR313 carrying DNA from the yeast trpl region," Gene, 1979, vol. 7, pp. 141-152.

Knowles, et al., "Cellulase families and their genes," TIBTECH, 1987, vol. 5, pp. 255-261.

Krishna, et al., "Simultaneous saccharification and fermentation process of different cellulosic substrates using a recombinant *Saccharomyces cerevisiae* harbouring the β-glucosidase gene," Bioresource Technology, 2001, vol. 77, pp. 193-196.

Lee, et al., "Beta-Mannanase ameliorates viscosity-associated depression of growth in broiler chickens" Poultry Science, 2003, 82, pp. 1925-1931.

Lever, "A New Reaction for Colorimetric Determination of Carbohydrates," Analytical Biochemistry, 1972, vol. 47, pp. 273-279.

Ma, et al., "Characterization and gene cloning of a novel β-mannanase from *Alkaliphilic bacillus* sp.N-16-5," Extremophiles, 2004, vol. 8(6), pp. 447-454.

Merrifield, "Solid Phase Peptide Synthesis. I. The Synthesis of a Tetrapeptide," Journal of the American Chemical Society, 1963, vol. 85, pp. 2149-2154.

Needleman, et al., "A general method applicable to the search for similarities in the amino acid sequence of two proteins," Journal of Molecular Biology, 48:443 (1970) (1970) J. Mol. Biol. 48:443.

Nevalainen and Penttila, "A Comprehensive Treatise on Fungi as Experimental Systems for Basic and Applied Research," The Mycota II, Genetics and Biotechnology, 1995, pp. 303-319.

Ohmiya, et al., "Structure of Cellulases and Their Applications" Biotechnology & Genetic Engineering Reviews, 1997, vol. 14, pp. 365-414.

Pearson, et al., "Improved tools for biological sequence comparison," Proceedings of the National Academy of Sciences, USA, 1988, vol. 85, pp. 2444-2448.

Penttilä, et al. "A versatile transformation system for the cellulolytic filamentous fungus Trichoderma reesei," Gene, vol. 61, 1987, pp. 155-164.

Puchart, et al., "Purification and characterization of two forms of endo-beta-1,4-mannanase from a thermotolerant fungus, Aspergillus fumigatus IMI 385708 (formerly *Thermomyces lanuginosus* IMI 158749)," Biochimica et Biophysica Acta, 2004, vol. 1674, pp. 239-250.

Puls, "Chemistry and biochemistry of hemicelluloses: relationship between hemicellulose structure and enzymes required for hydrolysis," Macromolecular Symposia, 1997, vol. 120, pp. 183-196.

Schulein, "Cellulases of Trichoderma reesei." Methods in Enzymology, 1988, vol. 160, pp. 234-242.

Shaw, et al., "A general method for the transfer of cloned genes to plant cells," Gene, 1983, vol. 23, pp. 315-330.

Sheir-Neiss, "Characterization of the secreted cellulases of Trichoderma reesei wild type and mutants during controlled fermentations," Applied Microbiology Biotechnology, 1984, vol. 20 pp. 46-53.

Shpaer, Smith-Waterman database, "Gene Assist," Methods in Molecular Biology, 1997, vol. 70, pp. 173-187.

Smith, M. et al. "Protoplast transformation in coryneform bacteria and introduction of an α-amylase gene from Bacillus

(56) References Cited

OTHER PUBLICATIONS amyloliquefaciens into Brevibacterium lactofermentum," Applied and Enviromental Microbiology, 1986, vol. 51(3). pp. 634-639.

Smith, T. et al. "Comparison of biosequences," Advances in Applied Mathematics, 1981, vol. 2, pp. 482-489.

Stinchcomb, et al., "Isolation and characterization of a yeat chromosomal replicator," Nature, 1979, vol. 282, pp. 39-43.

Suurnakki, et al., "Hemicellulases in the bleaching of chemical pulps," Advances in Biochemical Engineering, Biotechnology, 1997, vol. 57, pp. 261-287.

Suurnakki, et al., "Trichoderma reesei cellulases and their core domains in the hydrolysis and modification of chemical pulp," Cellulose, 2000, vol. 7, pp. 189-209.

Teixeira, et al., "Alkaline and Peracetic Acid Pretreatments of Biomass for Ethanol Production," Applied Biochemistry and Biotechnology, 1999, vol. 77-79, pp. 19-34.

Thompson, et al., Clustal W: improving the sensitivity of progressive multiple sequence alignment through sequence weighting, position-specific gap penalties and weight matrix choice, Nucleic Acids Research, 1994, vol. 22, pp. 4673-4680.

Tian, et al., Robust cellulosic ethanol production from SPORL-pretreated lodgepolep pine using an adapted strain S. cerevisiae without detoxification, Bioresource Technology, 2010, vol. 101, pp. 8678-8685.

Tschumper, et al., "Sequence of a yeast DNA fragment containing a chromosomal replicator and the TRP1 gene," Gene, 1980, vol. 10, pp. 157-166.

Van Solingen, et al.,"Fusion of Yeast Spheroplasts," Journal of Bacteriology, 1977, vol. 130, pp. 946-947.

Vogtentanz, "A Bacillus subtilis fusion protein system to produce soybean Bowman-Birk protease inhibitor," Protein Expression and Purification, 2007, vol. 55, pp. 40-52.

Ward, et al., Use of Aspergillus overproducing mutants, cured for integrated plasmid, to overproduce heterologous proteins,Applied Microbiology Biotechnology, 1993, vol. 39, pp. 738-743.

Wells, et al., "Cassette mutagenesis: an efficient method for generation of multiple mutations at defined sites," Gene, 1985, vol. 34, pp. 315-323.

Wells, et al., "Importance of hydrogen-bond formation in stabilizing the transition state of subtilisin," Phil. Transactions of the Royal Society, London, 1986, Ser. A, vol. 317, pp. 415-423.

Xu, et al., "Cloning and expression in Pichia pastoris of a blue mussel (*Mytilus edulis*) b-mannanase gene," European Journal of Biochemistry, 2002, vol. 269, pp. 1753-1760.

Zhu, et al., "Sulfite pretreatment (SPORL) for robust enzymatic saccharification of spruce and red pine". Bioresource Technolology, 2009, vol. 100, pp. 2411-2418.

Zhu, et al., "Ethanol production from SPORL-pretreated lodgepole pine: preliminary evaluation of mass balance and process energy efficiency ," Applied Microbiology Biotechnology, 2010, vol. 86(5), pp. 1355-1365.

Zoller, et al., "Oligonucleotide-directed mutagenesis using M13-derived vectors: an efficient and general procedure for the production of point mutations in any fragment of DNA," Nucleic Acids Research, 1982, vol. 10, No. 20, pp. 6487-6500.

Ferrari, et al. "Genetics", pp. 57-72; in Bacillus, Harwood, ed. Plenum Publishing Corporation, 1989.

Genbank Accession No. AAT06599.1, beta-mannanase precursor [*Bacillus* sp. N16-5]; last modification date May 31, 2005.

Genbank Accession No. AY534912.1, *Bacillus* sp. N16-5 beta-mannanase precursor (manA) gene, complete cds: last modification date May 31, 2005.

* cited by examiner

FIGURE 1: Map of pML35 (aprE-BhcnmanA)
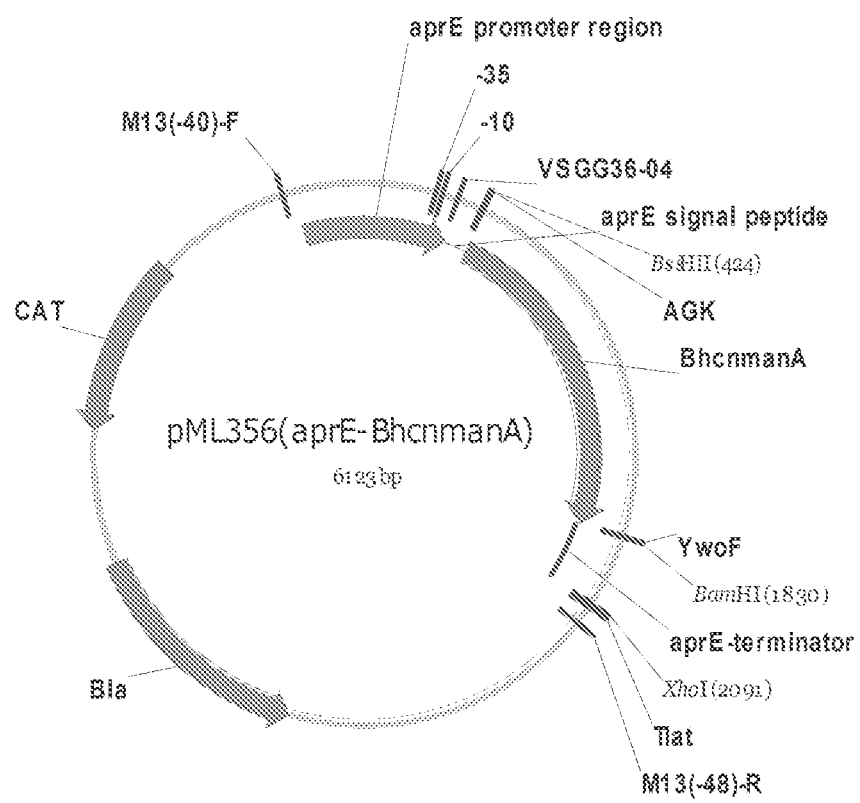

FIGURE 2: Map of pTrex3gM construct
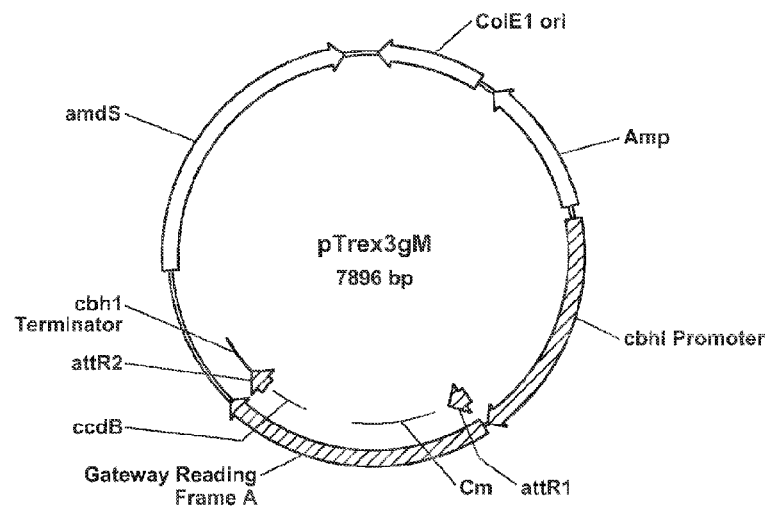
FIGURE 3: pH profile of Bhe Man2
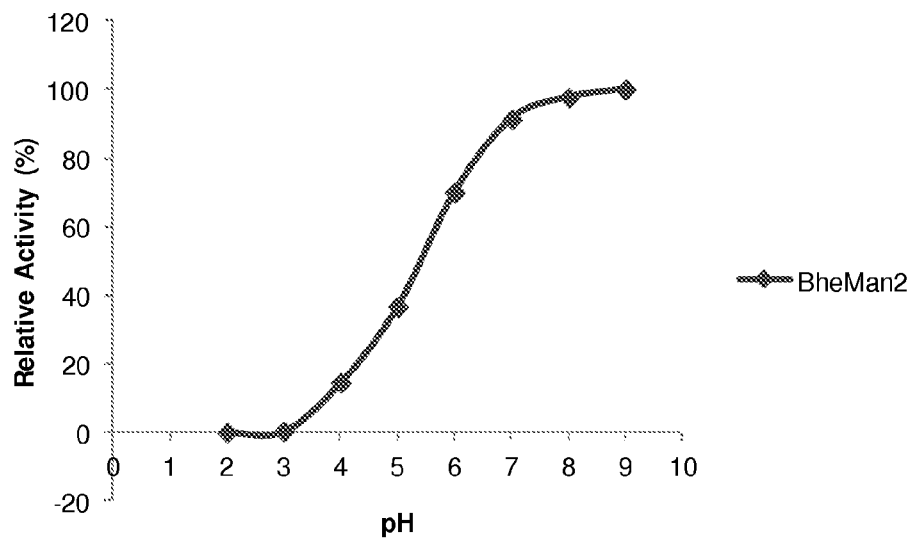

FIGURE 4: Temperature Profile of Bhe Man2
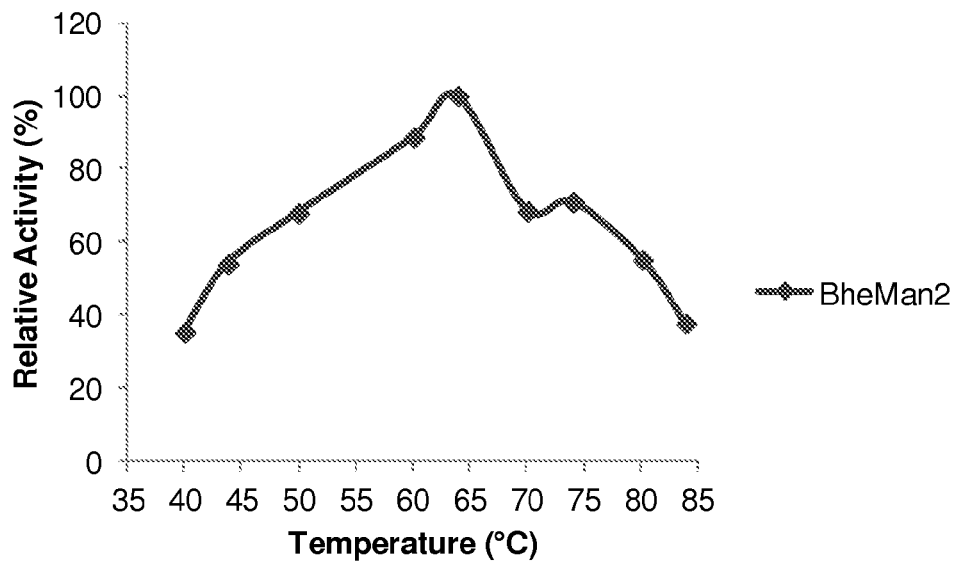
FIGURE 5: Thermostability Profile of Bhe Man2
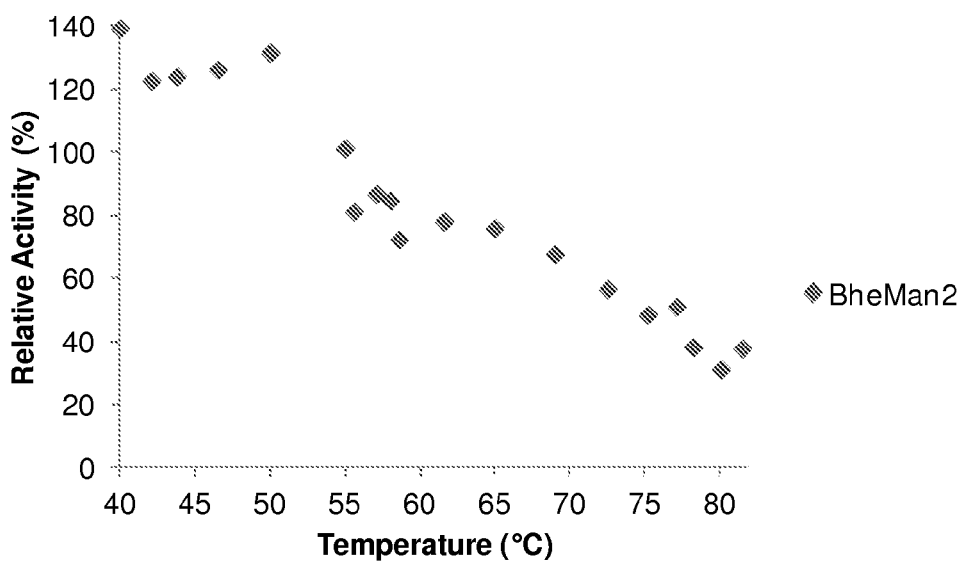

FIGURE 6A

Comparison of the results of hydrolysis of a KRAFT-pretreated softwood substrate FPP-27 after 24 hours, achieved by Accellerase® TRIO™, a 9 part Accellerase® TRIO™ and 1 part beta-mannanase blend (wherein the beta-mannanases are Bhe Man2, a beta-mannanase of *Streptomyces coelicolor* A3 (ScoMan1, SEQ ID NO:4), a beta-mannanase of *Bacillus caldovelox* (Bsp Man1, SEQ ID NO:5), and a beta-mannanase of *Micromonospora sp.* L5 (Msp Man2, SEQ ID NO:6))

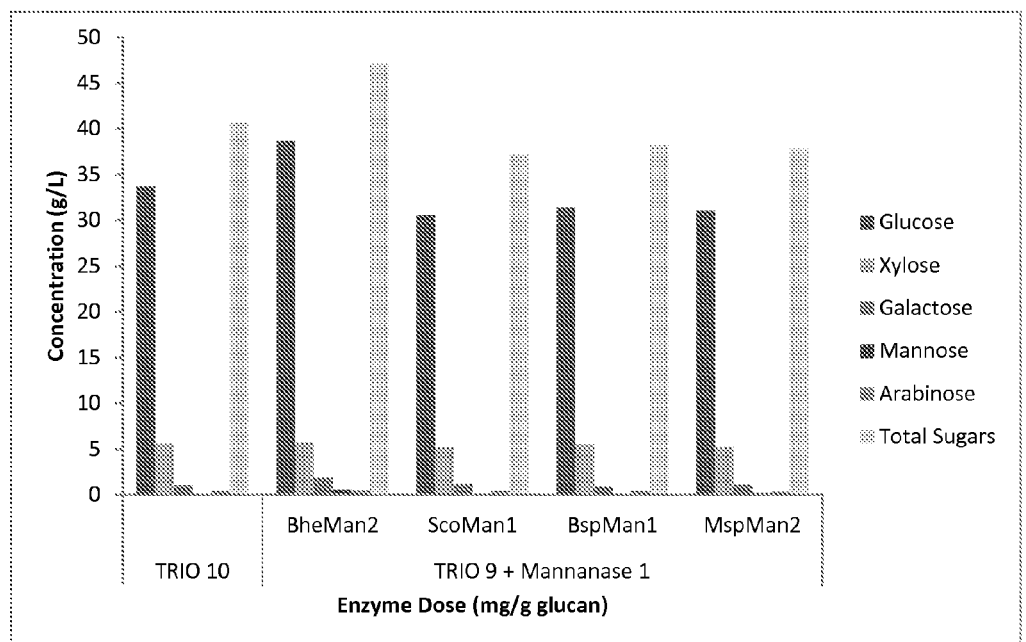

FIGURE 6B

Comparison of the results of hydrolysis of a KRAFT-pretreated softwood substrate FPP-27 after 48 hours, achieved by Accellerase® TRIO™, a 9 part Accellerase® TRIO™ and 1 part beta-mannanase blend (wherein the beta-mannanases are Bhe Man2, a beta-mannanase of *Streptomyces coelicolor* A3 (ScoMan1, SEQ ID NO:4), a beta-mannanase of *Bacillus caldovelox* (Bsp Man1, SEQ ID NO:5), and a beta-mannanase of *Micromonospora sp.* L5 (Msp Man2, SEQ ID NO:6))

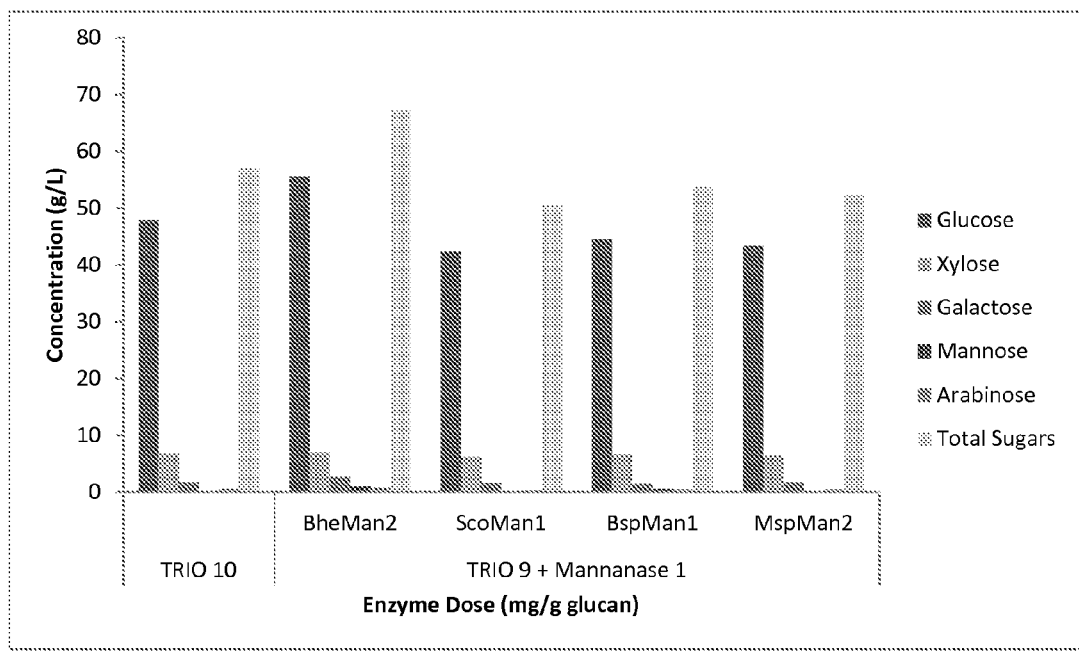

FIGURE 6C

Comparison of the results of hydrolysis of a KRAFT-pretreated softwood substrate FPP-27 after 72 hours, achieved by Accellerase® TRIO™, a 9 part Accellerase® TRIO™ and 1 part beta-mannanase blend (wherein the beta-mannanases are Bhe Man2, a beta-mannanase of *Streptomyces coelicolor* A3 (ScoMan1, SEQ ID NO:4), a beta-mannanase of *Bacillus caldovelox* (Bsp Man1, SEQ ID NO:5), and a beta-mannanase of *Micromonospora sp.* L5 (Msp Man2, SEQ ID NO:6))

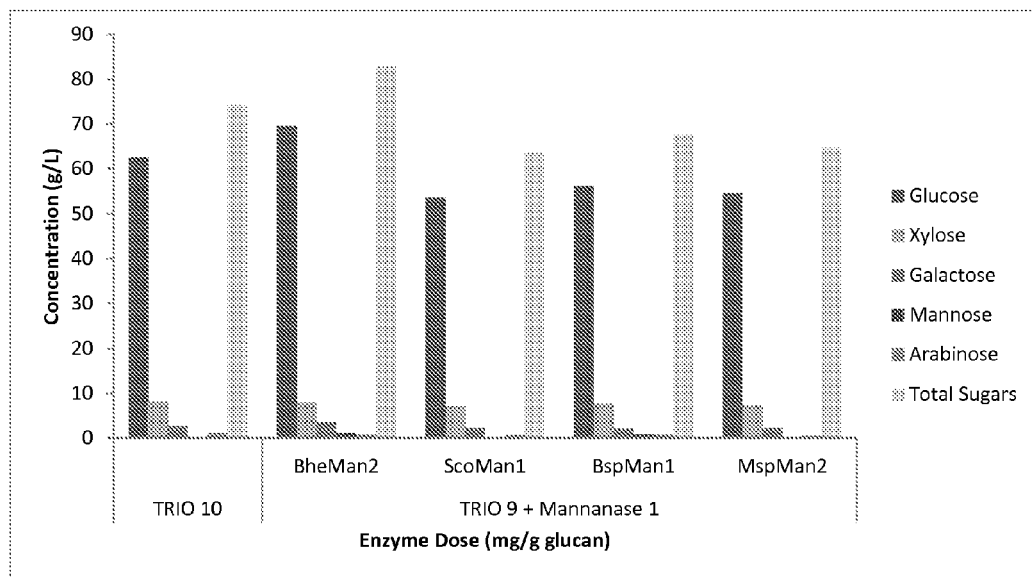

FIGURE 7

Comparison of the results of total hydrolysis of the KRAFT-pretreated softwood substrate FPP-27 by Accellerase® TRIO™ vs. a blend of 9 parts Accellerase® TRIO™ with 1 part (i.e., 10 wt.%) of a Bhe Man2 polypeptide, a *Streptomyces coelicolor* A3 beta-mannanase of SEQ ID NO:4 ("ScoMan1"), or a *Bacillus caldovelox* beta-mannanase of SEQ ID NO:5 ("Bsp Man1"), or a *Micromonospora sp.* L5 beta-mannanase of SEQ ID NO:6 ("Msp Man2"), following a time course of 24 hours to 72 hours.

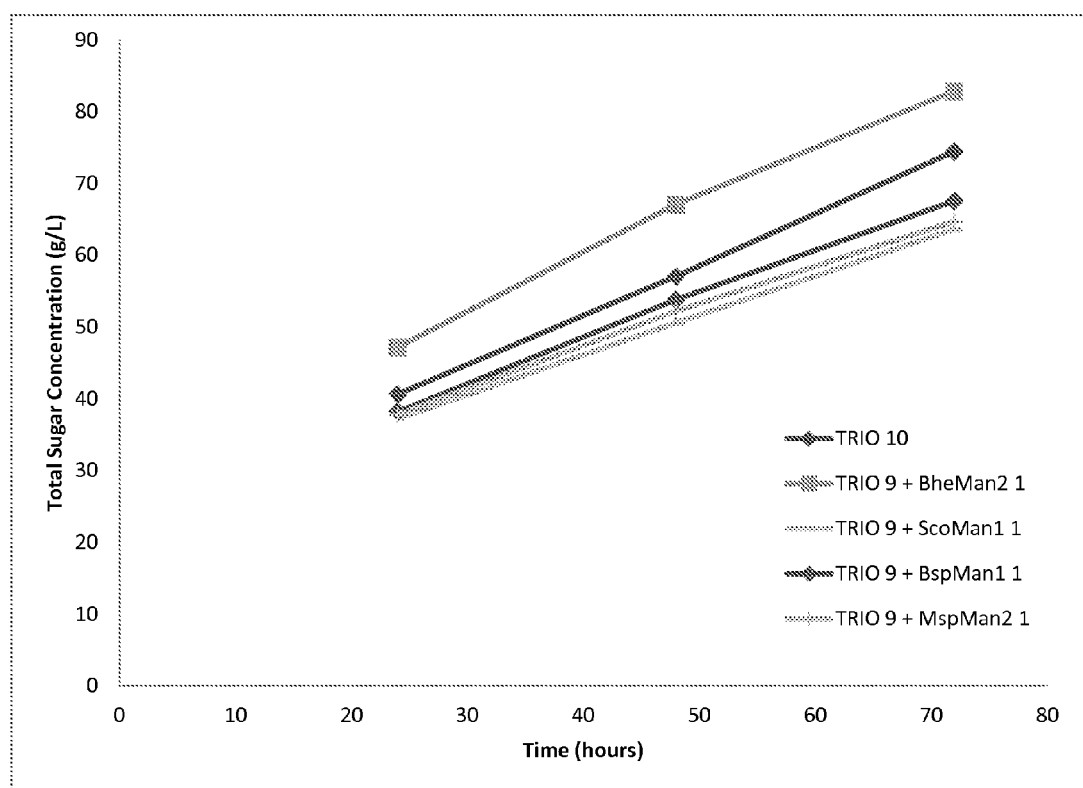

FIGURE 8A

SEQ ID NO:1 - Polynucleotide sequence encoding Bhe Man2 from *Bacillus hemicellulosilyticus*
ATGAAAAAAAGTCTATCTCAGATTTATCACTTAATTATTTGCGCACTTATTGCTAGTGTGGGGATC
ATGGGAATTACCACATCTCCATCAGCAGCAAGTTCAGGCTTTTATGTTGATGGCAATACGTT
ATATGACGCAAACGGGCAACCATTTGTCATGAGAGGTATTAACCATGGACATGCTTGGT
ATAAAGACACCGCTTCAACAGCTATTCCTGCCATTGCAGAGCAAGGCGCCAACACGATA
CGTATTGTTTTATCAGATGGCGGTCAATGGGAAAAAGACGACATTGACACCGTTCGTGAA
GTTATTGAGCTTGCGGAGCAAAATAAAATGGTGGCTGTCGTTGAAGTTCATGATGCCACG
GGCCGCGATTCGCGCAGTGATTTAAATCGAGCCGTTGATTATTGGATAGAAATGAAAGA
TGCGCTTATCGGTAAAGAAGATACGGTTATTATTAACATTGCAAACGAGTGGTATGGGA
GTTGGGATGGCTCAGCTTGGGCCGATGGCTATATTGATGTCATTCCGAAGCTTCGCGATG
CCGGCTTAACACACACCTTAATGGTTGATGCAGCAGGATGGGGGCAATATCCGCAATCT
ATTCATGATTACGGACAAGATGTGTTTAATGCAGATCCGTTAAAAAATACGATGTTCTCC
ATCCATATGTATGAGTATGCTGGTGGTGATGCTAACACTGTTAGATCAAATATTGATAGA
GTCATAGATCAAGACCTTGCTCTCGTAATAGGTGAATTCGGTCATAGACATACTGATGGT
GATGTTGATGAAGATACAATCCTTAGTTATTCTGAAGAAACTGGCACAGGGTGGCTCGCT
TGGTCTTGGAAAGGCAACAGTACCGAATGGGACTATTTAGACCTTTCAGAAGACTGGGC
TGGTCAACATTTAACTGATTGGGGGAATAGAATTGTCCACGGGGCCGATGGCTTACAGG
AAACCTCCAAACCATCCACCGTATTTTCAGATGATAACGGTGGTAGCCCTGAACCGCCAA
CTGCTACTACCTTGTATGACTTTGAAGGAAGTACACAAGGTTGGCATGGAAGCAACGTA
GCCGGTGGCCCTTGGTCCGTAACAGAGTGGGGTACTTCAGGTAACTACTCTTTAAAAGCC
GATGTAAATTTAACCTCAAATTCTTCACATGAACTGTATAGTGAACAAAGTCGTAATCTA
CACGGATACTCTCAGCTCAACGCAACCGTTCGCCATGCCAATTGGGGAAATCACGGTAAT
GGCATGAATGCAAGACTTTACGTGAAAACGGGCTCTGATTATACATGGTATAGCGGTCCT
TTTACACGTATCAATAGCTCCAACTCAGGTACAACGTTATCTTTTGATTTAAACAACATC
GAAAATAGTCATCATGTTAGGGAAATAGGCGTGCAATTTTCAGCGGCAGATAATAGCAG
CGGTCAAACTGCTCTATACGTTGATAATGTTACTTTAAGA SEQ ID NO:2 - Polypeptide sequence of precursor wild type Bhe Man2 from *Bacillus hemicellulosilyticus*. The predicted signal peptide is shown in italic type face.

*MKKSLSQIYHLIICALIASVGIMGITTSPSAA*SSGFYVDGNTLYDANGQPFVMRGINHGHAWYKD
TASTAIPAIAEQGANTIRIVLSDGGQWEKDDIDTVREVIELAEQNKMVAVVEVHDATGRDSR
SDLNRAVDYWIEMKDALIGKEDTVIINIANEWYGSWDGSAWADGYIDVIPKLRDAGLTHTL
MVDAAGWGQYPQSIHDYGQDVFNADPLKNTMFSIHMYEYAGGDANTVRSNIDRVIDQDLA
LVIGEFGHRHTDGDVDEDTILSYSEETGTGWLAWSWKGNSTEWDYLDLSEDWAGQHLTDW
GNRIVHGADGLQETSKPSTVFSDDNGGSPEPPTATTLYDFEGSTQGWHGSNVAGGPWSVTE
WGTSGNYSLKADVNLTSNSSHELYSEQSRNLHGYSQLNATVRHANWGNHGNGMNARLYV
KTGSDYTWYSGPFTRINSSNSGTTLSFDLNNIENSHHVREIGVQFSAADNSSGQTALYVDNVT
LR

Figure 8B

**SEQ ID NO:3 - Polypeptide sequence of the mature Bhe Man2 from *Bacillus hemicellulosilyticus***

SSGFYVDGNTLYDANGQPFVMRGINHGHAWYKDTASTAIPAIAEQGANTIRIVLSDGGQWE
KDDIDTVREVIELAEQNKMVAVVEVHDATGRDSRSDLNRAVDYWIEMKDALIGKEDTVIINI
ANEWYGSWDGSAWADGYIDVIPKLRDAGLTHTLMVDAAGWGQYPQSIHDYGQDVFNADP
LKNTMFSIHMYEYAGGDANTVRSNIDRVIDQDLALVIGEFGHRHTDGDVDEDTILSYSEETG
TGWLAWSWKGNSTEWDYLDLSEDWAGQHLTDWGNRIVHGADGLQETSKPSTVFSDDNGG
SPEPPTATTLYDFEGSTQGWHGSNVAGGPWSVTEWGTSGNYSLKADVNLTSNSSHELYSEQS
RNLHGYSQLNATVRHANWGNHGNGMNARLYVKTGSDYTWYSGPFTRINSSNSGTTLSFDL
NNIENSHHVREIGVQFSAADNSSGQTALYVDNVTLR

**SEQ ID NO:4 - Polypeptide sequence of "ScoMan1" herein from *Streptomyces coelicolor* strain A3**

MRKPRSTLITTAGMAFAAVLGLLFALAGPSAGRAEAAAGGIHVSNGRVLEGNGSVFVMRGV
NHAYTWYPDRTGSIADIAAKGANTVRVVLSSGGRWTKTSASEVSALIGQCKANKVICVLEV
HDTTGYGEDGAATSLDQAADYWVSVKSALEGQEDYVVVNIGNEPFGNTNYTAWTDATKSA
IGKLRGAGLDHALMVDAPNWGQDWSGTMRSNAASVFASDPDRNTVFSVHMYGVYDTAAE
VRDYLNAFVGSGLPIVVGEFGDQHSDGNPDEDAIMATAQSLGVGYLGWSWSGNGGGVEYL
DMVNGFDPNSLTSWGNRIFYGSNGIAATSRTATVYGGGGSTGGTAPNGYPYCVNGGASDP
DGDGWGWENSRSCVVRGSAADH

**SEQ ID NO:5 - Polypeptide sequence of "Bsp Man1" herein from *Bacillus caldovelox***

MNKKWSYTFIALLVSIVCAVVPIFFSQNNVHAKTKREPATPTKDNEFVYRKGDKLMIGNKEF
RFVGTNNYYLHYKSNQMIDDVIESAKKMGIKVIRLWGFFDGMTSENQAHNTYMQYEMGKY
MGEGPIPKELEGAQNGFERLDYTIYKAKQEGIRLVIVLTNNWNNFGGMMQYVNWIGETNHD
LFYTDERIKTAYKNYVHYLINRKNQYTGIIYKNEPTIMAWELANEPRNDSDPTGDTLVRWAD
EMSTYIKSIDPHHLVAVGDEGFFRRSSGGFNGEGSYMYTGYNGVDWDRLIALKNIDYGTFHL
YPEHWGISPENVEKWGEQYILDHLAAGKKAKKPVVLEEYGISATGVQNREMIYDTWNRTMF
EHGGTGAMFWLLTGIDDNPESADENGYYPDYDGFRIVNDHSSVTNLLKTYAKLFNGDRHVE
KEPKVYFAFPAKPQDVRGTYRVKVKVASDQHKVQKVQLQLSSHDEAYTMKYNASFDYYEF
DWDTTKEIEDSTVTLKATATLTNKQTIASDEVTVNIQNASAYEIIKQFSFDSDMNNVYADGT
WQANFGIPAISTPKTRCLRVNVDLPGNADWEEVKVKISPISELSETSRISFDLLLPRVDVNGAL
RPYIALNPGWIKIGVDQYHVNVNDLTTVTIHNQQYKLLHVNVEFNAMPNVNELFLNIVGNKL
AYKGPIYIDNVTLFKKI

**SEQ ID NO:6 - Polypeptide sequence of "Msp Man2" herein from *Micromonospora sp.* strain L5**

MKKLLSVAGAALLTALAAVFALGQPAHAATGFSVSNGRLYDANGVEFVMRGVNHAHTWY
PQQTSSFANIKALGANTVRVVLSSGDRWTKNSAADVANVISLCKANRMICVLEVHDTTGYG
EDGAATTLAKATDYWLSIADVLKGQEKYVIVNIGNEPFGNQGYSAWTTDTSNAIKRLRAAG
LTHTIMVDAPNWGQDWTFTMRDNAGTVFAADPQRNTVFSIHMYGVFDTAAEISDYLGRFRT
AGLPIVVGEFGFNHSDGNPDEDAIMAYAQANGIGYLGWSWSGNGGGVEYLDMTTAFNPAQ
LTSWGQRIFNGANGIAATSREASVYAGSTPTASPTGSPTTSPTPTSSPSPTPPPTTTPPPSGGCTA
TYTVANSWQGGFQGEVKVTAGAAAITGWTVRWTFANGQSVTQAWNASVSNSGSAYTARN
VDYNGRLGVGASTSFGFIGSWTGTNSTPAVTCTAS

FIGURE 8C

SEQ ID NO:9 - the confirmed nucleotide sequence of the *bhe Man2* gene from the plasmid pML356 (*aprE* signal sequence is in italics)

*GTGAGAAGCAAAAAATTGTGGATCAGCTTGTTGTTTGCGTTAACGTTAATCTTTACGATGGCGTT*
*CAGCAACATGAGCGCGCAGGCT*GCTGGAAAAAGTTCAGGCTTTTATGTTGATGGCAATAC
GTTATATGACGCAAACGGGCAACCATTTGTCATGAGAGGTATTAACCATGGACATGCTTG
GTATAAAGACACCGCTTCAACAGCTATTCCTGCCATTGCAGAGCAAGGCGCCAACACGA
TACGTATTGTTTTATCAGATGGCGGTCAATGGGAAAAAGACGACATTGACACCGTTCGTG
AAGTTATTGAGCTTGCGGAGCAAAATAAAATGGTGGCTGTCGTTGAAGTTCATGATGCCA
CGGGCCGCGATTCGCGCAGTGATTTAAATCGAGCCGTTGATTATTGGATAGAAATGAAA
GATGCGCTTATCGGTAAAGAAGATACGGTTATTATTAACATTGCAAACGAGTGGTATGG
GAGTTGGGATGGCTCAGCTTGGGCCGATGGCTATATTGATGTCATTCCGAAGCTTCGCGA
TGCCGGCTTAACACACACCTTAATGGTTGATGCAGCAGGATGGGGGCAATATCCGCAAT
CTATTCATGATTACGGACAAGATGTGTTTAATGCAGATCCGTTAAAAAATACGATGTTCT
CCATCCATATGTATGAGTATGCTGGTGGTGATGCTAACACTGTTAGATCAAATATTGATA
GAGTCATAGATCAAGACCTTGCTCTCGTAATAGGTGAATTCGGTCATAGACATACTGATG
GTGATGTTGATGAAGATACAATCCTTAGTTATTCTGAAGAAACTGGCACAGGGTGGCTCG
CTTGGTCTTGGAAAGGCAACAGTACCGAATGGGACTATTTAGACCTTTCAGAAGACTGG
GCTGGTCAACATTTAACTGATTGGGGGAATAGAATTGTCCACGGGGCCGATGGCTTACA
GGAAACCTCCAAACCATCCACCGTATTTTCAGATGATAACGGTGGTAGCCCTGAACCGCC
AACTGCTACTACCTTGTATGACTTTGAAGGAAGTACACAAGGTTGGCATGGAAGCAACG
TAGCCGGTGGCCCTTGGTCCGTAACAGAGTGGGGTACTTCAGGTAACTACTCTTTAAAAG
CCGATGTAAATTTAACCTCAAATTCTTCACATGAACTGTATAGTGAACAAAGTCGTAATC
TACACGGATACTCTCAGCTCAACGCAACCGTTCGCCATGCCAATTGGGGAAATCACGGTA
ATGGCATGAATGCAAGACTTTACGTGAAAACGGGCTCTGATTATACATGGTATAGCGGTC
CTTTTACACGTATCAATAGCTCCAACTCAGGTACAACGTTATCTTTTGATTTAAACAACAT
CGAAAATAGTCATCATGTTAGGGAAATAGGCGTGCAATTTTCAGCGGCAGATAATAGCA
GCGGTCAAACTGCTCTATACGTTGATAATGTTACTTTAAGA

SEQ ID NO:10 - the amino acid sequence of the Bhe Man2 full-length polypeptide expressed from the plasmid pML356, with the signal sequence shown in italics and the three residue addition shown in bold

*MRSKKLWISLLFALTLIFTMAFSNMSAQA*AGKSSGFYVDGNTLYDANGQPFVMRGINIIGHAW
YKDTASTAIPAIAEQGANTIRIVLSDGGQWEKDDIDTVREVIELAEQNKMVAVVEVHDATGR
DSRSDLNRAVDYWIEMKDALIGKEDTVIINIANEWYGSWDGSAWADGYIDVIPKLRDAGLT
HTLMVDAAGWGQYPQSIHDYGQDVFNADPLKNTMFSIHMYEYAGGDANTVRSNIDRVIDQ
DLALVIGEFGHRHTDGDVDEDTILSYSEETGTGWLAWSWKGNSTEWDYLDLSEDWAGQHL
TDWGNRIVHGADGLQETSKPSTVFSDDNGGSPEPPTATTLYDFEGSTQGWHGSNVAGGPWS
VTEWGTSGNYSLKADVNLTSNSSHELYSEQSRNLHGYSQLNATVRHANWGNHGNGMNARL
YVKTGSDYTWYSGPFTRINSSNSGTTLSFDLNNIENSHHVREIGVQFSAADNSSGQTALYVDN
VTLR

FIGURE 8D

SEQ ID NO:11 - the amino acid sequence of the Bhe Man2 mature polypeptide expressed from the plasmid pML356, with the three residue amino-terminal extension based on the predicted cleavage site shown in bold:

AGKSSGFYVDGNTLYDANGQPFVMRGINHGHAWYKDTASTAIPAIAEQGANTIRIVLSDGGQWEKDD
IDTVREVIELAEQNKMVAVVEVIIDATGRDSRSDLNRAVDYWIEMKDALIGKEDTVIINIANEWYGSW
DGSAWADGYIDVIPKLRDAGLTHTLMVDAAGWGQYPQSIHDYGQDVFNADPLKNTMFSIHMYEYAG
GDANTVRSNIDRVIDQDLALVIGEFGHRHTDGDVDEDTILSYSEETGTGWLAWSWKGNSTEWDYLDL
SEDWAGQHLTDWGNRIVHGADGLQETSKPSTVFSDDNGGSPEPPTATTLYDFEGSTQGWHGSNVAGG
PWSVTEWGTSGNYSLKADVNLTSNSSHELYSEQSRNLHGYSQLNATVRHANWGNHGNGMNARLYV
KTGSDYTWYSGPFTRINSSNSGTTLSFDLNNIENSHHVREIGVQFSAADNSSGQTALYVDNVTLR

SEQ ID NO:12 - the amino acid sequence of the Bhe Man2 mature polypeptide after the three-residue amino terminal extension were cleaved off from the predicted cleavage site SSGFYVDGNTLYDANGQPFVMRGINHGHAWYKDTASTAIPAIAEQGANTIRIVLSDGGQWEKDDIDTV
REVIELAEQNKMVAVVEVHDATGRDSRSDLNRAVDYWIEMKDALIGKEDTVIINIANEWYGSWDGSA
WADGYIDVIPKLRDAGLTHTLMVDAAGWGQYPQSIHDYGQDVFNADPLKNTMFSIHMYEYAGGDAN
TVRSNIDRVIDQDLALVIGEFGHRHTDGDVDEDTILSYSEETGTGWLAWSWKGNSTEWDYLDLSEDW
AGQHLTDWGNRIVHGADGLQETSKPSTVFSDDNGGSPEPPTATTLYDFEGSTQGWHGSNVAGGPWSV
TEWGTSGNYSLKADVNLTSNSSHELYSEQSRNLHGYSQLNATVRHANWGNHGNGMNARLYVKTGSD
YTWYSGPFTRINSSNSGTTLSFDLNNIENSHHVREIGVQFSAADNSSGQTALYVDNVTLR SEQ ID NO:13 - the *aprE* signal polypeptide sequence for expression of Bhe Man2 polypeptides in *B. subtilis*, for example.

MRSKKLWISLLFALTLIFTMAFSNMSAQA

SEQ ID NO:14 – a xylanase signal sequence that may be used for expression of Bhe Man2 polypeptides in *Trichoderma reesei.*

MVSFTSLLAASPPSRASCRPAAEVESVAVEKR

SEQ ID NO:15 – another xylanase signal sequence that may be used for expression of Bhe Man2 polypeptides in *Trichoderma reesei*

MKANVILCLLAPLVAA

SEQ ID NO:16 – a beta-glucosidase signal sequence that may be used for expression of Bhe Man2 polypeptides in *Trichoderma reesei*

MRYRTAAALALATGPFARA

SEQ ID NO:17: a cellobiohydrolase signal sequence that may be used for expression of Bhe Man2 polypeptides in *Trichoderma reesei*

MIVGILTTLATLATLAAS

FIGURE 8E

SEQ ID NO:18: a cellobiohydrolase signal sequence that may be used for expression of Bhe Man2 polypeptides in *Trichoderma reesei*.

MYRKLAVISAFLATARA

SEQ ID NO:19: an Fv3A signal sequence that may be used for expression of Bhe Man2 polypeptides in *Fusarium verticillioides*

MLLNLQVAASALSLSLLGGLAEA

SEQ ID NO:20: an Fv3C signal sequence that may be used for expression of Bhe Man2 polypeptides in *Fusarium verticillioides*

MKLNWVAAALSIGAAGTDS

SEQ ID NO:21: an Fv3D signal sequence that may be used for expression of Bhe Man2 polypeptides in *Fusarium verticillioides*

MASIRSVLVSGLLAAGVNA

SEQ ID NO:22: an Fv43A signal sequence that may be used for expression of Bhe Man2 polypeptides in *Fusarium verticillioides*

MWLTSPLLFASTLLGLTGVALA

SEQ ID NO:23: an Fv43B signal sequence that may be used for expression of Bhe Man2 polypeptides in *Fusarium verticillioides*

MRFSWLLCPLLAMGSA

SEQ ID NO:24: an Fv43C signal sequence that may be used for expression of Bhe Man2 polypeptides in *Fusarium verticillioides*

MRLLSFPSHLLVAFLTLKEASS

SEQ ID NO:25: an Fv43D signal sequence that may be used for expression of Bhe Man2 polypeptides in *Fusarium verticillioides*

MQLKFLSSALLLSLTGNCAA

FIGURE 8F

SEQ ID NO:26: an Fv43E signal sequence that may be used for expression of Bhe Man2 polypeptides in *Fusarium verticillioides*

MKVYWLVAWATSLTPALA

SEQ ID NO:27: an Fv51A signal sequence that may be used for expression of Bhe Man2 polypeptides in *Fusarium verticillioides*

MVRFSSILAAAACFVAVES

SEQ ID NO:28: a Pa51A signal sequence that may be used for expression of Bhe Man2 polypeptides in *Podospora anserina*

MIHLKPALAALLALSTQCVA

SEQ ID NO:29: a Pa3D signal sequence that may be used for expression of Bhe Man2 polypeptides in *Podospora anserina*

MALQTFFLLAAAMLANA

SEQ ID NO:30: a Pa3G signal sequence that may be used for expression of Bhe Man2 polypeptides in *Podospora anserina*

MKLNKPFLAIYLAFNLAEA

SEQ ID NO:31, a Cg51B signal sequence that may be used for expression of Bhe Man2 polypeptides in *Chaetomium globosum*

MAPLSLRALSLLALTGAAAA

SEQ ID NO:32, a xylanase signal sequence that may be used for expression of Bhe Man2 polypeptides in *Thermoascus aurantiacus*

MVRPTLLTSLLLAPFAAA

SEQ ID NO:33: an At10A signal sequence that may be used for expression of Bhe Man2 polypeptides in *Aspergillus terreus*

MHMHSLVAALAAGTLPLLASA

FIGURE 8G

SEQ ID NO:34: an Af10A signal sequence that may be used for expression of Bhe Man2 polypeptides in *Aspergillus fumigatus*

MVHLSSLAAALAALPLVYG

SEQ ID NO:35: an Af10B signal sequence that may be used for expression of Bhe Man2 polypeptides in *Aspergillus fumigatus*

MRFSLAATTLLAGLATA

SEQ ID NO:36: an Af10C signal sequence that may be used for expression of Bhe Man2 polypeptides in *Aspergillus fumigatus*

MVVLSKLVSSILFASLVSA

SEQ ID NO:37: an Ak10A signal sequence that may be used for expression of Bhe Man2 polypeptides in *Aspergillus kawachii*

MVQIKAAALAMLFASHVLS

SEQ ID NO:38: a xylanase signal sequence that may be used to express Bhe Man2 polypeptides in *Magnaporthe grisea*

MKASSVLLGLAPLAALA

SEQ ID NO:39: a mf(alpha) signal sequence that may be used to express Bhe Man2 polypeptides in yeast

MRFPSIFTAVLFAASSALA

SEQ ID NO:40: a mf(alpha) pre-pro signal sequence that may be used to express Bhe Man2 polypeptides in yeast MRFPSIFTAVLFAASSALAAPVNTTTEDETAQIPAEAVIGYLDLEGDFDVAVLPFSNSTNNGLL
FINTTIASIAAKEEGVSLDKR SEQ ID NO:41: a suc2 signal sequence that may be used to express Bhe Man2 polypeptides in yeast

MLLQAFLFLLAGFAAKISAR

SEQUENCE LISTING

```
<160> NUMBER OF SEQ ID NOS: 41

<210> SEQ ID NO 1
<211> LENGTH: 1479
<212> TYPE: DNA
<213> ORGANISM: Bacillus hemicellulosilyticus
<220> FEATURE:
<221> NAME/KEY: misc_feature
<223> OTHER INFORMATION: Polynucleotide sequence encoding Bhe Man2 from
      Bacillus hemicellulosilyticus

<400> SEQUENCE: 1
atgaaaaaaa gtctatctca gatttatcac ttaattattt gcgcacttat tgctagtgtg      60
gggatcatgg gaattaccac atctccatca gcagcaagtt caggcttta tgttgatggc     120 aatacgttat atgacgcaaa cgggcaacca tttgtcatga gaggtattaa ccatggacat     180
gcttggtata aagacaccgc ttcaacagct attcctgcca ttgcagagca aggcgccaac     240
acgatacgta ttgttttatc agatggcggt caatgggaaa aagacgacat tgacaccgtt     300
cgtgaagtta ttgagcttgc ggagcaaaat aaaatggtgg ctgtcgttga agttcatgat     360
gccacgggcc gcgattcgcg cagtgattta aatcgagccg ttgattattg gatagaaatg     420
aaagatgcgc ttatcggtaa agaagatacg gttattatta acattgcaaa cgagtggtat     480
gggagttggg atggctcagc ttgggccgat ggctatattg atgtcattcc gaagcttcgc     540
gatgccggct aacacacac cttaatggtt gatgcagcag gatgggggca atatccgcaa     600
tctattcatg attacggaca agatgtgttt aatgcagatc cgttaaaaaa tacgatgttc     660
tccatccata tgtatgagta tgctggtggt gatgctaaca ctgttagatc aaatattgat     720
agagtcatag atcaagacct tgctctcgta ataggtgaat tcggtcatag acatactgat     780
ggtgatgttg atgaagatac aatccttagt tattctgaag aaactggcac agggtggctc     840
gcttggtctt ggaaaggcaa cagtaccgaa tgggactatt tagacctttc agaagactgg     900
```

```
gctggtcaac atttaactga ttgggggaat agaattgtcc acggggccga tggcttacag    960
gaaacctcca aaccatccac cgtatttcca gatgataacg gtggtagccc tgaaccgcca   1020
actgctacta ccttgtatga ctttgaagga agtacacaag gttggcatgg aagcaacgta   1080
gccggtggcc cttggtccgt aacagagtgg ggtacttcag gtaactactc tttaaaagcc   1140
gatgtaaatt taacctcaaa ttcttcacat gaactgtata gtgaacaaag tcgtaatcta   1200
cacggatact ctcagctcaa cgcaaccgtt cgccatgcca attggggaaa tcacggtaat   1260
ggcatgaatg caagacttta cgtgaaaacg ggctctgatt atacatggta tagcggtcct   1320
tttacacgta tcaatagctc caactcaggt acaacgttat cttttgattt aaacaacatc   1380
gaaaatagtc atcatgttag ggaaataggc gtgcaatttt cagcggcaga taatagcagc   1440
ggtcaaactg ctctatacgt tgataatgtt actttaaga                          1479
```

<210> SEQ ID NO 2
<211> LENGTH: 493
<212> TYPE: PRT
<213> ORGANISM: Bacillus hemicellulosilyticus
<220> FEATURE:
<221> NAME/KEY: misc_feature
<223> OTHER INFORMATION: Polypeptide sequence of precursor wild type Bhe Man2 from Bacillus hemicellulosilyticus

<400> SEQUENCE: 2

```
Met Lys Lys Ser Leu Ser Gln Ile Tyr His Leu Ile Ile Cys Ala Leu
1               5                   10                  15

Ile Ala Ser Val Gly Ile Met Gly Ile Thr Thr Ser Pro Ser Ala Ala
            20                  25                  30

Ser Ser Gly Phe Tyr Val Asp Gly Asn Thr Leu Tyr Asp Ala Asn Gly
        35                  40                  45

Gln Pro Phe Val Met Arg Gly Ile Asn His Gly His Ala Trp Tyr Lys
    50                  55                  60

Asp Thr Ala Ser Thr Ala Ile Pro Ala Ile Ala Glu Gln Gly Ala Asn
65                  70                  75                  80

Thr Ile Arg Ile Val Leu Ser Asp Gly Gly Gln Trp Glu Lys Asp Asp
                85                  90                  95

Ile Asp Thr Val Arg Glu Val Ile Glu Leu Ala Glu Gln Asn Lys Met
            100                 105                 110

Val Ala Val Val Glu Val His Asp Ala Thr Gly Arg Asp Ser Arg Ser
        115                 120                 125

Asp Leu Asn Arg Ala Val Asp Tyr Trp Ile Glu Met Lys Asp Ala Leu
    130                 135                 140

Ile Gly Lys Glu Asp Thr Val Ile Ile Asn Ile Ala Asn Glu Trp Tyr
145                 150                 155                 160

Gly Ser Trp Asp Gly Ser Ala Trp Ala Asp Gly Tyr Ile Asp Val Ile
                165                 170                 175

Pro Lys Leu Arg Asp Ala Gly Leu Thr His Thr Leu Met Val Asp Ala
            180                 185                 190

Ala Gly Trp Gly Gln Tyr Pro Gln Ser Ile His Asp Tyr Gly Gln Asp
        195                 200                 205

Val Phe Asn Ala Asp Pro Leu Lys Asn Thr Met Phe Ser Ile His Met
    210                 215                 220

Tyr Glu Tyr Ala Gly Gly Asp Ala Asn Thr Val Arg Ser Asn Ile Asp
225                 230                 235                 240

Arg Val Ile Asp Gln Asp Leu Ala Leu Val Ile Gly Glu Phe Gly His
```

```
                        245                 250                 255
Arg His Thr Asp Gly Asp Val Asp Glu Asp Thr Ile Leu Ser Tyr Ser
            260                 265                 270

Glu Glu Thr Gly Thr Gly Trp Leu Ala Trp Ser Trp Lys Gly Asn Ser
        275                 280                 285

Thr Glu Trp Asp Tyr Leu Asp Leu Ser Glu Asp Trp Ala Gly Gln His
    290                 295                 300

Leu Thr Asp Trp Gly Asn Arg Ile Val His Gly Ala Asp Gly Leu Gln
305                 310                 315                 320

Glu Thr Ser Lys Pro Ser Thr Val Phe Ser Asp Asn Gly Gly Ser
            325                 330                 335

Pro Glu Pro Pro Thr Ala Thr Leu Tyr Asp Phe Glu Gly Ser Thr
        340                 345                 350

Gln Gly Trp His Gly Ser Asn Val Ala Gly Gly Pro Trp Ser Val Thr
    355                 360                 365

Glu Trp Gly Thr Ser Gly Asn Tyr Ser Leu Lys Ala Asp Val Asn Leu
370                 375                 380

Thr Ser Asn Ser Ser His Glu Leu Tyr Ser Glu Gln Ser Arg Asn Leu
385                 390                 395                 400

His Gly Tyr Ser Gln Leu Asn Ala Thr Val Arg His Ala Asn Trp Gly
            405                 410                 415

Asn His Gly Asn Gly Met Asn Ala Arg Leu Tyr Val Lys Thr Gly Ser
        420                 425                 430

Asp Tyr Thr Trp Tyr Ser Gly Pro Phe Thr Arg Ile Asn Ser Ser Asn
    435                 440                 445

Ser Gly Thr Thr Leu Ser Phe Asp Leu Asn Asn Ile Glu Asn Ser His
450                 455                 460

His Val Arg Glu Ile Gly Val Gln Phe Ser Ala Ala Asp Asn Ser Ser
465                 470                 475                 480

Gly Gln Thr Ala Leu Tyr Val Asp Asn Val Thr Leu Arg
            485                 490

<210> SEQ ID NO 3
<211> LENGTH: 461
<212> TYPE: PRT
<213> ORGANISM: Bacillus hemicellulosilyticus
<220> FEATURE:
<221> NAME/KEY: misc_feature
<223> OTHER INFORMATION: Polypeptide sequence of the mature Bhe Man2
      from Bacillus hemicellulosilyticus

<400> SEQUENCE: 3

Ser Ser Gly Phe Tyr Val Asp Gly Asn Thr Leu Tyr Asp Ala Asn Gly
1               5                   10                  15

Gln Pro Phe Val Met Arg Gly Ile Asn His Gly His Ala Trp Tyr Lys
            20                  25                  30

Asp Thr Ala Ser Thr Ala Ile Pro Ala Ile Ala Glu Gln Gly Ala Asn
        35                  40                  45

Thr Ile Arg Ile Val Leu Ser Asp Gly Gly Gln Trp Glu Lys Asp Asp
    50                  55                  60

Ile Asp Thr Val Arg Glu Val Ile Glu Leu Ala Glu Gln Asn Lys Met
65                  70                  75                  80

Val Ala Val Val Glu Val His Asp Ala Thr Gly Arg Asp Ser Arg Ser
                85                  90                  95

Asp Leu Asn Arg Ala Val Asp Tyr Trp Ile Glu Met Lys Asp Ala Leu
            100                 105                 110
```

Ile Gly Lys Glu Asp Thr Val Ile Asn Ile Ala Asn Glu Trp Tyr
            115                 120                 125

Gly Ser Trp Asp Gly Ser Ala Trp Ala Asp Gly Tyr Ile Asp Val Ile
130                 135                 140

Pro Lys Leu Arg Asp Ala Gly Leu Thr His Thr Leu Met Val Asp Ala
145                 150                 155                 160

Ala Gly Trp Gly Gln Tyr Pro Gln Ser Ile His Asp Tyr Gly Gln Asp
            165                 170                 175

Val Phe Asn Ala Asp Pro Leu Lys Asn Thr Met Phe Ser Ile His Met
            180                 185                 190

Tyr Glu Tyr Ala Gly Gly Asp Ala Asn Thr Val Arg Ser Asn Ile Asp
            195                 200                 205

Arg Val Ile Asp Gln Asp Leu Ala Leu Val Ile Gly Glu Phe Gly His
210                 215                 220

Arg His Thr Asp Gly Asp Val Asp Glu Asp Thr Ile Leu Ser Tyr Ser
225                 230                 235                 240

Glu Glu Thr Gly Thr Gly Trp Leu Ala Trp Ser Trp Lys Gly Asn Ser
            245                 250                 255

Thr Glu Trp Asp Tyr Leu Asp Leu Ser Glu Asp Trp Ala Gly Gln His
            260                 265                 270

Leu Thr Asp Trp Gly Asn Arg Ile Val His Gly Ala Asp Gly Leu Gln
            275                 280                 285

Glu Thr Ser Lys Pro Ser Thr Val Phe Ser Asp Asn Gly Gly Ser
            290                 295                 300

Pro Glu Pro Pro Thr Ala Thr Thr Leu Tyr Asp Phe Glu Gly Ser Thr
305                 310                 315                 320

Gln Gly Trp His Gly Ser Asn Val Ala Gly Gly Pro Trp Ser Val Thr
            325                 330                 335

Glu Trp Gly Thr Ser Gly Asn Tyr Ser Leu Lys Ala Asp Val Asn Leu
            340                 345                 350

Thr Ser Asn Ser Ser His Glu Leu Tyr Ser Glu Gln Ser Arg Asn Leu
            355                 360                 365

His Gly Tyr Ser Gln Leu Asn Ala Thr Val Arg His Ala Asn Trp Gly
            370                 375                 380

Asn His Gly Asn Gly Met Asn Ala Arg Leu Tyr Val Lys Thr Gly Ser
385                 390                 395                 400

Asp Tyr Thr Trp Tyr Ser Gly Pro Phe Thr Arg Ile Asn Ser Ser Asn
            405                 410                 415

Ser Gly Thr Thr Leu Ser Phe Asp Leu Asn Asn Ile Glu Asn Ser His
            420                 425                 430

His Val Arg Glu Ile Gly Val Gln Phe Ser Ala Ala Asp Asn Ser Ser
            435                 440                 445

Gly Gln Thr Ala Leu Tyr Val Asp Asn Val Thr Leu Arg
450                 455                 460

<210> SEQ ID NO 4
<211> LENGTH: 384
<212> TYPE: PRT
<213> ORGANISM: Streptomyces coelicolor strain A3
<220> FEATURE:
<221> NAME/KEY: misc_feature
<223> OTHER INFORMATION: Polypeptide sequence of "ScoMan1'" herein from
      Streptomyces coelicolor strain A3

<400> SEQUENCE: 4

```
Met Arg Lys Pro Arg Ser Thr Leu Ile Thr Thr Ala Gly Met Ala Phe
1               5                   10                  15

Ala Ala Val Leu Gly Leu Leu Phe Ala Leu Ala Gly Pro Ser Ala Gly
            20                  25                  30

Arg Ala Glu Ala Ala Ala Gly Gly Ile His Val Ser Asn Gly Arg Val
        35                  40                  45

Leu Glu Gly Asn Gly Ser Val Phe Val Met Arg Gly Val Asn His Ala
    50                  55                  60

Tyr Thr Trp Tyr Pro Asp Arg Thr Gly Ser Ile Ala Asp Ile Ala Ala
65                  70                  75                  80

Lys Gly Ala Asn Thr Val Arg Val Val Leu Ser Ser Gly Gly Arg Trp
                85                  90                  95

Thr Lys Thr Ser Ala Ser Glu Val Ser Ala Leu Ile Gly Gln Cys Lys
            100                 105                 110

Ala Asn Lys Val Ile Cys Val Leu Glu Val His Asp Thr Thr Gly Tyr
            115                 120                 125

Gly Glu Asp Gly Ala Ala Thr Ser Leu Asp Gln Ala Ala Asp Tyr Trp
    130                 135                 140

Val Ser Val Lys Ser Ala Leu Glu Gly Gln Glu Asp Tyr Val Val Val
145                 150                 155                 160

Asn Ile Gly Asn Glu Pro Phe Gly Asn Thr Asn Tyr Thr Ala Trp Thr
                165                 170                 175

Asp Ala Thr Lys Ser Ala Ile Gly Lys Leu Arg Gly Ala Gly Leu Asp
            180                 185                 190

His Ala Leu Met Val Asp Ala Pro Asn Trp Gly Gln Asp Trp Ser Gly
    195                 200                 205

Thr Met Arg Ser Asn Ala Ala Ser Val Phe Ala Ser Asp Pro Asp Arg
210                 215                 220

Asn Thr Val Phe Ser Val His Met Tyr Gly Val Tyr Asp Thr Ala Ala
225                 230                 235                 240

Glu Val Arg Asp Tyr Leu Asn Ala Phe Val Gly Ser Gly Leu Pro Ile
                245                 250                 255

Val Val Gly Glu Phe Gly Asp Gln His Ser Asp Gly Asn Pro Asp Glu
            260                 265                 270

Asp Ala Ile Met Ala Thr Ala Gln Ser Leu Gly Val Gly Tyr Leu Gly
            275                 280                 285

Trp Ser Trp Ser Gly Asn Gly Gly Val Glu Tyr Leu Asp Met Val
    290                 295                 300

Asn Gly Phe Asp Pro Asn Ser Leu Thr Ser Trp Gly Asn Arg Ile Phe
305                 310                 315                 320

Tyr Gly Ser Asn Gly Ile Ala Ala Thr Ser Arg Thr Ala Thr Val Tyr
                325                 330                 335

Gly Gly Gly Gly Ser Thr Gly Gly Thr Ala Pro Asn Gly Tyr Pro
            340                 345                 350

Tyr Cys Val Asn Gly Gly Ala Ser Asp Pro Asp Gly Asp Gly Trp Gly
            355                 360                 365

Trp Glu Asn Ser Arg Ser Cys Val Val Arg Gly Ser Ala Ala Asp His
370                 375                 380
```

<210> SEQ ID NO 5
<211> LENGTH: 694
<212> TYPE: PRT
<213> ORGANISM: Bacillus caldovelox
<220> FEATURE:
<221> NAME/KEY: misc_feature
<223> OTHER INFORMATION: Polypeptide sequence of "Bsp Man1" herein from
Bacillus caldovelox

<400> SEQUENCE: 5

```
Met Asn Lys Lys Trp Ser Tyr Thr Phe Ile Ala Leu Leu Val Ser Ile
1               5                   10                  15

Val Cys Ala Val Val Pro Ile Phe Phe Ser Gln Asn Asn Val His Ala
            20                  25                  30

Lys Thr Lys Arg Glu Pro Ala Thr Pro Thr Lys Asp Asn Glu Phe Val
        35                  40                  45

Tyr Arg Lys Gly Asp Lys Leu Met Ile Gly Asn Lys Glu Phe Arg Phe
    50                  55                  60

Val Gly Thr Asn Asn Tyr Tyr Leu His Tyr Lys Ser Asn Gln Met Ile
65                  70                  75                  80

Asp Asp Val Ile Glu Ser Ala Lys Lys Met Gly Ile Lys Val Ile Arg
                85                  90                  95

Leu Trp Gly Phe Phe Asp Gly Met Thr Ser Glu Asn Gln Ala His Asn
            100                 105                 110

Thr Tyr Met Gln Tyr Glu Met Gly Lys Tyr Met Gly Glu Gly Pro Ile
        115                 120                 125

Pro Lys Glu Leu Glu Gly Ala Gln Asn Gly Phe Glu Arg Leu Asp Tyr
    130                 135                 140

Thr Ile Tyr Lys Ala Lys Gln Glu Gly Ile Arg Leu Val Ile Val Leu
145                 150                 155                 160

Thr Asn Asn Trp Asn Asn Phe Gly Gly Met Met Gln Tyr Val Asn Trp
                165                 170                 175

Ile Gly Glu Thr Asn His Asp Leu Phe Tyr Thr Asp Glu Arg Ile Lys
            180                 185                 190

Thr Ala Tyr Lys Asn Tyr Val His Tyr Leu Ile Asn Arg Lys Asn Gln
        195                 200                 205

Tyr Thr Gly Ile Ile Tyr Lys Asn Glu Pro Thr Ile Met Ala Trp Glu
    210                 215                 220

Leu Ala Asn Glu Pro Arg Asn Asp Ser Asp Pro Thr Gly Asp Thr Leu
225                 230                 235                 240

Val Arg Trp Ala Asp Glu Met Ser Thr Tyr Ile Lys Ser Ile Asp Pro
                245                 250                 255

His His Leu Val Ala Val Gly Asp Glu Gly Phe Phe Arg Ser Ser
            260                 265                 270

Gly Gly Phe Asn Gly Glu Gly Ser Tyr Met Tyr Thr Gly Tyr Asn Gly
        275                 280                 285

Val Asp Trp Asp Arg Leu Ile Ala Leu Lys Asn Ile Asp Tyr Gly Thr
    290                 295                 300

Phe His Leu Tyr Pro Glu His Trp Gly Ile Ser Pro Glu Asn Val Glu
305                 310                 315                 320

Lys Trp Gly Glu Gln Tyr Ile Leu Asp His Leu Ala Ala Gly Lys Lys
                325                 330                 335

Ala Lys Lys Pro Val Val Leu Glu Glu Tyr Gly Ile Ser Ala Thr Gly
            340                 345                 350

Val Gln Asn Arg Glu Met Ile Tyr Asp Thr Trp Asn Arg Thr Met Phe
        355                 360                 365

Glu His Gly Gly Thr Gly Ala Met Phe Trp Leu Leu Thr Gly Ile Asp
    370                 375                 380

Asp Asn Pro Glu Ser Ala Asp Glu Asn Gly Tyr Tyr Pro Asp Tyr Asp
385                 390                 395                 400
```

-continued

```
Gly Phe Arg Ile Val Asn Asp His Ser Ser Val Thr Asn Leu Leu Lys
                405                 410                 415

Thr Tyr Ala Lys Leu Phe Asn Gly Asp Arg His Val Glu Lys Glu Pro
            420                 425                 430

Lys Val Tyr Phe Ala Phe Pro Ala Lys Pro Gln Asp Val Arg Gly Thr
        435                 440                 445

Tyr Arg Val Lys Val Lys Val Ala Ser Asp Gln His Lys Val Gln Lys
    450                 455                 460

Val Gln Leu Gln Leu Ser Ser His Asp Glu Ala Tyr Thr Met Lys Tyr
465                 470                 475                 480

Asn Ala Ser Phe Asp Tyr Glu Phe Asp Trp Asp Thr Thr Lys Glu
                485                 490                 495

Ile Glu Asp Ser Thr Val Thr Leu Lys Ala Thr Ala Thr Leu Thr Asn
                500                 505                 510

Lys Gln Thr Ile Ala Ser Asp Glu Val Thr Val Asn Ile Gln Asn Ala
            515                 520                 525

Ser Ala Tyr Glu Ile Ile Lys Gln Phe Ser Phe Asp Ser Asp Met Asn
        530                 535                 540

Asn Val Tyr Ala Asp Gly Thr Trp Gln Ala Asn Phe Gly Ile Pro Ala
545                 550                 555                 560

Ile Ser Thr Pro Lys Thr Arg Cys Leu Arg Val Asn Val Asp Leu Pro
                565                 570                 575

Gly Asn Ala Asp Trp Glu Glu Val Lys Val Lys Ile Ser Pro Ile Ser
            580                 585                 590

Glu Leu Ser Glu Thr Ser Arg Ile Ser Phe Asp Leu Leu Pro Arg
        595                 600                 605

Val Asp Val Asn Gly Ala Leu Arg Pro Tyr Ile Ala Leu Asn Pro Gly
    610                 615                 620

Trp Ile Lys Ile Gly Val Asp Gln Tyr His Val Asn Val Asn Asp Leu
625                 630                 635                 640

Thr Thr Val Thr Ile His Asn Gln Gln Tyr Lys Leu Leu His Val Asn
                645                 650                 655

Val Glu Phe Asn Ala Met Pro Asn Val Asn Glu Leu Phe Leu Asn Ile
            660                 665                 670

Val Gly Asn Lys Leu Ala Tyr Lys Gly Pro Ile Tyr Ile Asp Asn Val
        675                 680                 685

Thr Leu Phe Lys Lys Ile
    690

<210> SEQ ID NO 6
<211> LENGTH: 462
<212> TYPE: PRT
<213> ORGANISM: Micromonospora sp. strain L5
<220> FEATURE:
<221> NAME/KEY: misc_feature
<223> OTHER INFORMATION: Polypeptide sequence of "Msp Man2" herein from
      Micromonospora sp. strain L5

<400> SEQUENCE: 6

Met Lys Lys Leu Leu Ser Val Ala Gly Ala Leu Leu Thr Ala Leu
1               5                   10                  15

Ala Ala Val Phe Ala Leu Gly Gln Pro Ala His Ala Ala Thr Gly Phe
            20                  25                  30

Ser Val Ser Asn Gly Arg Leu Tyr Asp Ala Asn Gly Val Glu Phe Val
        35                  40                  45
```

```
Met Arg Gly Val Asn His Ala His Thr Trp Tyr Pro Gln Gln Thr Ser
     50                  55                  60
Ser Phe Ala Asn Ile Lys Ala Leu Gly Ala Asn Thr Val Arg Val Val
 65                  70                  75                  80
Leu Ser Ser Gly Asp Arg Trp Thr Lys Asn Ser Ala Ala Asp Val Ala
                 85                  90                  95
Asn Val Ile Ser Leu Cys Lys Ala Asn Arg Met Ile Cys Val Leu Glu
                100                 105                 110
Val His Asp Thr Thr Gly Tyr Gly Glu Asp Gly Ala Thr Thr Leu
             115                 120                 125
Ala Lys Ala Thr Asp Tyr Trp Leu Ser Ile Ala Asp Val Leu Lys Gly
        130                 135                 140
Gln Glu Lys Tyr Val Ile Val Asn Ile Gly Asn Glu Pro Phe Gly Asn
145                 150                 155                 160
Gln Gly Tyr Ser Ala Trp Thr Thr Asp Thr Ser Asn Ala Ile Lys Arg
                165                 170                 175
Leu Arg Ala Ala Gly Leu Thr His Thr Ile Met Val Asp Ala Pro Asn
                180                 185                 190
Trp Gly Gln Asp Trp Thr Phe Thr Met Arg Asp Asn Ala Gly Thr Val
                195                 200                 205
Phe Ala Ala Asp Pro Gln Arg Asn Thr Val Phe Ser Ile His Met Tyr
210                 215                 220
Gly Val Phe Asp Thr Ala Ala Glu Ile Ser Asp Tyr Leu Gly Arg Phe
225                 230                 235                 240
Arg Thr Ala Gly Leu Pro Ile Val Val Gly Glu Phe Gly Phe Asn His
                245                 250                 255
Ser Asp Gly Asn Pro Asp Glu Asp Ala Ile Met Ala Tyr Ala Gln Ala
                260                 265                 270
Asn Gly Ile Gly Tyr Leu Gly Trp Ser Trp Ser Gly Asn Gly Gly Gly
            275                 280                 285
Val Glu Tyr Leu Asp Met Thr Thr Ala Phe Asn Pro Ala Gln Leu Thr
            290                 295                 300
Ser Trp Gly Gln Arg Ile Phe Asn Gly Ala Asn Gly Ile Ala Ala Thr
305                 310                 315                 320
Ser Arg Glu Ala Ser Val Tyr Ala Gly Ser Thr Pro Thr Ala Ser Pro
                325                 330                 335
Thr Gly Ser Pro Thr Thr Ser Pro Thr Pro Thr Ser Ser Pro Ser Pro
                340                 345                 350
Thr Pro Pro Pro Thr Thr Thr Pro Pro Ser Gly Gly Cys Thr Ala
                355                 360                 365
Thr Tyr Thr Val Ala Asn Ser Trp Gln Gly Gly Phe Gln Gly Glu Val
            370                 375                 380
Lys Val Thr Ala Gly Ala Ala Ile Thr Gly Trp Thr Val Arg Trp
385                 390                 395                 400
Thr Phe Ala Asn Gly Gln Ser Val Thr Gln Ala Trp Asn Ala Ser Val
                405                 410                 415
Ser Asn Ser Gly Ser Ala Tyr Thr Ala Arg Asn Val Asp Tyr Asn Gly
                420                 425                 430
Arg Leu Gly Val Gly Ala Ser Thr Ser Phe Gly Phe Ile Gly Ser Trp
            435                 440                 445
Thr Gly Thr Asn Ser Thr Pro Ala Val Thr Cys Thr Ala Ser
450                 455                 460
```

<210> SEQ ID NO 7
<211> LENGTH: 46
<212> TYPE: DNA
<213> ORGANISM: Artificial Sequence
<220> FEATURE:
<223> OTHER INFORMATION: Synthetic: Primer1 (BssHII)

<400> SEQUENCE: 7
tgagcgcgca ggctgctgga aaaagttcag gcttttatgt tgatgg                46

<210> SEQ ID NO 8
<211> LENGTH: 39
<212> TYPE: DNA
<213> ORGANISM: Artificial Sequence
<220> FEATURE:
<223> OTHER INFORMATION: Synthetic: Primer 2 (BamHI)

<400> SEQUENCE: 8
cgcggatcct tatcttaaag taacattatc aacgtatag                         39

<210> SEQ ID NO 9
<211> LENGTH: 1479
<212> TYPE: DNA
<213> ORGANISM: Artificial Sequence
<220> FEATURE:
<223> OTHER INFORMATION: Synthetic: the confirmed nucleotide sequence of
      the bhe Man2 gene from the plasmid pML356

<400> SEQUENCE: 9
gtgagaagca aaaaattgtg gatcagcttg ttgtttgcgt taacgttaat ctttacgatg      60
gcgttcagca acatgagcgc gcaggctgct ggaaaaagtt caggcttta tgttgatggc     120 aatacgttat atgacgcaaa cgggcaacca tttgtcatga gaggtattaa ccatggacat     180
gcttggtata aagacaccgc ttcaacagct attcctgcca ttgcagagca aggcgccaac     240
acgatacgta ttgttttatc agatggcggt caatgggaaa aagacgacat tgacaccgtt     300
cgtgaagtta ttgagcttgc ggagcaaaat aaaatggtgg ctgtcgttga agttcatgat     360
gccacgggcc gcgattcgcg cagtgattta aatcgagccg ttgattattg gatagaaatg     420
aaagatgcgc ttatcggtaa agaagatacg gttattatta acattgcaaa cgagtggtat     480
gggagttggg atggctcagc ttgggccgat ggctatattg atgtcattcc gaagcttcgc     540
gatgccggct taacacacac cttaatggtt gatgcagcag gatggggca atatccgcaa     600 tctattcatg attacggaca agatgtgttt aatgcagatc cgttaaaaaa tacgatgttc     660
tccatccata tgtatgagta tgctggtggt gatgctaaca ctgttagatc aaatattgat     720
agagtcatag atcaagacct tgctctcgta ataggtgaat cggtcatag acatactgat     780 ggtgatgttg atgaagatac aatccttagt tattctgaag aaactggcac agggtggctc     840
gcttggtctt ggaaaggcaa cagtaccgaa tgggactatt tagacctttc agaagactgg     900
gctggtcaac atttaactga ttggggggaat agaattgtcc acggggccga tggcttacag     960
gaaacctcca aaccatccac cgtatttca gatgataacg gtggtagccc tgaaccgcca    1020
actgctacta ccttgtatga ctttgaagga agtacacaag gttggcatgg aagcaacgta    1080
gccggtggcc cttggtccgt aacagagtgg ggtacttcag gtaactactc tttaaaagcc    1140
gatgtaaatt taacctcaaa ttcttcacat gaactgtata gtgaacaaag tcgtaatcta    1200
cacggatact ctcagctcaa cgcaaccgtt cgccatgcca ttggggaaa tcacggtaat    1260 ggcatgaatg caagacttta cgtgaaaacg ggctctgatt acatggta tagccggtcct    1320 tttacacgta tcaatagctc caactcaggt acaacgttat cttttgattt aaacaacatc    1380

```
gaaaatagtc atcatgttag ggaaataggc gtgcaatttt cagcggcaga taatagcagc    1440
ggtcaaactg ctctatacgt tgataatgtt actttaaga                          1479
```

<210> SEQ ID NO 10
<211> LENGTH: 493
<212> TYPE: PRT
<213> ORGANISM: Artificial Sequence
<220> FEATURE:
<223> OTHER INFORMATION: Synthetic: the amino acid sequence of the Bhe
      Man2 full-length polypeptide expressed from the plasmid pML356

<400> SEQUENCE: 10

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ser Ser Gly Phe Tyr Val Asp Gly Asn Thr Leu Tyr Asp Ala Asn Gly
        35                  40                  45

Gln Pro Phe Val Met Arg Gly Ile Asn His Gly His Ala Trp Tyr Lys
    50                  55                  60

Asp Thr Ala Ser Thr Ala Ile Pro Ala Ile Ala Glu Gln Gly Ala Asn
65                  70                  75                  80

Thr Ile Arg Ile Val Leu Ser Asp Gly Gly Gln Trp Glu Lys Asp Asp
                85                  90                  95

Ile Asp Thr Val Arg Glu Val Ile Glu Leu Ala Glu Gln Asn Lys Met
            100                 105                 110

Val Ala Val Val Glu Val His Asp Ala Thr Gly Arg Asp Ser Arg Ser
        115                 120                 125

Asp Leu Asn Arg Ala Val Asp Tyr Trp Ile Glu Met Lys Asp Ala Leu
130                 135                 140

Ile Gly Lys Glu Asp Thr Val Ile Ile Asn Ile Ala Asn Glu Trp Tyr
145                 150                 155                 160

Gly Ser Trp Asp Gly Ser Ala Trp Ala Asp Gly Tyr Ile Asp Val Ile
                165                 170                 175

Pro Lys Leu Arg Asp Ala Gly Leu Thr His Thr Leu Met Val Asp Ala
            180                 185                 190

Ala Gly Trp Gly Gln Tyr Pro Gln Ser Ile His Asp Tyr Gly Gln Asp
        195                 200                 205

Val Phe Asn Ala Asp Pro Leu Lys Asn Thr Met Phe Ser Ile His Met
    210                 215                 220

Tyr Glu Tyr Ala Gly Gly Asp Ala Asn Thr Val Arg Ser Asn Ile Asp
225                 230                 235                 240

Arg Val Ile Asp Gln Asp Leu Ala Leu Val Ile Gly Glu Phe Gly His
                245                 250                 255

Arg His Thr Asp Gly Asp Val Asp Glu Asp Thr Ile Leu Ser Tyr Ser
            260                 265                 270

Glu Glu Thr Gly Thr Gly Trp Leu Ala Trp Ser Trp Lys Gly Asn Ser
        275                 280                 285

Thr Glu Trp Asp Tyr Leu Asp Leu Ser Glu Asp Trp Ala Gly Gln His
    290                 295                 300

Leu Thr Asp Trp Gly Asn Arg Ile Val His Gly Ala Asp Gly Leu Gln
305                 310                 315                 320

Glu Thr Ser Lys Pro Ser Thr Val Phe Ser Asp Asp Asn Gly Gly Ser
                325                 330                 335
```

-continued

```
Pro Glu Pro Pro Thr Ala Thr Thr Leu Tyr Asp Phe Glu Gly Ser Thr
            340                 345                 350

Gln Gly Trp His Gly Ser Asn Val Ala Gly Gly Pro Trp Ser Val Thr
        355                 360                 365

Glu Trp Gly Thr Ser Gly Asn Tyr Ser Leu Lys Ala Asp Val Asn Leu
    370                 375                 380

Thr Ser Asn Ser Ser His Glu Leu Tyr Ser Glu Gln Ser Arg Asn Leu
385                 390                 395                 400

His Gly Tyr Ser Gln Leu Asn Ala Thr Val Arg His Ala Asn Trp Gly
                405                 410                 415

Asn His Gly Asn Gly Met Asn Ala Arg Leu Tyr Val Lys Thr Gly Ser
            420                 425                 430

Asp Tyr Thr Trp Tyr Ser Gly Pro Phe Thr Arg Ile Asn Ser Ser Asn
        435                 440                 445

Ser Gly Thr Thr Leu Ser Phe Asp Leu Asn Asn Ile Glu Asn Ser His
    450                 455                 460

His Val Arg Glu Ile Gly Val Gln Phe Ser Ala Ala Asp Asn Ser Ser
465                 470                 475                 480

Gly Gln Thr Ala Leu Tyr Val Asp Asn Val Thr Leu Arg
                485                 490
```

<210> SEQ ID NO 11
<211> LENGTH: 464
<212> TYPE: PRT
<213> ORGANISM: Artificial Sequence
<220> FEATURE:
<223> OTHER INFORMATION: Synthetic: the amino acid sequence of the Bhe
      Man2 mature polypeptide expressed from the plasmid pML356

<400> SEQUENCE: 11

```
Ala Gly Lys Ser Ser Gly Phe Tyr Val Asp Gly Asn Thr Leu Tyr Asp
1               5                   10                  15

Ala Asn Gly Gln Pro Phe Val Met Arg Gly Ile Asn His Gly His Ala
            20                  25                  30

Trp Tyr Lys Asp Thr Ala Ser Thr Ala Ile Pro Ala Ile Ala Glu Gln
        35                  40                  45

Gly Ala Asn Thr Ile Arg Ile Val Leu Ser Asp Gly Gly Gln Trp Glu
    50                  55                  60

Lys Asp Asp Ile Asp Thr Val Arg Glu Val Ile Glu Leu Ala Glu Gln
65                  70                  75                  80

Asn Lys Met Val Ala Val Glu Val His Asp Ala Thr Gly Arg Asp
                85                  90                  95

Ser Arg Ser Asp Leu Asn Arg Ala Val Asp Tyr Trp Ile Glu Met Lys
            100                 105                 110

Asp Ala Leu Ile Gly Lys Glu Asp Thr Val Ile Ile Asn Ile Ala Asn
        115                 120                 125

Glu Trp Tyr Gly Ser Trp Asp Gly Ser Ala Trp Ala Asp Gly Tyr Ile
    130                 135                 140

Asp Val Ile Pro Lys Leu Arg Asp Ala Gly Leu Thr His Thr Leu Met
145                 150                 155                 160

Val Asp Ala Ala Gly Trp Gly Gln Tyr Pro Gln Ser Ile His Asp Tyr
                165                 170                 175

Gly Gln Asp Val Phe Asn Ala Asp Pro Leu Lys Asn Thr Met Phe Ser
            180                 185                 190

Ile His Met Tyr Glu Tyr Ala Gly Gly Asp Ala Asn Thr Val Arg Ser
        195                 200                 205
```

```
Asn Ile Asp Arg Val Ile Asp Gln Asp Leu Ala Leu Val Ile Gly Glu
            210                 215                 220

Phe Gly His Arg His Thr Asp Gly Asp Val Asp Glu Asp Thr Ile Leu
225                 230                 235                 240

Ser Tyr Ser Glu Glu Thr Gly Thr Gly Trp Leu Ala Trp Ser Trp Lys
                245                 250                 255

Gly Asn Ser Thr Glu Trp Asp Tyr Leu Asp Leu Ser Glu Asp Trp Ala
            260                 265                 270

Gly Gln His Leu Thr Asp Trp Gly Asn Arg Ile Val His Gly Ala Asp
        275                 280                 285

Gly Leu Gln Glu Thr Ser Lys Pro Ser Thr Val Phe Ser Asp Asp Asn
290                 295                 300

Gly Gly Ser Pro Glu Pro Pro Thr Ala Thr Thr Leu Tyr Asp Phe Glu
305                 310                 315                 320

Gly Ser Thr Gln Gly Trp His Gly Ser Asn Val Ala Gly Gly Pro Trp
                325                 330                 335

Ser Val Thr Glu Trp Gly Thr Ser Gly Asn Tyr Ser Leu Lys Ala Asp
            340                 345                 350

Val Asn Leu Thr Ser Asn Ser Ser His Glu Leu Tyr Ser Glu Gln Ser
        355                 360                 365

Arg Asn Leu His Gly Tyr Ser Gln Leu Asn Ala Thr Val Arg His Ala
370                 375                 380

Asn Trp Gly Asn His Gly Asn Gly Met Asn Ala Arg Leu Tyr Val Lys
385                 390                 395                 400

Thr Gly Ser Asp Tyr Thr Trp Tyr Ser Gly Pro Phe Thr Arg Ile Asn
                405                 410                 415

Ser Ser Asn Ser Gly Thr Thr Leu Ser Phe Asp Leu Asn Asn Ile Glu
            420                 425                 430

Asn Ser His His Val Arg Glu Ile Gly Val Gln Phe Ser Ala Ala Asp
        435                 440                 445

Asn Ser Ser Gly Gln Thr Ala Leu Tyr Val Asp Asn Val Thr Leu Arg
450                 455                 460
```

<210> SEQ ID NO 12
<211> LENGTH: 461
<212> TYPE: PRT
<213> ORGANISM: Artificial Sequence
<220> FEATURE:
<223> OTHER INFORMATION: Synthetic: the amino acid sequence of the Bhe
      Man2 mature polypeptide after the three-residue amino terminal
      extension were cleaved off from the predicted cleavage site

<400> SEQUENCE: 12

```
Ser Ser Gly Phe Tyr Val Asp Gly Asn Thr Leu Tyr Asp Ala Asn Gly
1               5                   10                  15

Gln Pro Phe Val Met Arg Gly Ile Asn His Gly His Ala Trp Tyr Lys
            20                  25                  30

Asp Thr Ala Ser Thr Ala Ile Pro Ala Ile Ala Glu Gln Gly Ala Asn
        35                  40                  45

Thr Ile Arg Ile Val Leu Ser Asp Gly Gly Gln Trp Glu Lys Asp Asp
50                  55                  60

Ile Asp Thr Val Arg Glu Val Ile Glu Leu Ala Glu Gln Asn Lys Met
65                  70                  75                  80

Val Ala Val Val Glu Val His Asp Ala Thr Gly Arg Asp Ser Arg Ser
                85                  90                  95
```

```
Asp Leu Asn Arg Ala Val Asp Tyr Trp Ile Glu Met Lys Asp Ala Leu
                100                 105                 110

Ile Gly Lys Glu Asp Thr Val Ile Ile Asn Ile Ala Asn Glu Trp Tyr
            115                 120                 125

Gly Ser Trp Asp Gly Ser Ala Trp Ala Asp Gly Tyr Ile Asp Val Ile
130                 135                 140

Pro Lys Leu Arg Asp Ala Gly Leu Thr His Thr Leu Met Val Asp Ala
145                 150                 155                 160

Ala Gly Trp Gly Gln Tyr Pro Gln Ser Ile His Asp Tyr Gly Gln Asp
                165                 170                 175

Val Phe Asn Ala Asp Pro Leu Lys Asn Thr Met Phe Ser Ile His Met
            180                 185                 190

Tyr Glu Tyr Ala Gly Gly Asp Ala Asn Thr Val Arg Ser Asn Ile Asp
        195                 200                 205

Arg Val Ile Asp Gln Asp Leu Ala Leu Val Ile Gly Glu Phe Gly His
        210                 215                 220

Arg His Thr Asp Gly Asp Val Asp Glu Asp Thr Ile Leu Ser Tyr Ser
225                 230                 235                 240

Glu Glu Thr Gly Thr Gly Trp Leu Ala Trp Ser Trp Lys Gly Asn Ser
                245                 250                 255

Thr Glu Trp Asp Tyr Leu Asp Leu Ser Glu Asp Trp Ala Gly Gln His
            260                 265                 270

Leu Thr Asp Trp Gly Asn Arg Ile Val His Gly Ala Asp Gly Leu Gln
        275                 280                 285

Glu Thr Ser Lys Pro Ser Thr Val Phe Ser Asp Asn Gly Gly Ser
290                 295                 300

Pro Glu Pro Pro Thr Ala Thr Thr Leu Tyr Asp Phe Glu Gly Ser Thr
305                 310                 315                 320

Gln Gly Trp His Gly Ser Asn Val Ala Gly Gly Pro Trp Ser Val Thr
                325                 330                 335

Glu Trp Gly Thr Ser Gly Asn Tyr Ser Leu Lys Ala Asp Val Asn Leu
            340                 345                 350

Thr Ser Asn Ser Ser His Glu Leu Tyr Ser Glu Gln Ser Arg Asn Leu
        355                 360                 365

His Gly Tyr Ser Gln Leu Asn Ala Thr Val Arg His Ala Asn Trp Gly
    370                 375                 380

Asn His Gly Asn Gly Met Asn Ala Arg Leu Tyr Val Lys Thr Gly Ser
385                 390                 395                 400

Asp Tyr Thr Trp Tyr Ser Gly Pro Phe Thr Arg Ile Asn Ser Ser Asn
                405                 410                 415

Ser Gly Thr Thr Leu Ser Phe Asp Leu Asn Asn Ile Glu Asn Ser His
            420                 425                 430

His Val Arg Glu Ile Gly Val Gln Phe Ser Ala Ala Asp Asn Ser Ser
        435                 440                 445

Gly Gln Thr Ala Leu Tyr Val Asp Asn Val Thr Leu Arg
    450                 455                 460

<210> SEQ ID NO 13
<211> LENGTH: 29
<212> TYPE: PRT
<213> ORGANISM: Artificial Sequence
<220> FEATURE:
<223> OTHER INFORMATION: Synthetic: the aprE signal polypeptide sequence
      for expression of Bhe Man2 polypeptides in B. subtilis

<400> SEQUENCE: 13
```

-continued

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 14
<211> LENGTH: 32
<212> TYPE: PRT
<213> ORGANISM: Artificial Sequence
<220> FEATURE:
<223> OTHER INFORMATION: Synthetic: a xylanase signal sequence that may
      be used for expression of Bhe Man2 polypeptides in Trichoderma
      reesei

<400> SEQUENCE: 14

Met Val Ser Phe Thr Ser Leu Leu Ala Ala Ser Pro Pro Ser Arg Ala
1               5                   10                  15

Ser Cys Arg Pro Ala Ala Glu Val Glu Ser Val Ala Val Glu Lys Arg
            20                  25                  30

<210> SEQ ID NO 15
<211> LENGTH: 16
<212> TYPE: PRT
<213> ORGANISM: Artificial Sequence
<220> FEATURE:
<223> OTHER INFORMATION: Synthetic: another xylanase signal sequence
      that may be used for expression of Bhe Man2 polypeptides in
      Trichoderma reesei

<400> SEQUENCE: 15

Met Lys Ala Asn Val Ile Leu Cys Leu Leu Ala Pro Leu Val Ala Ala
1               5                   10                  15

<210> SEQ ID NO 16
<211> LENGTH: 19
<212> TYPE: PRT
<213> ORGANISM: Artificial Sequence
<220> FEATURE:
<223> OTHER INFORMATION: Synthetic: a beta-glucosidase signal sequence
      that may be used for expression of Bhe Man2 polypeptides in
      Trichoderma reesei

<400> SEQUENCE: 16

Met Arg Tyr Arg Thr Ala Ala Ala Leu Ala Leu Ala Thr Gly Pro Phe
1               5                   10                  15

Ala Arg Ala

<210> SEQ ID NO 17
<211> LENGTH: 18
<212> TYPE: PRT
<213> ORGANISM: Artificial Sequence
<220> FEATURE:
<223> OTHER INFORMATION: Synthetic: a cellobiohydrolase signal sequence
      that may be used for expression of Bhe Man2 polypeptides in
      Trichoderma reesei

<400> SEQUENCE: 17

Met Ile Val Gly Ile Leu Thr Thr Leu Ala Thr Leu Ala Thr Leu Ala
1               5                   10                  15

Ala Ser

<210> SEQ ID NO 18
<211> LENGTH: 17
<212> TYPE: PRT
<213> ORGANISM: Artificial Sequence
```

```
<220> FEATURE:
<223> OTHER INFORMATION: Synthetic: a cellobiohydrolase signal sequence
      that may be used for expression of Bhe Man2 polypeptides in
      Trichoderma reesei

<400> SEQUENCE: 18

Met Tyr Arg Lys Leu Ala Val Ile Ser Ala Phe Leu Ala Thr Ala Arg
1               5                   10                  15

Ala

<210> SEQ ID NO 19
<211> LENGTH: 23
<212> TYPE: PRT
<213> ORGANISM: Artificial Sequence
<220> FEATURE:
<223> OTHER INFORMATION: Synthetic: an Fv3A signal sequence that may be
      used for expression of Bhe Man2 polypeptides in Fusarium
      verticillioides

<400> SEQUENCE: 19

Met Leu Leu Asn Leu Gln Val Ala Ala Ser Ala Leu Ser Leu Ser Leu
1               5                   10                  15

Leu Gly Gly Leu Ala Glu Ala
            20

<210> SEQ ID NO 20
<211> LENGTH: 19
<212> TYPE: PRT
<213> ORGANISM: Artificial Sequence
<220> FEATURE:
<223> OTHER INFORMATION: Synthetic: an Fv3C signal sequence that may be
      used for expression of Bhe Man2 polypeptides in Fusarium
      verticillioides

<400> SEQUENCE: 20

Met Lys Leu Asn Trp Val Ala Ala Ala Leu Ser Ile Gly Ala Ala Gly
1               5                   10                  15

Thr Asp Ser

<210> SEQ ID NO 21
<211> LENGTH: 19
<212> TYPE: PRT
<213> ORGANISM: Artificial Sequence
<220> FEATURE:
<223> OTHER INFORMATION: Synthetic: an Fv3D signal sequence that may be
      used for expression of Bhe Man2 polypeptides in Fusarium
      verticillioides

<400> SEQUENCE: 21

Met Ala Ser Ile Arg Ser Val Leu Val Ser Gly Leu Leu Ala Ala Gly
1               5                   10                  15

Val Asn Ala

<210> SEQ ID NO 22
<211> LENGTH: 22
<212> TYPE: PRT
<213> ORGANISM: Artificial Sequence
<220> FEATURE:
<223> OTHER INFORMATION: Synthetic: an Fv43A signal sequence that may be
      used for expression of Bhe Man2 polypeptides in Fusarium
      verticillioides

<400> SEQUENCE: 22

Met Trp Leu Thr Ser Pro Leu Leu Phe Ala Ser Thr Leu Leu Gly Leu
1               5                   10                  15
```

Thr Gly Val Ala Leu Ala
            20

<210> SEQ ID NO 23
<211> LENGTH: 16
<212> TYPE: PRT
<213> ORGANISM: Artificial Sequence
<220> FEATURE:
<223> OTHER INFORMATION: Synthetic: an Fv43B signal sequence that may be
      used for expression of Bhe Man2 polypeptides in Fusarium
      verticillioides

<400> SEQUENCE: 23

Met Arg Phe Ser Trp Leu Leu Cys Pro Leu Leu Ala Met Gly Ser Ala
1               5                   10                  15

<210> SEQ ID NO 24
<211> LENGTH: 22
<212> TYPE: PRT
<213> ORGANISM: Artificial Sequence
<220> FEATURE:
<223> OTHER INFORMATION: Synthetic: an Fv43C signal sequence that may be
      used for expression of Bhe Man2 polypeptides in Fusarium
      verticillioides

<400> SEQUENCE: 24

Met Arg Leu Leu Ser Phe Pro Ser His Leu Leu Val Ala Phe Leu Thr
1               5                   10                  15

Leu Lys Glu Ala Ser Ser
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic: an Fv43D signal sequence that may be
      used for expression of Bhe Man2 polypeptides in Fusarium
      verticillioides

<400> SEQUENCE: 25

Met Gln Leu Lys Phe Leu Ser Ser Ala Leu Leu Leu Ser Leu Thr Gly
1               5                   10                  15

Asn Cys Ala Ala
            20

<210> SEQ ID NO 26
<211> LENGTH: 18
<212> TYPE: PRT
<213> ORGANISM: Artificial Sequence
<220> FEATURE:
<223> OTHER INFORMATION: Synthetic: an Fv43E signal sequence that may be
      used for expression of Bhe Man2 polypeptides in Fusarium
      verticillioides

<400> SEQUENCE: 26

Met Lys Val Tyr Trp Leu Val Ala Trp Ala Thr Ser Leu Thr Pro Ala
1               5                   10                  15

Leu Ala

<210> SEQ ID NO 27
<211> LENGTH: 19
<212> TYPE: PRT
<213> ORGANISM: Artificial Sequence
<220> FEATURE:
<223> OTHER INFORMATION: Synthetic: an Fv51A signal sequence that may be
      used for expression of Bhe Man2 polypeptides in Fusarium verticillioides

<400> SEQUENCE: 27

Met Val Arg Phe Ser Ser Ile Leu Ala Ala Ala Ala Cys Phe Val Ala
1               5                   10                  15

Val Glu Ser

<210> SEQ ID NO 28
<211> LENGTH: 20
<212> TYPE: PRT
<213> ORGANISM: Artificial Sequence
<220> FEATURE:
<223> OTHER INFORMATION: Synthetic: a Pa51A signal sequence that may be
      used for expression of Bhe Man2 polypeptides in Podospora anserina

<400> SEQUENCE: 28

Met Ile His Leu Lys Pro Ala Leu Ala Ala Leu Leu Ala Leu Ser Thr
1               5                   10                  15

Gln Cys Val Ala
            20

<210> SEQ ID NO 29
<211> LENGTH: 17
<212> TYPE: PRT
<213> ORGANISM: Artificial Sequence
<220> FEATURE:
<223> OTHER INFORMATION: Synthetic: a Pa3D signal sequence that may be
      used for expression of Bhe Man2 polypeptides in Podospora anserina

<400> SEQUENCE: 29

Met Ala Leu Gln Thr Phe Phe Leu Leu Ala Ala Ala Met Leu Ala Asn
1               5                   10                  15

Ala

<210> SEQ ID NO 30
<211> LENGTH: 19
<212> TYPE: PRT
<213> ORGANISM: Artificial Sequence
<220> FEATURE:
<223> OTHER INFORMATION: Synthetic: a Pa3G signal sequence that may be
      used for expression of Bhe Man2 polypeptides in Podospora anserina

<400> SEQUENCE: 30

Met Lys Leu Asn Lys Pro Phe Leu Ala Ile Tyr Leu Ala Phe Asn Leu
1               5                   10                  15

Ala Glu Ala

<210> SEQ ID NO 31
<211> LENGTH: 20
<212> TYPE: PRT
<213> ORGANISM: Artificial Sequence
<220> FEATURE:
<223> OTHER INFORMATION: Synthetic: a Cg51B signal sequence that may be
      used for expression of Bhe Man2 polypeptides in Chaetomium
      globosum

<400> SEQUENCE: 31

Met Ala Pro Leu Ser Leu Arg Ala Leu Ser Leu Leu Ala Leu Thr Gly
1               5                   10                  15

Ala Ala Ala Ala
            20

<210> SEQ ID NO 32
<211> LENGTH: 19

```
<212> TYPE: PRT
<213> ORGANISM: Artificial Sequence
<220> FEATURE:
<223> OTHER INFORMATION: Synthetic: a xylanase signal sequence that may
      be used for expression of Bhe Man2 polypeptides in Thermoascus
      aurantiacus

<400> SEQUENCE: 32

Met Val Arg Pro Thr Ile Leu Leu Thr Ser Leu Leu Ala Pro Phe
1               5                   10                  15

Ala Ala Ala

<210> SEQ ID NO 33
<211> LENGTH: 21
<212> TYPE: PRT
<213> ORGANISM: Artificial Sequence
<220> FEATURE:
<223> OTHER INFORMATION: Synthetic: an At10A signal sequence that may be
      used for expression of Bhe Man2 polypeptides in Aspergillus
      terreus

<400> SEQUENCE: 33

Met His Met His Ser Leu Val Ala Ala Leu Ala Ala Gly Thr Leu Pro
1               5                   10                  15

Leu Leu Ala Ser Ala
            20

<210> SEQ ID NO 34
<211> LENGTH: 19
<212> TYPE: PRT
<213> ORGANISM: Artificial Sequence
<220> FEATURE:
<223> OTHER INFORMATION: Synthetic: an Af10A signal sequence that may
      be used for expression of Bhe Man2 polypeptides in Aspergillus
      fumigatus

<400> SEQUENCE: 34

Met Val His Leu Ser Ser Leu Ala Ala Ala Leu Ala Ala Leu Pro Leu
1               5                   10                  15

Val Tyr Gly

<210> SEQ ID NO 35
<211> LENGTH: 17
<212> TYPE: PRT
<213> ORGANISM: Artificial Sequence
<220> FEATURE:
<223> OTHER INFORMATION: Synthetic: an Af10B signal sequence that may be
      used for expression of Bhe Man2 polypeptides in Aspergillus
      fumigatus

<400> SEQUENCE: 35

Met Arg Phe Ser Leu Ala Ala Thr Thr Leu Leu Ala Gly Leu Ala Thr
1               5                   10                  15

Ala

<210> SEQ ID NO 36
<211> LENGTH: 19
<212> TYPE: PRT
<213> ORGANISM: Artificial Sequence
<220> FEATURE:
<223> OTHER INFORMATION: Synthetic: an Af10C signal sequence that may be
      used for expression of Bhe Man2 polypeptides in Aspergillus
      fumigatus

<400> SEQUENCE: 36

Met Val Val Leu Ser Lys Leu Val Ser Ser Ile Leu Phe Ala Ser Leu
```

```
1               5                   10                  15
Val Ser Ala

<210> SEQ ID NO 37
<211> LENGTH: 19
<212> TYPE: PRT
<213> ORGANISM: Artificial Sequence
<220> FEATURE:
<223> OTHER INFORMATION: Synthetic: an Ak10A signal sequence that may be
      used for expression of Bhe Man2 polypeptides in Aspergillus
      kawachii

<400> SEQUENCE: 37

Met Val Gln Ile Lys Ala Ala Ala Leu Ala Met Leu Phe Ala Ser His
1               5                   10                  15

Val Leu Ser

<210> SEQ ID NO 38
<211> LENGTH: 17
<212> TYPE: PRT
<213> ORGANISM: Artificial Sequence
<220> FEATURE:
<223> OTHER INFORMATION: Synthetic: a xylanase signal sequence that may
      be used to express Bhe Man2 polypeptides in Magnaporthe grisea

<400> SEQUENCE: 38

Met Lys Ala Ser Ser Val Leu Leu Gly Leu Ala Pro Leu Ala Ala Leu
1               5                   10                  15

Ala

<210> SEQ ID NO 39
<211> LENGTH: 19
<212> TYPE: PRT
<213> ORGANISM: Artificial Sequence
<220> FEATURE:
<223> OTHER INFORMATION: Synthetic: a mf(alpha) signal sequence that may
      be used to express Bhe Man2 polypeptides in yeast

<400> SEQUENCE: 39

Met Arg Phe Pro Ser Ile Phe Thr Ala Val Leu Phe Ala Ala Ser Ser
1               5                   10                  15

Ala Leu Ala

<210> SEQ ID NO 40
<211> LENGTH: 85
<212> TYPE: PRT
<213> ORGANISM: Artificial Sequence
<220> FEATURE:
<223> OTHER INFORMATION: Synthetic: a mf(alpha) pre-pro signal sequence
      that may be used to express Bhe Man2 polypeptides in yeast

<400> SEQUENCE: 40

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80
```

```
Ser Leu Asp Lys Arg
            85

<210> SEQ ID NO 41
<211> LENGTH: 20
<212> TYPE: PRT
<213> ORGANISM: Artificial Sequence
<220> FEATURE:
<223> OTHER INFORMATION: Synthetic: a suc2 signal sequence that may be
      used to express Bhe Man2 polypeptides in yeast

<400> SEQUENCE: 41

Met Leu Leu Gln Ala Phe Leu Phe Leu Leu Ala Gly Phe Ala Ala Lys
1               5                   10                  15

Ile Ser Ala Arg
            20
```

POLYPEPTIDES HAVING BETA-MANNANASE ACTIVITY AND METHODS OF USE

CROSS-REFERENCE TO RELATED APPLICATIONS

This application is the National Stage application of international application no. PCT/US2013/072589, filed on 2 Dec. 2013, which claims benefit of priority from international patent application PCT/CN2012/086181 filed on 7 Dec. 2012, both of which are incorporated herein by reference in their entireties.

SEQUENCE LISTING

The content of the electronically submitted sequence listing in ASCII text (File Name: NB40364USPCT_SeqList_ST25 Size: 52,100 bytes, and date of creation Dec. 9, 2015) is incorporated herein by reference in its entirety.

TECHNICAL FIELD

The present compositions and methods relates to a beta-mannanase derived from *Bacillus hemicellulosilyticus*, polynucleotides encoding the beta-mannanase, and methods for the production and use thereof. Formulations containing the recombinant beta-mannanase have a wide variety of uses, for instance, in hydrolyzing certain soft-wood type lignocellulosic materials and/or lignocellulosic biomass substrates comprising galactoglucomannan (GGM) and/or glucomannan (GM).

BACKGROUND

Cellulose and hemicellulose are the most abundant plant materials produced by photosynthesis. They can be degraded and used as an energy source by numerous microorganisms (e.g., bacteria, yeast and fungi) that produce extracellular enzymes capable of hydrolysis of the polymeric substrates to monomeric sugars (Aro et al., (2001) *J. Biol. Chem.*, 276: 24309-24314). As the limits of non-renewable resources approach, the potential of cellulose to become a major renewable energy resource is enormous (Krishna et al., (2001) *Bioresource Tech.*, 77: 193-196). The effective utilization of cellulose through biological processes is one approach to overcoming the shortage of foods, feeds, and fuels (Ohmiya et al., (1997) *Biotechnol. Gen. Engineer Rev.*, 14: 365-414).

Most of the enzymatic hydrolysis of lignocellulosic biomass materials focus on cellulases, which are enzymes that hydrolyze cellulose (comprising beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG") (Knowles et al., (1987) *TIBTECH* 5: 255-261; and Schulein, (1988) *Methods Enzymol.*, 160: 234-243). Endoglucanases act mainly on the amorphous parts of the cellulose fiber, whereas cellobiohydrolases are also able to degrade crystalline cellulose (Nevalainen and Penttila, (1995) *Mycota*, 303-319). Thus, the presence of a cellobiohydrolase in a cellulase system is required for efficient solubilization of crystalline cellulose (Suurnakki et al., (2000) *Cellulose*, 7: 189-209). Beta-glucosidase acts to liberate D-glucose units from cellobiose, cello-oligosaccharides, and other glucosides (Freer, (1993) *J. Biol. Chem.*, 268: 9337-9342).

In order to obtain useful fermentable sugars from lignocellulosic biomass materials, however, the lignin will typically first need to be permeabilized, for example, by various pretreatment methods, and the hemicellulose disrupted to allow access to the cellulose by the cellulases. Hemicelluloses have a complex chemical structure and their main chains are composed of mannans, xylans and galactans. Mannan-type polysaccharides are found in a variety of plants and plant tissues, for example, in seeds, roots, bulbs and tubers of plants. Such saccharides may include mannans, galactomannas and glucomannans, and they typically containing linear and interspersed chains of linear beta-1,4-linked mannose units and/or galactose units. Most types of mannans are not soluble in water, forming the hardness characteristic of certain plant tissues like palm kernels and ivory nuts. Galactomannas, on the other hand, tend to be water soluble and are found in the seed endosperm of leguminous plants, and are thought to help with retention of water in those seeds.

Enzymatic hydrolysis of the complex lignocellulosic structure and rather recalcitrant plant cell walls involves the concerted and/or tandem actions of a number of different endo-acting and exo-acting enzymes (e.g., cellulases and hemicellulases). Beta-xylanases and beta-mannanases are endo-acting enzymes, beta-mannosidase, beta-glucosidase and alpha-galactosidases are exo-acting enzymes. To disrupt the hemicellulose, xylanases together with other accessory proteins (non-limiting examples of which include L-α-arabinofuranosidases, feruloyl and acetylxylan esterases, glucuronidases, and β-xylosidases) can be applied.

Endo-1,4-beta-D-mannanases (E.C. 3.2.1.78) catalyzes the random hydrolysis of beta-1,4-mannosidic linkages in the main chain of mannan, galactomannanan, glucomannan, and galactoglucomannan, releasing short and long-chain oligomannosides. The short-chain oligomannosides may include mannobiose and mannotriose, although sometimes may also include some mannose. These can be further hydrolyzed by beta-mannosidases (E.C.3.2.1.25). In addition, the side-chain sugars of heteropolysaccharides can be further hydrolyzed, for example, to completion, by alpha galactosidase, beta-glucosidase, and/or by acetylmannan esterases. Puls J., (1997) *Macromol. Symp.* 120:183-196.

Beta-mannanases have been isolated from bacteria, fungi, plants and animals. See, Araujo A. et al., (1990) *J. App. Bacteriol.* 68:253-261; Dutta S. et al., (1997) *Plant Physiol.* 113:155-161; Puchar V. et al., (2004) *Biochim. Biophys. Acta* 1674:239-250. Genes encoding these enzymes from a number of organisms have also been cloned and sequenced, many if not all have been classified also as members of glycosyl hydrolase (GH) family 5 or 26, based on their sequences. See, e.g., Bewley D. J., (1997) *Planta* 203:454-459; Halstead J. R. et al., (2000) *FEMS Microl. Lett.* 192:197-203; Xu B. et al., (2002) *Eur. J. Biochem.* 269: 1753-1760; Henrissat, B. (1991) *Biochem. J.* 280:309-316. Although most beta-mannanases are secreted by the organisms from which they are originated, some are known to be associated with the cells. From a given organism there may be more than one mannanases with different isoelectric points derived from different genes or different products of the same genes, which fact is thought to be an indication of the importance of these enzymes.

Beta-mannanases have been used in commercially applications in, for example, industries such as the paper and pulp industry, foodstuff and feed industry, pharmaceutical industry and energy industry. Lee J. T., et al., (2003) Poult. Sci. 82:1925-1931; McCutchen M. C., et al., (1996) *Biotechnol. Bioeng.* 52:332-339; Suurnakki A., et al., (1997) *Adv. Biochem. Eng. Biotechnol.*, 57:261-287. Depending on the microorganisms from which the mannanases are derived, however, different beta-mannanases may have different properties and activity profiles that may make them more suitable for one or more industrial applications but not for others. The hydrolysis of lignocellulosic biomass substrates, especially those from plant sources, is notoriously difficult, accordingly few if any mannanases that have been found to be useful in other industrial applications have been utilized to hydrolyze lignocellulosic materials.

Thus there exists a need to identify mannanases and/or compositions comprising such enzymes that are effective at and capable of, in conjunction with commercial, newly identified, or engineered cellulases and other hemicellulases, converting a wide variety of plant-based and/or other cellulosic or hemicellulosic materials into fermentable sugars with sufficient or improved efficacy, improved fermentable sugar yields, and/or improved capacity to act on a greater variety of cellulosic feedstock. The production of new mannanases using engineered microbes is also important and desirable because these are means through which enzymes can be cost-effectively made.

SUMMARY

One aspect of the present compositions and methods is the application or use of a highly active beta-mannanase isolated from the bacterial species *Bacillus hemicellulosilyticus* strain, to hydrolyze a lignocellulosic biomass substrate. The herein described sequence of SEQ ID NO:2 was first described as a result of sequencing a *Bacillus* sp. strain N16-5, and it was designated a beta-mannanase precursor. See, e.g., Ma Y. et al., (2004) *Extremophiles*8(6):447-454. To date neither this enzyme nor any close homolog of it has been used in or in aiding the hydrolysis of a lignocellulosic biomass material. Compositions comprising such a polypeptide or a variant thereof has not been prepared Moreover, compositions comprising such a polypeptide or a variant thereof plus one or more cellulases, one or more hemicellulases, or a combination of one or more cellulases and one or more hemicellulases have been prepared or used in industrial applications related to cellulosic biomass hydrolysis and conversion to soluble fermentable sugars.

Therefore an aspect of the present invention is the discovery that a recombinant Bhe Man2 polypeptides having at least 70% (e.g., at least 70%, at least 75%, at least 80%, at least 85%, at least 90%, at least 91%, at least 92%, at least 93%, at least 94%, at least 95%, at least 96%, at least 97%, at least 98%, at least 99%, or higher or higher) identity, preferably at least 95%, at least 96%, at least 97%, at least 98%, at least 99%, or 100% identity to SEQ ID NO:2, or to the mature sequence of SEQ ID NO:3, which is residues 33-493 of SEQ ID NO:2, have beta-mannanase activity. Another aspect of the present invention is the discovery that, when a recombinant polypeptide having at least 70% (e.g., at least 70%, at least 75%, at least 80%, at least 85%, at least 90%, at least 91%, at least 92%, at least 93%, at least 94%, at least 95%, at least 96%, at least 97%, at least 98%, at least 99%, or higher) identity to SEQ ID NO:2 or to the mature sequence of SEQ ID NO:3 is combined with one or more cellulases and/or one or more other hemicellulases, the recombinant polypeptide confers improved capacity to that composition or mixture for hydrolyzing lignocellulosic biomass substrates. Such improvements include, for example, one or more of the properties selected from: an increased glucan conversion, an increased glucose yield from a given biomass substrate, an increased xylan conversion, an increased xylose yield, an increased total soluble sugar yield from a given biomass substrate, a more rapid liquefaction of a given biomass substrate at a solids level, and a more rapid viscosity reduction of a biomass substrate at a solids level. Improvements also may include the surprising finding that such a polypeptide can be used to boost the cellulosic biomass conversion and hydrolysis when in combination with a cellulase mixture or composition, which optionally further comprises one or more other hemicellulase. The resulting mixture comprising the Bhe Man2 polypeptide has improved hydrolysis performance as compared to a counterpart mixture having all the other enzymes at the same concentrations/proportion/amounts, but without the Bhe Man2. In some embodiments, the Bhe Man2 polypeptides can substitute, for example, for up to about 20 wt. % (e.g., up to about 20 wt. %, up to about 18 wt. %, up to about 16 wt. %, up to about 14 wt. %, up to about 12 wt. %, up to about 10 wt. %, up to about 8 wt. %, up to about 5 wt. %, etc) of a cellulase mixture or composition, and the substituted composition when used to hydrolyze a given lignocellulosic biomass substrate will retain its capacity and hydrolysis performance, or even have improved hydrolysis (e.g., higher glucan and/or xylan conversion, higher production of total sugars, faster liquefaction, and/or improved viscosity reduction) than a un-substituted counterpart cellulase mixture or composition of otherwise the same enzyme composition and the same total protein.

An aspect of the present composition and methods pertains to a beta-mannanase polypeptide of glycosyl hydrolase family 5 derived from *Bacillus hemicellulosilyticus*, or suitable variants thereof having beta-mannanase activity, referred to herein as "Bhe Man2" or a "Bhe Man2 polypeptide," nucleic acids encoding the same, compositions comprising the same, and methods of producing and applying the beta-mannanase polypeptides and compositions comprising thereof in hydrolyzing or converting lignocellulosic biomass into soluble, fermentable sugars. Particularly suitable lignocellulosic biomass materials are those that contain galactoglucomannan (GGM) and/or glucomannan (GM). Such fermentable sugars can then be converted into cellulosic ethanol, fuels, and other biochemicals and useful products. In certain embodiments, the beta-mannanase polypeptides, when combined with an enzyme mixture comprising at least one cellulase or at least one other hemicellulase, or with an enzyme mixture comprising at least one cellulase and at least one other hemicellulase, resulted in an enzyme mixture that is capable of increased or enhanced capacity to hydrolyze a lignocellulosic biomass material, as compared to, for example, other beta-mannanases from various microbes, which have similar pH optimum and/or similar temperature optimum.

Such increased or enhanced capacity to hydrolyze a lignocellulosic biomass material is reflected, for example, in substantially increased production of not only total soluble sugars, but surprisingly also increased production of glucose (reflecting a higher glucan conversion) and/or increased production of xylose (reflecting a higher xylan conversion), produced by enzymatic hydrolysis of a given lignocellulosic biomass substrate pretreated in a certain way.

The increased or enhanced capacity to hydrolyze a lignocellulosic biomass material can also be reflected in the desirable capacity of such an enzyme composition to improve or accelerate liquefaction and/or reduce viscosity of the pretreated biomass material. Such a viscosity/liquefaction benefit is the most prominent if a high solids level of the biomass material is used as a substrate. The viscosity/liquefaction benefits are also substantial and important when the enzyme composition/mixture is used to break down or hydrolyze a woody biomass, which tends to be highly fibrous and recalcitrant, making for particularly viscous feedstocks.

The increased or enhanced capacity to hydrolyze a lignocellulosic biomass allows the substitution of up to about 20 wt. % (e.g., up to about 20 wt. %, up to about 18 wt. %, up to about 16 wt. %, up to about 14 wt. %, up to about 12 wt. %, up to about 10 wt. %, up to about 8 wt. %, up to about 5 wt. %, etc) of any given cellulase composition, which optionally comprises one or more other hemicellulases, with a Bhe Man2 polypeptide, thereby reducing the amount of cellulase composition and the enzymes therein used to hydrolyze a given substrate without sacrificing performance. Indeed, the hydrolysis performance may even be improved using the substituted composition. Reducing the amount of cellulase composition as well as the amount of enzymes therein required to hydrolyze or saccharify a lignocellulosic biomass result substantial cost-savings to produce a cellulosic sugar, which can then be made into ethanol or other down-stream valuable bio-chemicals and useful products.

Aspects of the present compositions and methods are drawn to beta-mannanase derived from *Bacillus hemicellulosilyticus* or suitable variants there, referred to herein as "Bhe Man2" or "Bhe Man2 polypeptides," nucleic acids encoding the same, and methods of producing and employing the beta-mannanase in various industrially useful applications, for example, in hydrolyzing or converting lignocellulosic biomass into soluble, fermentable sugars. Such fermentable sugars can then be converted into cellulosic ethanol, fuels, and other bio-chemicals and useful products. As demonstrated herein, Bhe Man2 polypeptides as well as compositions comprising Bhe Man2 polypeptides have improved performance, when combined with at least one cellulase and/or at least one other hemicellulase, in hydrolyzing lignocellulosic biomass substrates, especially those that contain at least some measurable levels of galactoglucomannan (GGM) and/or glucomannan (GM), as compared to other beta-mannanases from similar microorganisms having similar pH optimums and/or temperature optimums. The improved performance may be that the Bhe Man2 polypeptides and/or enzyme compositions comprising Bhe Man2 polypeptides produces increased amounts of total soluble sugars when used to hydrolyze a lignocellulosic biomass substrate, under suitable conditions for the enzymatic hydrolysis, when compared to other microbial beta-mannanases having similar pH optimums and/or temperature optimums. Surprisingly the Bhe Man2 polypeptides and/or the compositions comprising such polypeptides also have improved glucan conversion and/or improved xylan conversion, as compared to those other microbial beta-mannanases having similar pH optimums and/or temperature optimums. The improved performance may alternatively or also be that the Bhe Man2 polypeptides and/or enzyme compositions comprising Bhe Man2 polypeptides confer rapid viscosity reduction/liquefaction to the biomass substrate, such that the overall hydrolysis is improved in not only effectiveness but also efficiency.

In some embodiments, a Bhe Man2 polypeptide is applied together with, or in the presence of, one or more cellulases in an enzyme composition to hydrolyze or breakdown a suitable biomass substrate. The one or more cellulases may be, for example, one or more beta-glucosidases, cellobiohydrolases, and/or endoglucanases. For example, the enzyme composition may comprise a Bhe Man2 polypeptide, a beta-glucosidase, a cellobiohydrolase, and an endoglucanase. In some embodiments, at least one of the cellulases is heterologous to the Bhe Man2, in that at least one of the cellulases is not derived from a *Bacillus hemicellulosilyticus*. In some embodiments, at least two among the cellulases are heterologous from each other.

In some embodiments, a Bhe Man2 polypeptide is applied together with, or in the presence of, one or more other hemicellulases in an enzyme composition. The one or more other hemicellulases may be, for example, other mannanases, xylanases, beta-xylosidases, and/or L-arabinofuranosidases. In some embodiments, at least one of the other hemicellulases is heterologous to the Bhe Man2, in that at least one of the other hemicellulases, which may be selected from one or more other mannanases, xylanases, beta-xylosidases, and/or L-arabinofuranosidases, is not derived from a *Bacillus hemicellulosilyticus*. In certain embodiments, at least two of the other hemicellulases are heterologous to each other.

In further embodiments, the Bhe Man2 polypeptide is applied together with, or in the presence of, one or more cellulases and one or more other hemicellulases in an enzyme composition. For example, the enzyme composition comprises a Bhe Man2 polypeptide, no or one or two other mannanases, one or more cellobiohydrolases, one or more endoglucanases, one or more beta-glucosidases, no or one or more xylanases, no or one or more beta-xylosidases, and no or one or more L-arabinofuranosidases.

In some embodiments, a Bhe Man2 polypeptide is used to substitute up to about 20 wt. % (based on total weight of proteins in a composition) (e.g., up to about 20 wt. %, up to about 18 wt. %, up to about 16 wt. %, up to about 14 wt. %, up to about 12 wt. %, up to about 10 wt. %, up to about 8 wt. %, up to about 5 wt. %, etc) of an enzyme composition comprising one or more cellulases, optionally also one or more other non-Bhe Man2 hemicellulases. In some embodiments, the thus-substituted enzyme composition has similar or improved saccharification performance as the counterpart unsubstituted enzyme composition having no Bhe Man2 present but all the other cellulases and/or hemicellulases, as well as the same total weight of proteins in the composition. In some embodiments, the substituted enzyme composition can produce the same amount of glucose and/or xylose, or an about 5% higher amount of glucose and/or xylose, about 7% higher amount of glucose and/or xylose, about 10% higher amount of glucose and/or xylose, or an even greater amount of glucose and/or xylose from the same lignocellulosic biomass substrate, as compared to the un-substituted counterpart enzyme composition having no Bhe Man2 but all the other cellulases and/or hemicellulases, and comprising the same total weight of proteins in the composition. In some embodiments, when used to hydrolyze a given lignocellulosic biomass substrate at a given solids level, the substituted enzyme composition reduces the viscosity of the biomass substrate by the same extent or to a higher extent, when compared to the un-substituted counterpart enzyme composition comprising no Bhe Man2 but all the other cellulases and/or hemicellulases, and comprising the same total weight of proteins in the composition.

In certain embodiments, a Bhe Man2 polypeptide, or a composition comprising the Bhe Man2 polypeptide is applied to a lignocellulosic biomass substrate or a partially hydrolyzed lignocellulosic biomass substrate in the presence of an ethanologen microbe, which is capable of metabolizing the soluble fermentable sugars produced by the enzymatic hydrolysis of the lignocellulosic biomass substrate, and converting such sugars into ethanol, biochemicals or other useful materials. Such a process may be a strictly sequential process whereby the hydrolysis step occurs before the fermentation step. Such a process may, alternatively, be a hybrid process, whereby the hydrolysis step starts first but for a period overlaps the fermentation step, which starts later. Such a process may, in a further alternative, be a simultaneous hydrolysis and fermentation process, whereby the enzymatic hydrolysis of the biomass substrate occurs while the sugars produced from the enzymatic hydrolysis are fermented by the ethanologen.

The Bhe Man2 polypeptide, for example, may be a part of an enzyme composition, which is a whole broth product of an engineered microbe capable of expressing or over-expressing such a polypeptide under suitable conditions. In certain embodiments, the Bhe Man2 polypeptide may be genetically engineered to express in a bacterial host cell, for example, in *Escherichia, Bacillus, Lactobacillus, Pseudomonas,* or *Streptomyces*. In certain embodiments, the Bhe Man2 polypeptide may be genetically engineered to express in a fungal host cell, for example, in a host cell of any one of the filamentous forms of the subdivision *Eumycotina*. Thus suitable filamentous fungal host cells may include, without limitation, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes,* and *Trichoderma*.

The engineered microbe expressing or over-expressing the Bhe Man2 polypeptide may also express and/or secrete one or more or all of one or more cellulases and optionally also one or more other hemicellulases. The one or more cellulases may be selected from, for example, one or more endoglucanases, one or more beta-glucosidases, and/or one or more cellobiohydrolases. The one or more other hemicellulases may be selected from, for example, one or more other beta-mannanases, one or more Alpha-L-arabinofuranosidases, one or more xylanases, and/or one or more beta-xylosidases. The resulting enzyme mixture comprising the Bhe Man2 polypeptide is a "co-expressed enzyme mixture" for the purpose of this application.

In another embodiment, the engineered microbe expressing or over-expressing the Bhe Man2 polypeptide may be one that is different from the one or more other microbes expressing one or more of the cellulases and/or one or more of the other hemicellulases. The one or more cellulases may be selected from, for example, one or more endoglucanases, one or more beta-glucosidases, and/or one or more cellobiohydrolases. The one or more other hemicellulases may be selected from, for example, one or more other beta-mannanases, one or more Alpha-L-arabinofuranosidases, one or more xylanases, and/or one or more beta-xylosidases. Accordingly the Bhe Man2 polypeptide can be combined with one or more cellulases and/or one or more other hemicellulases to form an enzyme mixture/composition, which is a "physical mixture" or "admixture" of a Bhe Man2 polypeptide and other polypeptides. The improved capacity observable or achievable with the co-expressed enzyme mixture is also observable or achievable with the admixture comprising a Bhe Man2 polypeptide.

As demonstrated herein, Bhe Man2 polypeptides and compositions comprising Bhe Man2 polypeptides have improved efficacy at conditions under which saccharification and degradation of lignocellulosic biomass take place. The improved efficacy of an enzyme composition comprising a Bhe Man2 polypeptide is shown when its performance of hydrolyzing a given biomass substrate is compared to that of an otherwise comparable enzyme composition comprising certain other microbial beta-mannanases having similar pH optimums and/or temperature optimums. In certain embodiments, Bhe Man2 polypeptides of the compositions and methods herein have at least about 5% (for example, at least about 5%, at least about 7%, at least about 10%, at least about 12%, at least about 13%, at least about 14%, at least about 15%, or more) increased capacity to hydrolyze a given lignocellulosic biomass substrate, which has optionally been subject to pretreatment, as compared to a ScoMan1 polypeptide from *Streptomyces coelicolor* A3, comprising the amino acid sequence of SEQ ID NO:4, or Bsp Man1 polypeptide from *Bacillus caldovelox*, comprising the amino acid sequence of SEQ ID NO:5, or Msp Man2 polypeptide from *Micromonospora* sp. L5, comprising the amino acid sequence of SEQ ID NO:6. The performance of hydrolyzing a given biomass substrate can be measured using the amount of total soluble sugars produced from a given lignocellulosic biomass substrate under a given set of saccharification conditions. The performance of hydrolyzing a given biomass substrate can also be measured using the amount of glucose produced from a given lignocellulosic biomass substrate under a saccharification condition or the % glucan conversion from that biomass substrate. For example, % glucan conversion can be assessed using a method described in Example 9 (herein). As such, a Bhe Man2 polypeptide of the compositions and methods herein, when included in a given enzyme composition in a certain amount, confers at least a 5% increase (for example, a 5% increase, a 7% increase, a 10% increase, a 11% increase, a 12% increase, a 13% increase, a 14% increase, a 15% increase, or a higher percent increase) in % glucan conversion when it is a part of an enzyme composition as compared to the otherwise same enzyme composition comprising the same amount of ScoMan1, or the same amount of Bsp Man1, or the same amount of Msp Man2, under the same hydrolysis conditions. Alternatively or in addition, the performance of hydrolyzing a given biomass substrate can be measured using the amount of xylose produced from a given lignocellulosic biomass substrate under a saccharification condition or the % xylan conversion from that substrate. For example % xylan conversion can be assessed using a method described in Example 9 (herein). As such, a Bhe Man2 polypeptide of the compositions and methods herein, when included in a given enzyme composition in a certain amount, confers at least a 5% increase (for example, a 5% increase, a 7% increase, a 10% increase, a 11% increase, a 12% increase, a 13% increase, a 14% increase, a 15% increase, or a higher percent increase) in % xylan conversion when it is a part of an enzyme composition as compared to the otherwise same enzyme composition comprising the same amount of ScoMan1, or the same amount of Bsp Man1, or the same amount of Msp Man2, under the same hydrolysis conditions.

Furthermore, the performance of hydrolyzing a given biomass substrate can be measured by the extent or degree of liquefaction or viscosity reduction of the biomass substrate or the speed of such liquefaction or viscosity reduction of a given substrate having a particular solids level. The viscosity reduction and/or liquefaction and the rate thereof can be assessed using a method described in Example 10 (herein). As such a Bhe Man2 polypeptide of the compositions and methods herein, when included in a given enzyme composition in a certain amount, confers at least a 5% higher viscosity reduction or level of liquefaction as compared to an otherwise same enzyme composition comprising the same amount of ScoMan1, or the same amount of Bsp Man1, or the same amount of Msp Man2, under the same hydrolysis conditions and after the hydrolysis reaction is carried on for the same time period.

Aspects of the present compositions and methods include a recombinant polypeptide comprising an amino acid sequence that is at least 70% identical to the amino acid sequence of SEQ ID NO: 2, wherein the polypeptide has beta-mannanase activity. In some aspects, a Bhe Man2 polypeptide and/or as it is applied in an enzyme composition or in a method to hydrolyze a lignocellulosic biomass substrate is (a) derived from, obtainable from, or produced by *Bacillus hemicellulosilyticus*, for example, *Bacillus* sp., strain N16-5; (b) a recombinant polypeptide comprising an amino acid sequence that is at least 70% (e.g., 70%, 75%, 80%, 85%, 90%, 91%, 92%, 93%, 94%, 95%, 96%, 97%, 98%, 99%, or 100%) identical to the amino acid sequence of SEQ ID NO:2; (c) a recombinant polypeptide comprising an amino acid sequence that is at least 70% (e.g., at least 70%, 75%, 80%, 85%, 90%, 91%, 92%, 93%, 94%, 95%, 96%, 97%, 98%, 99%, or 100%) identical to the catalytic domain of SEQ ID NO:2, namely amino acid residues 33 to 493; (d) a recombinant polypeptide comprising an amino acid sequence that is at least 70% (e.g., at least 70%, 75%, 80%, 85%, 90%, 91%, 92%, 93%, 94%, 95%, 96%, 97%, 98%, 99%, or 100%) identical to the mature form of amino acid sequence of SEQ ID NO:3, namely amino acid residues 33-493 of SEQ ID NO:2; or (e) a fragment of (a), (b), (c) or (d) having beta-mannanase activity. In certain embodiments, it is provided a variant polypeptide having beta-mannanase activity, which comprises a substitution, a deletion and/or an insertion of one or more amino acid residues of SEQ ID NO:2 or SEQ ID NO:3. In certain embodiments, the polypeptide comprises an amino acid sequence that is at least 80% identical to the amino acid sequence of SEQ ID NO:2 or SEQ ID NO: 3. In certain embodiments, the polypeptide comprises an amino acid sequence that is at least 90% identical to the amino acid sequence of SEQ ID NO:2 or SEQ ID NO: 3. In certain embodiments, the polypeptide comprises an amino acid sequence that is at least 95% identical to the amino acid sequence of SEQ ID NO:2 or SEQ ID NO: 3. In certain embodiments, the polypeptide comprises an amino acid sequence that is at least 99% identical to the amino acid sequence of SEQ ID NO:2 or SEQ ID NO: 3.

In certain embodiments, the Bhe Man2 polypeptide has an optimum pH at about pH 8.0 to 9.0. In some embodiments, the Bhe Man2 polypeptide retains greater than 70% of maximum beta-mannanase activity between pH 6.0 and pH 9.0.

In certain embodiments, the Bhe Man2 polypeptide has an optimum temperature of about 64° C. In some embodiments, the Bhe Man2 polypeptide retains greater than 80% of its maximum beta-mannanase activity between the temperatures of 50° C. and 74° C.

In some embodiments, the Bhe Man2 polypeptide has good thermostability. For example, the Bhe Man2 polypeptide retains about 50% of the beta-mannanase activity when incubated for about 2 hours at a temperature of about 75° C. In certain embodiments, the polypeptides retains at least 95% of the beta-mannanase activity when incubated for about 2 hours at a temperature of lower than 55° C.

Aspects of the present compositions and methods include a composition comprising the recombinant Bhe Man2 polypeptide as described herein and one or more cellulases. In some embodiments, the one or more cellulases may be selected from one or more endoglucanases, one or more cellobiohydrolases and/or one or more beta-glucosidases.

Aspects of the present compositions and methods include a composition comprising the recombinant Bhe Man2 polypeptide as described herein and one or more hemicellulases. In some embodiments, the one or more other hemicellulases may be selected from one or more xylanases, beta-xylosidases, alpha-L-arabinofuranosidases and one or more other mannanases.

Aspects of the present compositions and methods include a composition comprising the recombinant Bhe Man2 polypeptide as described herein and one or more cellulases and one or more other hemicellulases. For example, the one or more cellulases may be selected from endoglucanases, cellobiohydrolases, and/or beta-glucosidases, and the one or more other hemicellulases may include xylanases, beta-xylosidases, alpha-L-arabinofuranosidases and other mannanases.

As demonstrated herein, the Bhe Man2 polypeptides described herein can impart, to an enzyme mixture or composition comprising a Bhe Man2 polypeptide in addition to one or more cellulases, an improved capacity to hydrolyze, saccharify, or degrade a given lignocellulosic biomass substrate, which has optionally been subject to pretreatment, and further optionally having had at least some of its xylan-containing components removed or separated from the glucan-containing components. Such improved capacity to hydrolyze, saccharify, or degrade a given lignocellulosic biomass substrate may be evidenced by a measurably higher % glucan conversion achieved using a given enzyme composition comprising at least one cellulase, and a Bhe Man2 polypeptide in an amount of as high as about 20 wt. % (for example, up to about 2 wt. %, up to about 5 wt. %, up to about 7 wt. %, up to about 10 wt. %, up to about 12 wt. %, up to about 15 wt. %, up to about 16 wt. %, up to about 17 wt. %, up to about 18 wt. %, up to about 19 wt. %, up to about 20 wt. %) of the enzyme composition, to hydrolyze a particular lignocellulosic biomass substrate, as compared to a counterpart enzyme composition comprising all the same other enzymes in the same proportion but comprising no Bhe Man2 polypeptide.

The Bhe Man2 polypeptides described herein can alternatively or additionally impart, to an enzyme mixture or composition comprising a Bhe Man2 polypeptide in addition to one or more other hemicellulases, an improved capacity to hydrolyze, saccharify, or degrade a given xylan-containing lignocellulosic biomass substrate, which has optionally been subject to pretreatment, and further optionally having at least had some of its xylan-containing components removed or separated from its glucan-containing components. Such improved capacity to hydrolyze, saccharify, or degrade a given lignocellulosic biomass substrate may be evidenced by a measurably higher % xylan conversion achieved using a given enzyme composition comprising at least one other hemicellulase, and a Bhe Man2 polypeptide in an amount of as high as about 20 wt. % (for example, up to about 2 wt. %, up to about 5 wt. %, up to about 7 wt. %, up to about 10 wt. %, up to about 12 wt. %, up to about 15 wt. %, up to about 16 wt. %, up to about 17 wt. %, up to about 18 wt. %, up to about 19 wt. %, up to about 20 wt. %) of the enzyme composition to hydrolyze a xylan-containing lignocellulosic biomass substrate or a xylan-containing component derived therefrom, as compared a counterpart enzyme composition comprising all the same other enzymes in the same proportion but comprising no Bhe Man2 polypeptide.

Aspects of the present compositions and methods include a composition comprising a recombinant Bhe Man2 polypeptide as detailed herein and a lignocellulosic biomass. Suitable lignocellulosic biomass may be, for example, derived from an agricultural crop, a byproduct of a food or feed production, a lignocellulosic waste product, a plant residue, including, for example, a grass residue, or a waste paper or waste paper product. Certain particularly suitable biomass may be one that comprises at least a measurable level of galactoglucomannan (GGM) and/or glucomannan (GM). Suitably the biomass may preferably be one that is rich in galactoglucomannan (GGM) and/or in glucomannan (GM), for example one that comprises at least about 0.5 wt. % (e.g., 0.5 wt. %, at least about 0.7 wt. %, at least about 1.0 wt. %, at least about 1.2 wt. %, at least about 1.5 wt. %, at least about 2.0 wt. %, at least about 2.5 wt. %, or more) GGM, or at least about 0.5 wt. % (e.g., 0.5 wt. %, at least about 0.7 wt. %, at least about 1.0 wt. %, at least about 1.2 wt. %, at least about 1.5 wt. %, at least about 2.0 wt. %, at least about 2.5 wt. %, or more) GM, or at least about 0.5 wt. % (e.g., 0.5 wt. %, at least about 0.7 wt. %, at least about 1.0 wt. %, at least about 1.2 wt. %, at least about 1.5 wt. %, at least about 2.0 wt. %, at least about 2.5 wt. %, at least about 3.0 wt. %, at least about 3.5 wt. %, at least about 4.0 wt. %, at least about 4.5 wt. %, at least about 5.0 wt. %, or more) of GGM and GM combined. In certain embodiments, the lignocellulosic biomass has been subject to one or more pretreatment steps in order to render xylan, hemicelluloses, cellulose and/or lignin material more accessible or susceptible to enzymes and thus more amendable to enzymatic hydrolysis. A suitable pretreatment method may be, for example, subjecting biomass material to a catalyst comprising a dilute solution of a strong acid and a metal salt in a reactor. See, e.g., U.S. Pat. Nos. 6,660,506, 6,423,145. Alternatively, a suitable pretreatment may be, for example, a multi-stepped process as described in U.S. Pat. No. 5,536,325. In certain embodiments, the biomass material may be subject to one or more stages of dilute acid hydrolysis using about 0.4% to about 2% of a strong acid, in accordance with the disclosures of U.S. Pat. No. 6,409,841. Further embodiments of pretreatment methods may include those described in, for example, U.S. Pat. No. 5,705,369; in Gould, (1984) Biotech. & Bioengr., 26:46-52; in Teixeira et al., (1999) Appl. Biochem & Biotech., 77-79:19-34; in International Published Patent Application WO2004/081185; or in U.S. Patent Publication No. 20070031918, or International Published Patent Application WO06110901. A non-limiting example of a suitable lignocellulosic biomass substrate is a softwood substrated pretreated using the US Department of Agriculture's SPORL protocol, as described in Example 10 herein. Another non-limiting example of a suitable lignocellulosic biomass substrate is an akaline KRAFT-pretreated softwood pulp FPP-27.

The present invention also pertains to isolated polynucleotides encoding polypeptides having beta-mannanase activity, wherein the isolated polynucleotides are selected from:
(1) a polynucleotide encoding a polypeptide comprising an amino acid sequence having at least 70% (e.g., 70%, 75%, 80%, 85%, 90%, 91%, 92%, 93%, 94%, 95%, 96%, 97%, 98%, 99%, or 100%) identity to SEQ ID NO:2 or to SEQ ID NO:3;
(2) a polynucleotide having at least 70% (e.g., at least 70%, 75%, 80%, 85%, 90%, 91%, 92%, 93%, 94%, 95%, 96%, 97%, 98%, 99%, or 100%) identity to SEQ ID NO:1, or hybridizes under medium stringency conditions, high stringency conditions, or very high stringency conditions to SEQ ID NO:1, or to a complementary sequence thereof.

Aspects of the present compositions and methods include methods of making or producing a Bhe Man2 polypeptide having beta-mannanase activity, employing an isolated nucleic acid sequence encoding the recombinant polypeptide comprising an amino acid sequence that is at least 70% identical (e.g., at least 70%, 75%, 80%, 85%, 90%, 91%, 92%, 93%, 94%, 95%, 96%, 97%, 98%, 99%, or 100%) to that of SEQ ID NO:2, or that of the mature sequence SEQ ID NO:3. In some embodiments, the polypeptide further comprises a native or non-native signal peptide such that the Bhe Man2 polypeptide that is produced is secreted by a host organism, for example, the signal peptide comprises a sequence that is at least 90% identical to any one of SEQ ID NOs:13-41 to allow for heterologous expression in a variety of fungal host cells, yeast host cells and bacterial host cells. In certain embodiments the isolated nucleic acid comprises a sequence that is at least 70% (e.g., at least 70%, 75%, 80%, 85%, 90%, 91%, 92%, 93%, 94%, 95%, 96%, 97%, 98%, 99%, or 100%) identical to SEQ ID NO:1. In certain embodiments, the isolated nucleic acid further comprises a nucleic acid sequence encoding a signal peptide sequence. In certain embodiments, the signal peptide sequence may be one selected from SEQ ID NOs:13-41. In certain particular embodiments, a nucleic acid sequence encoding the signal peptide sequence of SEQ ID NO:17 or 18 is used to express a Bhe Man2 polypeptide in *Trichoderma reesei*.

Aspects of the present compositions and methods include an expression vector comprising the isolated nucleic acid as described above in operable combination with a regulatory sequence.

Aspects of the present compositions and methods include a host cell comprising the expression vector. In certain embodiments, the host cell is a bacterial cell or a fungal cell.

Aspects of the present compositions and methods include a composition comprising the host cell described above and a culture medium. Aspects of the present compositions and methods include a method of producing a Bhe Man2 polypeptide comprising: culturing the host cell described above in a culture medium, under suitable conditions to produce the beta-mannanase.

Aspects of the present compositions and methods include a composition comprising a Bhe Man2 polypeptide in the supernatant of a culture medium produced in accordance with the methods for producing the beta-mannanase as described above.

In some aspects the present invention is related to nucleic acid constructs, recombinant expression vectors, engineered host cells comprising a polynucleotide encoding a polypeptide having beta-mannanase activity, as described above and herein. In further aspects, the present invention pertains to methods of preparing or producing the beta-mannanase polypeptides of the invention or compositions comprising such beta-mannanase polypeptides using the nucleic acid constructs, recombinant expression vectors, and/or engineered host cells. In particular, the present invention is related, for example, to a nucleic acid constructs comprising a suitable signal peptide operably linked to the mature sequence of the beta-mannanase that is at least 70% identical to SEQ ID NO:2 or to the mature sequence of SEQ ID NO:3, or is encoded by a polynucleotide that is at least 70% identical to SEQ ID NO:1, an isolated polynucleotide, a nucleic acid construct, a recombinant expression vector, or an engineered host cell comprising such a nucleic acid construct. In some embodiments, the signal peptide and beta-mannanase sequences are derived from different microorganisms.

Also provided is an expression vector comprising the isolated nucleic acid in operable combination with a regulatory sequence. Additionally, a host cell is provided comprising the expression vector. In still further embodiments, a composition is provided, which comprises the host cell and a culture medium.

In some embodiments, the host cell is a bacterial cell or a fungal cell.

In further embodiments, the Bhe Man2 polypeptide is heterologously expressed by a host cell. For example, the Bhe Man2 polypeptide is expressed by an engineered microorganism that is not *Bacillus hemicellulosilyticus*. In some embodiments, the Bhe Man2 polypeptide is co-expressed with one or more cellulase genes. In some embodiments, the Bhe Man2 polypeptide is co-expressed with one or more other hemicellulase genes.

In some aspects, compositions comprising the recombinant Bhe Man2 polypeptides of the preceding paragraphs and methods of preparing such compositions are provided. In some embodiments, the composition further comprises one or more cellulases, whereby the one or more cellulases are co-expressed by a host cell with the Bhe Man2 polypeptide. In other embodiments, compositions comprising the Bhe Man2 polypeptides may be an admixture of an isolated Bhe Man2 polypeptide, optionally purified, physically blended with one or more cellulases and/or other enzymes. For example, the one or more cellulases can be selected from no or one or more beta-glucosidases, one or more cellobiohydrolyases, and/or one or more endoglucanases. In certain specific embodiments, such beta-glucosidases, cellobiohydrolases and/or endoglucanases, if present, can be co-expressed with the Bhe Man2 polypeptide by a single host cell. In some embodiments, at least two of the two or more cellulases may be heterologous to each other or derived from different organisms. For example, the composition may comprise at least one beta-glucosidase and at least one cellobiohydrolase, whereby that beta-glucosidase and that cellobiohydrolase are not from the same microorganism. In some embodiments, one or more of the cellulases are endogenous to the host cell, but are overexpressed or expressed at a level that is different from that would otherwise be naturally-occurring in the host cell. For example, one or more of the cellulases may be a *Trichoderma reesei* CBH1 and/or CBH2, which are native to a *Trichoderma reesei* host cell, but either or both CBH1 and CBH2 are overexpressed or underexpressed when they are co-expressed in the *Trichoderma reesei* host cell with a Bhe Man2 polypeptide.

In certain embodiments, the composition comprising the recombinant Bhe Man2 polypeptide may further comprise one or more other hemicellulases, whereby the one or more other hemicellulases are co-expressed by a host cell with the Bhe Man2 polypeptide. For example, the one or more other hemicellulases can be selected from one or more other beta-mannanases, one or more xylanases, one or more beta-xylosidases, and/or one or more L-arabinofuranosidases. In certain embodiments, such other mannanases, xylanases, beta-xylosidases and L-arabinofuranosidases, if present, can be co-expressed with the Bhe Man2 polypeptide by a single host cell; or alternatively, one or more or all of such other mannanases, xylanases, beta-xylosidases and L-arabinofuranosidases, if present, are not co-expressed with the Bhe Man2 polypeptides in a single host cell, but are rather physically mixed or blended together to form an enzyme composition after the individual enzymes are produced by their respective host cells.

In further aspects, the composition comprising the recombinant Bhe Man2 polypeptide may further comprise one or more celluases and one or more other hemicelluases, whereby the one or more cellulases and/or one or more other hemicellulases are co-expressed by a host cell with the Bhe Man2 polypeptide. For example, a Bhe Man2 polypeptide may be co-expressed with one or more beta-glucosidases, one or more cellobiohydrolases, one or more endoglucanases, one or more endo-xylanases, one or more beta-xylosidases, and/or one or more L-arabinofuranosidases, in addition to other non-cellulase non-hemicellulase enzymes or proteins in the same host cell. Alternatively, the composition comprising the recombinant Bhe Man2 polypeptide comprising one or more cellulases and one or more other hemicelulases may be prepared by physically mixing the Bhe Man2 polypeptide with one or more cellulases and one or more other hemicellulases post production, whereby the Bhe Man2 polypeptide and the one or more cellulases and one or more other hemicellulases are produced from different host cells. Aspects of the present compositions and methods thus include a composition comprising the host cell described above co-expressing a number of enzymes in addition to the Bhe Man2 polypeptide and a culture medium. Alternatively, aspects of the present compositions and methods include a first composition comprising a first host cell expressing a Bhe Man2 polypeptide, optionally in addition to one or more other enzymes/proteins, and a second composition comprising a second host cell expressing, for example, one or more cellulases and/or one or more other hemicellulases, and optionally a third composition comprising a third host cell expressing, for example, one or more other cellulases and/or one or more other hemicellulases that are different from those that are expressed by the first and second host cells. Such first, second, and third compositions resulting from enzyme production from the host cells, if appropriate, can suitably be physically blended or mixed to form an admixture of enzymes that form the present composition. Also provided are compositions that comprise the Bhe Man2 polypeptide and the other enzymes produced in accordance with the methods herein in supernatant of a culture medium or culture media, as appropriate. Such supernatant of the culture medium can be used as is, with minimum or no post-production processing, which may typically include filtration to remove cell debris, cell-kill procedures, and/or ultrafiltration or other steps to enrich or concentrate the enzymes therein. Such supernatants are called "whole broths" or "whole cellulase broths" herein.

In further aspects, the present invention pertains to a method of applying or using the composition as described above under conditions suitable for degrading or converting a cellulosic material and for producing a substance from a cellulosic material.

In a further aspect, methods for degrading or converting a cellulosic material into fermentable sugars are provided, comprising: contacting the cellulosic material, preferably having already been subject to one or more pretreatment steps, with the Bhe Man2 polypeptides or the compositions comprising such polypeptides of one of the preceding paragraphs to yield fermentable sugars.

Accordingly the instant specification is drawn to the following particular aspects:

In a first aspect, an enzyme composition comprising a recombinant polypeptide comprising an amino acid sequence that is at least 70% identical to the amino acid sequence of SEQ ID NO:2 or SEQ ID NO:3, wherein the polypeptide has beta-mannanase activity, and one or more cellulases.

In a second aspect, the enzyme composition of the first aspect, wherein the recombinant polypeptide improves the hydrolysis performance of the enzyme composition when the recombinant polypeptide constitutes up to 20 wt. % of the enzyme composition, wherein the improved hydrolysis performance comprises:
(a) an increased % glucan conversion, an increased % xylan conversion, and/or an increased % glucan and % xylan conversion from a given lignocellulosic biomass substrate under the same hydrolysis conditions; or
(b) an at least about 5% faster viscosity reduction of a given lignocellulosic biomass substrate under the same hydrolysis conditions.

In a third aspect, the renzyme composition of the first or second aspect, wherein the recombinant polypeptide has an increased beta-mannanase activity as compared to the beta-mannanase activity of ScoMan1 comprising SEQ ID NO:4.

In a fourth aspect, the enzyme composition of the first or second aspect, wherein the recombinant polypeptide has an increased beta-mannanase activity as compared to the beta-mannanase activity of Bsp Man1 comprising SEQ ID NO:5.

In a fifth aspect, the enzyme composition of the first or second aspect, wherein the recombinant polypeptide has an increased beta-mannanase activity as compared to the beta-mannanase activity of Msp Man2 comprising SEQ ID NO:6.

In a sixth aspect, the enzyme composition of any one of the first to fifth aspects, wherein the recombinant polypeptide retains greater than 70% of the beta-mannanase activity when incubated at a pH range from pH 6 to pH 9.

In a seventh aspect, the enzyme composition of any one of the first to sixth aspects, wherein the recombinant polypeptide has optimum beta-mannanase activity at a pH of about 8.0 to about pH 9.0.

In an eighth aspect, the enzyme composition of any one of the first to seventh aspects, wherein the recombinant polypeptide retains at least 80% or more of the beta-mannanase activity when incubated at a temperature of between 50° C. and 74° C.

In a ninth aspect, the enzyme composition of any one of the first to eighth aspects, wherein the recombinant polypeptide has optimum beta-mannanase activity at a temperature of about 64° C.

In a tenth aspect, the enzyme composition of any one of the first to ninth aspects, wherein the recombinant polypeptide retains at least 50% of the beta-mannanase activity when incubated for about 2 hours at a temperature of about 75° C.

In an $11^{th}$ aspect, the enzyme composition of any one of any one of the first to $10^{th}$ aspects, wherein the recombinant polypeptide retains at least 95% of the beta-mannanase activity when incubated for about 2 hours at a temperature of up to 55° C.

In a $12^{th}$ aspect, the enzyme composition of any one of the first to $11^{th}$ aspects, wherein the recombinant polypeptide comprises an amino acid sequence that is at least 80% identical to the amino acid sequence of SEQ ID NO:2 or SEQ ID NO:3.

In a $13^{th}$ aspect, the enzyme composition of any one of the first to $12^{th}$ aspects, wherein the recombinant polypeptide comprises an amino acid sequence that is at least 90% identical to the amino acid sequence of SEQ ID NO:2 or SEQ ID NO:3.

In a $14^{th}$ aspect, the enzyme composition of any one of the first to $13^{th}$ aspects, wherein the recombinant polypeptide comprises an amino acid sequence that is at least 95% identical to the amino acid sequence of SEQ ID NO:2 or SEQ ID NO:3.

In a $15^{th}$ aspect, the enzyme composition of any one of the first to $14^{th}$ aspects, wherein the one or more cellulases are selected from one or more beta-glucosidases, one or more cellobiohydrolases, and one or more endoglucanases.

In a $16^{th}$ aspect, the enzyme composition of any one of the first to $15^{th}$ aspects, further comprising one or more other hemicellulases.

In a $17^{th}$ aspect, the enzyme composition of the $16^{th}$ aspect, wherein the one or more other hemicellulases are selected from one or more other beta-mannanases, one or more one or more xylanases, one or more beta-xylosidases, and one or more L-arabinofuranosidases.

In an $18^{th}$ aspect, a nucleic acid encoding the a recombinant polypeptide comprising an amino acid sequence that is at least 70% identical to SEQ ID NO:2 or to the mature sequence of SEQ ID NO:3, wherein the recombinant polypeptide has beta-mannanase activity.

In a $19^{th}$ aspect, the nucleic acid of the $18^{th}$ aspect, wherein the recombinant polypeptide further comprises a signal peptide sequence.

In a $20^{th}$ aspect, the nucleic acid of the $19^{th}$ aspect, wherein the signal peptide sequence is selected from any one of SEQ ID NOs:13-41.

In a $21^{st}$ aspect, an expression vector comprising the nucleic acid of any one of the $18^{th}$ to $20^{th}$ aspects, in operable combination with a regulatory sequence.

In a $22^{nd}$ aspect, a host cell comprising the expression vector of the $21^{st}$ aspect.

In a $23^{rd}$ aspect, the host cell of the $22^{nd}$ aspect, wherein the host cell is a bacterial cell or a fungal cell.

In a $24^{th}$ aspect, a composition comprising the host cell of the $22^{nd}$ or $23^{rd}$ aspect, and a culture medium.

In a $25^{th}$ aspect, a method of producing a beta-mannanase, comprising: culturing the host cell of the $22^{nd}$ or $23^{rd}$ aspect, in a culture medium, under suitable conditions to produce the beta-mannanase.

In a $26^{th}$ aspect, a composition comprising the beta-mannanase produced in accordance with the method of the $25^{th}$ aspect, in supernatant of the culture medium.

In a $27^{th}$ aspect, a method for hydrolyzing a lignocellulosic biomass substrate, comprising: contacting the lignocellulosic biomass substrate with the enzyme composition of any one of the first to $17^{th}$ and $26^{th}$ aspects, to yield glucose and other sugars.

In a $28^{th}$ aspect, the method of the $27^{th}$ aspect, wherein the lignocellulosic biomass substrate comprises up to about 20 wt. %, up to about 15%, or up to about 10 wt. % of galactoglucomannan and/or glucomannan.

In a $29^{th}$ aspect, a composition comprising the enzyme compositions of any one of the first to $17^{th}$ aspects, and a lignocellulosic biomass substrate.

In a $30^{th}$ aspect, the composition of the $29^{th}$ aspect, wherein the lignocellulosic biomass substrate comprises up to about 20 wt. %, or up to about 15 wt. %, or up to about 10 wt. % of galactoglucomannan and/or glucomannan.

BRIEF DESCRIPTION OF THE DRAWINGS

FIG. 1 depicts a map of the pML356 (aprE-BhcnmanA) vector.
FIG. 2 depicts a map of the pTrex3gM construct.
FIG. 3 depicts a pH profile of Bhe Man2. The effect of pH on beta-mannanase activity of Bhe Man2 was measured at 50° C. for 10 minutes using 1% locust bean gum as substrate in 50 mM sodium citrate and 50 mM sodium phosphate buffer adjusted to individual pH values ranging between pH 2-9. The mannanase activity of the Bhe Man2polypeptide at its pH optimum was normalized to 100%, and the mannanase activity of the same polypeptide at other pH values were depicted as relative activity to that at the pH optimum.

FIG. 4 depicts a temperature profile of Bhe Man2. The effect of temperature change on beta-mannanase activity of Bhe Man2 was measured at individual temperature values ranging between 30° C. and 78° C. for 10 minutes using 1% locust bean gum as substrate in a 50 mM sodium citrate buffer, at pH 6.0. The mannanase activity of the Bhe Man2polypeptide at its temperature optimum was normalized to 100%, and the mannanase activity of the same polypeptide at other temperature values were depicted as relative activity to that at the temperature optimum.

FIG. 5 depicts a thermostability profile of Bhe Man2. The thermostability of Bhe Man2 was determined by incubation in 50 mM sodium citrate buffer at pH 6.0 at a set temperature within the range of 40° C. and 65° C. for 2 hours. After incubation, the remaining mannanase activity at each of the incubation temperature was measured. The activity measured from a control sample of Bhe Man2polypeptide kept on ice for the same 2 hours was used as the 100% activity to normalize the residual activity measurements.

FIGS. 6A-6C depict the comparison of levels of hydrolysis achieved by a commercial cellulase/hemicellulase composition Accellerase® TRIO™ vs. a blend of 9 parts Accellerase® TRIO™ with 1 part (i.e., 10 wt. %) of a Bhe Man2 polypeptide, as compared to the same blend of Accellerase® TRIO™ with each of three other beta-mannanases of GH5, a *Streptomyces coelicolor* A3 beta-mannanase of SEQ ID NO:4 ("ScoMan1"), a *Bacillus caldovelox* beta-mannanase of SEQ ID NO:5 ("Bsp Man1"), and a *Micromonospora* sp. L5 beta-mannanase of SEQ ID NO:6 ("Msp Man2) of a given biomass substrate, namely the alkaline KRAFT-pretreated softwood substrate FPP-27, under the same hydrolysis conditions and at different durations of reaction. FIG. 6A depicts the results of hydrolysis after 24 hours. FIG. 6B depicts the results of hydrolysis after 48 hours. FIG. 6C depicts the results of hydrolysis after 72 hours. Details of the experiments are found in Example 9.

FIG. 7 depicts the comparison of total hydrolysis of the FPP-27 alkaline KRAFT-pretreated softwood substrate by Accellerase® TRIO™ vs. a blend of 9 parts Accellerase® TRIO™ with 1 part (i.e., 10 wt. %) of a Bhe Man2 polypeptide, a *Streptomyces coelicolor* A3 beta-mannanase of SEQ ID NO:4 ("ScoMan1"), a *Bacillus caldovelox* beta-mannanase of SEQ ID NO:5 ("Bsp Man1"), and a *Micromonospora* sp. L5 beta-mannanase of SEQ ID NO:6 ("Msp Man2), following a time course of 24 hours to 72 hours. Details of the experiments are found in Example 9.

FIGS. 8A-8G depict the sequences and sequence identifiers of the present disclosure.

DETAILED DESCRIPTION

1. Overview

Described herein are compositions and methods relating to a recombinant beta-mannanase belonging to glycosyl hydrolase family 5 from *Bacillus hemicellulosilyticus*. The present compositions and methods are based, in part, on the observations that recombinant Bhe Man2 polypeptides confer to a cellulase and/or hemicellulase composition comprising at least one cellulase and/or at least one other hemicellulase, an improved capacity to hydrolyze a lignocellulosic biomass material or feedstock than other known beta-mannanases of similar pH optimums and/or temperature optimums. The present compositions and methods are also based on the observation that recombinant Bhe Man2 polypeptides confers rapid viscosity reduction when compositions comprising the polypeptides are used to hydrolyze suitable lignocellulosic biomass substrates, especially when such substrates are treated at high solids levels, and when such substrates contain measurable level of galactoglucomannan (GGM) and/or glucomannan (GM). These features of Bhe Man2 polypeptides make them, or variants thereof, suitable for use in numerous processes, including, for example, in the conversion or hydrolysis of a lignocellulosic biomass feedstock.

Before the present compositions and methods are described in greater detail, it is to be understood that the present compositions and methods are not limited to particular embodiments described, as such may, of course, vary. It is also to be understood that the terminology used herein is for the purpose of describing particular embodiments only, and is not intended to be limiting, since the scope of the present compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The term "recombinant," when used in reference to a subject cell, nucleic acid, polypeptides/enzymes or vector, indicates that the subject has been modified from its native state. Thus, for example, recombinant cells express genes that are not found within the native (non-recombinant) form of the cell, or express native genes at different levels or under different conditions than found in nature. Recombinant nucleic acids may differ from a native sequence by one or more nucleotides and/or are operably linked to heterologous sequences, e.g., a heterologous promoter, signal sequences that allow secretion, etc., in an expression vector. Recombinant polypeptides/enzymes may differ from a native sequence by one or more amino acids and/or are fused with heterologous sequences. A vector comprising a nucleic acid encoding a beta-mannanase is, for example, a recombinant vector.

It is further noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) may further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

2. Definitions

"Beta-mannanase" means a polypeptide or polypeptide domain of an enzyme that has the ability to catalyze the cleavage or hydrolysis of (1→4)-beta-D-mannosidic linkages of mannans, galactomannans, and glucomannans.

As used herein, "Bhe Man2" or "a Bhe Man2 polypeptide" refers to a beta-mannanase belonging to glycosyl hydrolase family 5 (e.g., a recombinant beta-mannanase) derived from *Bacillus hemicellulosilyticus* (and variants thereof), that confers surprising improvements to a cellulase and/or hemicellulase composition in the composition's capability to hydrolyze a lignocellulosic biomass substrate, optionally pretreated, when compared to other known beta-mannanases of similar pH optimums and/or temperature optimums. The Bhe Man2 polypeptide can substitute a substantial portion, e.g., up to about 20 wt. % (e.g., up to about 20 wt. %, up to about 15 wt. %, up to about 10 wt. %, up to about 9 wt. %, up to about 8 wt. %, up to about 7 wt. %, up to about 6 wt. %, up to about 5 wt. %, up to about 4 wt. %, up to about 3 wt. %, up to about 2 wt. %, up to about 1 wt. %) of a cellulase and/or hemicellulase mixture and achieve equal or better hydrolysis of a given lignocellulosic biomass substrate under the same conditions. This allows the use of less cellulases/hemicellulases and more efficient biomass hydrolysis, thus making the overall cellulosic biomass conversion process more economically feasible and sustainable. The Bhe Man2 polypeptide herein was also surprisingly found to confer rapid viscosity reduction or liquefaction, particularly prominently when the biomass substrate is treated with enzyme at high solids levels. According to aspects of the present compositions and methods, Bhe Man2 polypeptides include those having the amino acid sequence depicted in SEQ ID NO:2, as well as derivative or variant polypeptides having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO:2, or to the mature sequence SEQ ID NO:2, or to a fragment of at least 80 residues in length of SEQ ID NO:2, wherein the Bhe Man2 polypeptides not only have beta-mannanase activity and capable of catalyzing the conversion hydrolysis of (1→4)-beta-D-mannosidic linkages of mannans, galactomannans, and glucomannans, but also have higher beta-mannanase activity than other beta-mannases of similar pH optimums and/or temperature optimums, and confer rapid viscosity reduction and liquefaction of high solids biomass substrates, a property that has not been observed with other known beta-mannanases.

"Family 5 glycosyl hydrolase" or "GH5" refers to polypeptides falling within the definition of glycosyl hydrolase family 5 according to the classification by Henrissat, Biochem. J. 280:309-316 (1991), and by Henrissat & Cairoch, Biochem. J., 316:695-696 (1996).

Bhe Man2 polypeptides according to the present compositions and methods described herein can be isolated or purified. By purification or isolation is meant that the Bhe Man2 polypeptide is altered from its natural state by virtue of separating the Bhe Man2 from some or all of the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to the Bhe Man2-containing composition which provide additional benefits, for example, activating agents, anti-inhibition agents, desirable ions, compounds to control pH or other enzymes or chemicals.

As used herein, "microorganism" refers to a bacterium, a fungus, a virus, a protozoan, and other microbes or microscopic organisms.

As used herein, a "derivative" or "variant" of a polypeptide means a polypeptide, which is derived from a precursor polypeptide (e.g., the native polypeptide) by addition of one or more amino acids to either or both the C- and N-terminal end, substitution of one or more amino acids at one or a number of different sites in the amino acid sequence, deletion of one or more amino acids at either or both ends of the polypeptide or at one or more sites in the amino acid sequence, or insertion of one or more amino acids at one or more sites in the amino acid sequence. The preparation of a Bhe Man2 derivative or variant may be achieved in any convenient manner, e.g., by modifying a DNA sequence which encodes the native polypeptides, transformation of that DNA sequence into a suitable host, and expression of the modified DNA sequence to form the derivative/variant Bhe Man2. Derivatives or variants further include Bhe Man2 polypeptides that are chemically modified, e.g., glycosylation or otherwise changing a characteristic of the Bhe Man2 polypeptide. While derivatives and variants of Bhe Man2 are encompassed by the present compositions and methods, such derivates and variants will display improved beta-mannanase activity under the same lignocellulosic biomass substrate hydrolysis conditions, when compared to that of a number of other beta-mannanases having similar pH optimums and/or temperature optimums, for example the ScoMan1 having the sequence of SEQ ID NO:4, or the Bsp Man1, having the sequence of SEQ ID NO:5, or the Msp Man2 of SEQ ID NO:6. In some embodiments, such derivatives and variants will also confer rapid viscosity reduction and liquefaction to a cellulase and/or hemicellulase composition, capable of achieving, for example, at least 10% (e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95%, at least 100%, or even more) improved viscosity reduction or higher liquefaction within the same time period after the biomass substrate is subject to an enzyme composition comprising a Bhe Man2 polypeptide herein, as compared to when that same biomass substrate is subject to a counterpart enzyme composition having the same amounts, proportion, and types of enzymes except that the composition does not comprise the Bhe Man2 polypeptide.

In certain aspects, a Bhe Man2 polypeptide of the compositions and methods herein may also encompasses functional fragment of a polypeptide or a polypeptide fragment having beta-mannanase activity, which is derived from a parent polypeptide, which may be the full length polypeptide comprising or consisting of SEQ ID NO:2, or the mature sequence comprising or consisting SEQ ID NO:3. The functional polypeptide may have been truncated either in the N-terminal region, or the C-terminal region, or in both regions to generate a fragment of the parent polypeptide. For the purpose of the present disclosure, a functional fragment must have at least 20%, more preferably at least 30%, 40%, 50%, or preferably, at least 60%, 70%, 80%, or even more preferably at least 90% of the beta-mannanase activity of that of the parent polypeptide.

In certain aspects, a Bhe Man2 derivative/variant will have anywhere from 70% to 99% (or more) amino acid sequence identity to the amino acid sequence of SEQ ID NO:2, or to the mature sequence SEQ ID NO:3, e.g., 70%, 75%, 80%, 85%, 86%, 87%, 88%, 89%, 90%, 91%, 92%, 93%, 94%, 95%, 96%, 97%, 98%, or 99% amino acid sequence identity to the amino acid sequence of SEQ. ID NO:2 or to the mature sequence SEQ ID NO:3. In some embodiments, amino acid substitutions are "conservative amino acid substitutions" using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. A derivative may, for example, differ by as few as 1 to 10 amino acid residues, such as 6-10, as few as 5, as few as 4, 3, 2, or even 1 amino acid residue. In some embodiments, a Bhe Man2 derivative may have an N-terminal and/or C-terminal deletion, where the Bhe Man2 derivative excluding the deleted terminal portion(s) is identical to a contiguous sub-region in SEQ ID NO: 2 or SEQ ID NO:3.

As used herein, "percent (%) sequence identity" with respect to the amino acid or nucleotide sequences identified herein is defined as the percentage of amino acid residues or nucleotides in a candidate sequence that are identical with the amino acid residues or nucleotides in a Bhe Man2 sequence, after aligning the sequences and introducing gaps, if necessary, to achieve the maximum percent sequence identity, and not considering any conservative substitutions as part of the sequence identity.

By "homologue" shall mean an entity having a specified degree of identity with the subject amino acid sequences and the subject nucleotide sequences. A homologous sequence is taken to include an amino acid sequence that is at least 75%, 80%, 85%, 86%, 87%, 88%, 89%, 90%, 91%, 92%, 93%, 94%, 95%, 96%, 97%, 98% or even 99% identical to the subject sequence, using conventional sequence alignment tools (e.g., Clustal, BLAST, and the like). Typically, homologues will include the same active site residues as the subject amino acid sequence, unless otherwise specified.

Methods for performing sequence alignment and determining sequence identity are known to the skilled artisan, may be performed without undue experimentation, and calculations of identity values may be obtained with definiteness. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Protein Sequence and Structure* 5:Suppl. 3 (National Biomedical Research Foundation, Washington, D.C.). A number of algorithms are available for aligning sequences and determining sequence identity and include, for example, the homology alignment algorithm of Needleman et al. (1970) *J. Mol. Biol.* 48:443; the local homology algorithm of Smith et al. (1981) *Adv. Appl. Math.* 2:482; the search for similarity method of Pearson et al. (1988) *Proc. Natl. Acad. Sci.* 85:2444; the Smith-Waterman algorithm (*Meth. Mol. Biol.* 70:173-187 (1997); and BLASTP, BLASTN, and BLASTX algorithms (see Altschul et al. (1990) *J. Mol. Biol.* 215:403-410).

Computerized programs using these algorithms are also available, and include, but are not limited to: ALIGN or Megalign (DNASTAR) software, or WU-BLAST-2 (Altschul et al., (1996) Meth. Enzym., 266:460-480); or GAP, BESTFIT, BLAST, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can determined by using Clustal W (Thompson J. D. et al. (1994) Nucleic Acids Res. 22:4673-4680) with default parameters, i.e.:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF |

As used herein, "expression vector" means a DNA construct including a DNA sequence which is operably linked to a suitable control sequence capable of affecting the expression of the DNA in a suitable host. Such control sequences may include a promoter to affect transcription, an optional operator sequence to control transcription, a sequence encoding suitable ribosome-binding sites on the mRNA, and sequences which control termination of transcription and translation. Different cell types may be used with different expression vectors. An exemplary promoter for vectors used in *Bacillus subtilis* is the AprE promoter; an exemplary promoter used in *Streptomyces lividans* is the A4 promoter (from *Aspergillus niger*); an exemplary promoter used in *E. coli* is the Lac promoter, an exemplary promoter used in *Saccharomyces cerevisiae* is PGK1, an exemplary promoter used in *Aspergillus niger* is glaA, and an exemplary promoter for *Trichoderma reesei* is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the present compositions and methods are intended to include other forms of expression vectors which serve equivalent functions and which are, or become, known in the art. Thus, a wide variety of host/expression vector combinations may be employed in expressing the DNA sequences described herein. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present compositions and methods are known in the art and are described generally in, for example, Sambrook et al., *Molecular Cloning: A Laboratory Manual, Second Edition*, Cold Spring Harbor Press (1989). Often, such expression vectors including the DNA sequences described herein are transformed into a unicellular host by direct insertion into the genome of a particular species through an integration event (see e.g., Bennett & Lasure, *More Gene Manipulations in Fungi*, Academic Press, San Diego, pp. 70-76 (1991) and articles cited therein describing targeted genomic insertion in fungal hosts).

As used herein, "host strain" or "host cell" means a suitable host for an expression vector including DNA according to the present compositions and methods. Host cells useful in the present compositions and methods are generally prokaryotic or eukaryotic hosts, including any transformable microorganism in which expression can be achieved. Specifically, host strains may be *Bacillus subtilis, Bacillus hemicellulosilyticus, Streptomyces lividans, Escherichia coli, Trichoderma reesei, Saccharomyces cerevisiae, Aspergillus niger, Aspergillus oryzae, Chrysosporium lucknowence, Myceliophthora thermophila*, and various other microbial cells. Host cells are transformed or transfected with vectors constructed using recombinant DNA techniques. Such transformed host cells may be capable of one or both of replicating the vectors encoding Bhe Man2 (and its derivatives or variants (mutants)) and expressing the desired peptide product. In certain embodiments according to the present compositions and methods, "host cell" means both the cells and protoplasts created from the cells of *Trichoderma* sp.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., a beta-mannanase) has been introduced. Exemplary host strains are microbial cells (e.g., bacteria, filamentous fungi, and yeast) capable of expressing the polypeptide of interest. The term "host cell" includes protoplasts created from cells.

The term "heterologous" with reference to a polynucleotide or polypeptide refers to a polynucleotide or polypeptide that does not naturally occur in a host cell.

The term "endogenous" with reference to a polynucleotide or polypeptide refers to a polynucleotide or polypeptide that occurs naturally in the host cell.

The term "expression" refers to the process by which a polypeptide is produced based on a nucleic acid sequence. The process includes both transcription and translation.

As used herein, "signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process. While the native signal sequence of Bhe Man2 may be employed in aspects of the present compositions and methods, other non-native signal sequences may be employed (e.g., one selected from SEQ ID NOs: 13-41).

The beta-mannanase polypeptides of the invention may be referred to as "precursor," "immature," or "full-length," in which case they include a signal sequence, or may be referred to as "mature," in which case they lack a signal sequence. Mature forms of the polypeptides are generally the most useful. Unless otherwise noted, the amino acid residue numbering used herein refers to the mature forms of the respective beta-mannanase polypeptides. The beta-mannanase polypeptides of the invention may also be truncated to remove the N or C-termini, so long as the resulting polypeptides retain beta-mannanase activity.

The beta-mannanase polypeptides of the invention may also be a "chimeric" or "hybrid" polypeptide, in that it includes at least a portion of a first beta-mannanase polypeptide, and at least a portion of a second beta-mannanase polypeptide (such chimeric beta-mannanase polypeptides may, for example, be derived from the first and second beta-mannanase using known technologies involving the swapping of domains on each of the beta-mannanase). The present beta-mannanase polypeptides may further include heterologous signal sequence, an epitope to allow tracking or purification, or the like. When the term of "heterologous" is used to refer to a signal sequence used to express a polypeptide of interest, it is meant that the signal sequence is, for example, derived from a different microorganism as the polypeptide of interest. Examples of suitable heterologous signal sequences for expressing the Bhe Man2 polypeptides herein, may be, for example, those from *Trichoderma reesei*, other *Trichoderma* sp., *Aspergillus niger*, *Aspergillus oryzae*, other *Aspergillus* sp., *Chrysosporium*, and other organisms, those from *Bacillus subtilis*, *Bacillus hemicellulosilyticus*, other *Bacillus* species, *E. coli*., or other suitable microbes.

As used herein, "functionally attached" or "operably linked" means that a regulatory region or functional domain having a known or desired activity, such as a promoter, terminator, signal sequence or enhancer region, is attached to or linked to a target (e.g., a gene or polypeptide) in such a manner as to allow the regulatory region or functional domain to control the expression, secretion or function of that target according to its known or desired activity.

As used herein, the terms "polypeptide" and "enzyme" are used interchangeably to refer to polymers of any length comprising amino acid residues linked by peptide bonds. The conventional one-letter or three-letter codes for amino acid residues are used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, "wild-type" and "native" genes, enzymes, or strains, are those found in nature.

The terms "wild-type," "parental," or "reference," with respect to a polypeptide, refer to a naturally-occurring polypeptide that does not include a man-made substitution, insertion, or deletion at one or more amino acid positions. Similarly, the term "wild-type," "parental," or "reference," with respect to a polynucleotide, refers to a naturally-occurring polynucleotide that does not include a man-made nucleoside change. However, a polynucleotide encoding a wild-type, parental, or reference polypeptide is not limited to a naturally-occurring polynucleotide, but rather encompasses any polynucleotide encoding the wild-type, parental, or reference polypeptide.

As used herein, a "variant polypeptide" refers to a polypeptide that is derived from a parent (or reference) polypeptide by the substitution, addition, or deletion, of one or more amino acids, typically by recombinant DNA techniques. Variant polypeptides may differ from a parent polypeptide by a small number of amino acid residues. They may be defined by their level of primary amino acid sequence homology/identity with a parent polypeptide. Suitably, variant polypeptides have at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity to a parent polypeptide.

As used herein, a "variant polynucleotide" encodes a variant polypeptide, has a specified degree of homology/identity with a parent polynucleotide, or hybridized under stringent conditions to a parent polynucleotide or the complement thereof. Suitably, a variant polynucleotide has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity to a parent polynucleotide or to a complement of the parent polynucleotide. Methods for determining percent identity are known in the art and described above.

The term "derived from" encompasses the terms "originated from," "obtained from," "obtainable from," "isolated from," and "created from," and generally indicates that one specified material find its origin in another specified material or has features that can be described with reference to the another specified material.

As used herein, the term "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm −5° C. (5° C. below the Tm of the probe); "high stringency" at about 5-10° C. below the Tm; "intermediate stringency" at about 10-20° C. below the Tm of the probe; and "low stringency" at about 20-25° C. below the Tm. Alternatively, or in addition, hybridization conditions can be based upon the salt or ionic strength conditions of hybridization, and/or upon one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

As used herein, the term "hybridization" refers to the process by which a strand of nucleic acid joins with a complementary strand through base pairing, as known in the art. More specifically, "hybridization" refers to the process by which one strand of nucleic acid forms a duplex with, i.e., base pairs with, a complementary strand, as occurs during blot hybridization techniques and PCR techniques. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Intermediate and high stringency hybridization conditions are well known in the art. For example, intermediate stringency hybridizations may be carried out with an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. High stringency hybridization conditions may be hybridization at 65° C. and 0.1×SSC (where 1×SSC=0.15 M NaCl, 0.015 M Na$_3$ citrate, pH 7.0). Alternatively, high stringency hybridization conditions can be carried out at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. And very high stringent hybridization conditions may be hybridization at 68° C. and 0.1×SSC. Those of skill in the art know how to adjust the temperature, ionic strength, etc. as necessary to accommodate factors such as probe length and the like.

A nucleic acid encoding a variant beta-mannase may have a $T_m$ reduced by 1° C.-3° C. or more compared to a duplex formed between the nucleotide of SEQ ID NO: 1 and its identical complement.

The phrase "substantially similar" or "substantially identical," in the context of at least two nucleic acids or polypeptides, means that a polynucleotide or polypeptide comprises a sequence that has at least about 90%, at least about 91%, at least about 92%, at least about 93%, at least about 94%, at least about 95%, at least about 96%, at least about 97%, at least about 98%, or even at least about 99% identical to a parent or reference sequence, or does not include amino acid substitutions, insertions, deletions, or modifications made only to circumvent the present description without adding functionality.

As used herein, an "expression vector" refers to a DNA construct containing a DNA sequence that encodes a specified polypeptide and is operably linked to a suitable control sequence capable of effecting the expression of the polypeptides in a suitable host. Such control sequences may include a promoter to effect transcription, an optional operator sequence to control such transcription, a sequence encoding suitable mRNA ribosome binding sites and/or sequences that control termination of transcription and translation. The vector may be a plasmid, a phage particle, or a potential genomic insert. Once transformed into a suitable host, the vector may replicate and function independently of the host genome, or may, in some instances, integrate into the host genome.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in a manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a polypeptide, and which facilitates the secretion of the mature form of the polypeptide from the cell. The mature form of the extracellular polypeptide lacks the signal sequence which is cleaved off during the secretion process.

The term "selective marker" or "selectable marker," refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "regulatory element," refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally cells of prokaryotic or eukaryotic hosts that are transformed or transfected with vectors constructed using recombinant DNA techniques known in the art. Transformed host cells are capable of either replicating vectors encoding the polypeptide variants or expressing the desired polypeptide variant. In the case of vectors, which encode the pre- or pro-form of the polypeptide variant, such variants, when expressed, are typically secreted from the host cell into the host cell medium.

The term "introduced," in the context of inserting a nucleic acid sequence into a cell, means transformation, transduction, or transfection. Means of transformation include protoplast transformation, calcium chloride precipitation, electroporation, naked DNA, and the like as known in the art. (See, Chang and Cohen (1979) *Mol. Gen. Genet.* 168:111-115; Smith et al., (1986) *Appl. Env. Microbiol.* 51:634; and the review article by Ferrari et al., in Harwood, *Bacillus*, Plenum Publishing Corporation, pp. 57-72, 1989).

"Fused" polypeptide sequences are connected, i.e., operably linked, via a peptide bond between two subject polypeptide sequences.

The term "filamentous fungi" refers to all filamentous forms of the subdivision *Eumycotina*, particulary *Pezizomycotina* species.

Other technical and scientific terms have the same meaning as commonly understood by one of ordinary skill in the art to which this disclosure pertains (See, e.g., Singleton and Sainsbury, *Dictionary of Microbiology and Molecular Biology*, 2d Ed., John Wiley and Sons, NY 1994; and Hale and Marham, *The Harper Collins Dictionary of Biology*, Harper Perennial, NY 1991).

The beta-mannanase enzyme Bhe Man2 from *Bacillus hemicellulosilyticus* (SEQ ID NO:2) has the following amino acid sequence:

MKKSLSQIYHLIICALIASVGIMGITTSPSAASSGFYVDGNTLYDANGQP

FVMRGINHGHAWYKDTASTAIPAIAEQGANTIRIVLSDGGQWEKDDIDTV

REVIELAEQNKMVAVVEVHDATGRDSRSDLNRAVDYWIEMKDALIGKEDT

VIINIANEWYGSWDGSAWADGYIDVIPKLRDAGLTHTLMVDAAGWGQYPQ

SIHDYGQDVFNADPLKNTMFSIHMYEYAGGDANTVRSNIDRVIDQDLALV

IGEFGHRHTDGDVDEDTILSYSEETGTGWLAWSWKGNSTEWDYLDLSEDW

AGQHLTDWGNRIVHGADGLQETSKPSTVFSDDNGGSPEPPTATTLYDFEG

STQGWHGSNVAGGPWSVTEWGTSGNYSLKADVNLTSNSSHELYSEQSRNL

HGYSQLNATVRHANWGNHGNGMNARLYVKTGSDYTWYSGPFTRINSSNSG

TTLSFDLNNIENSHHVREIGVQFSAADNSSGQTALYVDNVTLR

The mature beta-mannanase enzyme, as based on the removal of the predicted signal peptide sequence if SEQ ID NO:3:

SSGFYVDGNTLYDANGQPFVMRGINHGHAWYKDTASTAIPAIAEQGANTI

RIVLSDGGQWEKDDIDTVREVIELAEQNKMVAVVEVHDATGRDSRSDLNR

AVDYWIEMKDALIGKEDTVIINIANEWYGSWDGSAWADGYIDVIPKLRDA

GLTHTLMVDAAGWGQYPQSIHDYGQDVFNADPLKNTMFSIHMYEYAGGDA

NTVRSNIDRVIDQDLALVIGEFGHRHTDGDVDEDTILSYSEETGTGWLAW

SWKGNSTEWDYLDLSEDWAGQHLTDWGNRIVHGADGLQETSKPSTVFSDD

NGGSPEPPTATTLYDFEGSTQGWHGSNVAGGPWSVTEWGTSGNYSLKADV

NLTSNSSHELYSEQSRNLHGYSQLNATVRHANWGNHGNGMNARLYVKTGS

DYTWYSGPFTRINSSNSGTTLSFDLNNIENSHHVREIGVQFSAADNSSGQ

TALYVDNVTLR

A number of other bacterial beta-mannanases having similar pH optimums and/or temperature optimums have been used as benchmark molecules herein, including a beta-mannanase of GH5, called "ScoMan1" herein from *Streptomyces coelicolor* strain A2, having the following amino acid sequence (SEQ ID NO: 4):

MRKPRSTLITTAGMAFAAVLGLLFALAGPSAGRAEAAAGGIHVSNGRVLE

GNGSVFVMRGVNHAYTWYPDRTGSIADIAAKGANTVRVVLSSGGRWTKTS

ASEVSALIGQCKANKVICVLEVHDTTGYGEDGAATSLDQAADYWVSVKSA

LEGQEDYVVVNIGNEPFGNTNYTAWTDATKSAIGKLRGAGLDHALMVDAP

NWGQDWSGTMRSNAASVFASDPDRNTVFSVHMYGVYDTAAEVRDYLNAFV

GSGLPIVVGEFGDQHSDGNPDEDAIMATAQSLGVGYLGWSWSGNGGGVEY

LDMVNGFDPNSLTSWGNRIFYGSNGIAATSRTATVYGGGGGSTGGTAPNG

YPYCVNGGASDPDGDGWGWENSRSCVVRGSAADH

Benchmark beta-mannanases also include a beta-mannanase called "Bsp Man1" of GH5 from *Bacillus caldovelox*, having the following amino acid sequence (SEQ ID NO:5)

MNKKWSYTFIALLVSIVCAVVPIFFSQNNVHAKTKREPATPTKDNEFVYRK

GDKLMIGNKEFRFVGTNNYYLHYKSNQMIDDVIESAKKMGIKVIRLWGFFD

GMTSENQAHNTYMQYEMGKYMGEGPIPKELEGAQNGFERLDYTIYKAKQEG

IRLVIVLTNNWNNFGGMMQYVNWIGETNHDLFYTDERIKTAYKNYVHYLIN

RKNQYTGIIYKNEPTIMAWELANEPRNDSDPTGDTLVRWADEMSTYIKSID

PHHLVAVGDEGFFRRSSGGFNGEGSYMYTGYNGVDWDRLIALKNIDYGTFH

LYPEHWGISPENVEKWGEQYILDHLAAGKKAKKPVVLEEYGISATGVQNRE

MIYDTWNRTMFEHGGTGAMFWLLTGIDDNPESADENGYYPDYDGFRIVNDH

SSVTNLLKTYAKLFNGDRHVEKEPKVYFAFPAKPQDVRGTYRVKVKVASDQ

HKVQKVQLQLSSHDEAYTMKYNASFDYYEFDWDTTKEIEDSTVTLKATATL

TNKQTIASDEVTVNIQNASAYEIIKQFSFDSDMNNVYADGTWQANFGIPAI

STPKTRCLRVNVDLPGNADWEEVKVKISPISELSETSRISFDLLLPRVDVN

GALRPYIALNPGWIKIGVDQYHVNVNDLTTVTIHNQQYKLLHVNVEFNAMP

NVNELFLNIVGNKLAYKGPIYIDNVTLFKKI

Benchmark beta-mannanase further include a beta-mannanase called "Msp Man2" from *Micromonospora* sp., strain L5, having the following amino acid sequence (SEQ ID NO:6):

MKKLLSVAGAALLTALAAVFALGQPAHAATGFSVSNGRLYDANGVEFVMRG

VNHAHTWYPQQTSSFANIKALGANTVRVVLSSGDRWTKNSAADVANVISLC

KANRMICVLEVHDTTGYGEDGAATTLAKATDYWLSIADVLKGQEKYVIVNI

GNEPFGNQGYSAWTTDTSNAIKRLRAAGLTHTIMVDAPNWGQDWTFTMRDN

AGTVFAADPQRNTVFSIHMYGVFDTAAEISDYLGRFRTAGLPIVVGEFGFN

HSDGNPDEDAIMAYAQANGIGYLGWSWSGNGGGVEYLDMTTAFNPAQLTSW

GQRIFNGANGIAATSREASVYAGSTPTASPTGSPTTSPTPTSSPSPTPPPT

TTPPPSGGCTATYTVANSWQGGFQGEVKVTAGAAAITGWTVRWTFANGQSV

TQAWNASVSNSGSAYTARNVDYNGRLGVGASTSFGFIGSWTGTNSTPAVTC

TAS

3. Beta-Mannanase Polypeptides, Polynucleotides, Vectors, and Host Cells

A. Bhe Man2 Polypeptides

In one aspect, the present compositions and methods provide a recombinant Bhe Man2 beta-mannanase polypeptide, fragments thereof, or variants thereof having beta-mannanase activity. An example of a recombinant beta-mannanase polypeptide was isolated from *Bacillus hemicellulosilyticus*. The mature Bhe Man2 polypeptide has the amino acid sequence set forth as SEQ ID NO:3. Similar, substantially similar Bhe Man2 polypeptides may occur in nature, e.g., in other strains or isolates of *Bacillus hemicellulosilyticus*, or *Bacillus* sp. These and other recombinant Bhe Man2 polypeptides are encompassed by the present compositions and methods.

In some embodiments, the recombinant Bhe Man2 polypeptide is a variant Bhe Man2 polypeptide having a specified degree of amino acid sequence identity to the exemplified Bhe Man2 polypeptide, e.g., at least 70%, 75%, 80%, 85%, 90%, 91%, 92%, 93%, 94%, 95%, 96%, 97%, 98%, or even at least 99% sequence identity to the amino acid sequence of SEQ ID NO:2 or to the mature sequence SEQ ID NO:3. Sequence identity can be determined by amino acid sequence alignment, e.g., using a program such as BLAST, ALIGN, or CLUSTAL, as described herein.

In certain embodiments, the recombinant Bhe Man2 polypeptides are produced recombinantly, in a microorganism, for example, in a bacterial or fungal host organism, while in others the Bhe Man2 polypeptides are produced synthetically, or are purified from a native source (e.g., *Bacillus hemicellulosilyticus*).

In certain embodiments, the recombinant Bhe Man2 polypeptide includes substitutions that do not substantially affect the structure and/or function of the polypeptide. Examples of these substitutions are conservative mutations, as summarized in Table I.

Table I

Amino Acid Substitutions

| Original Residue | Code | Acceptable Substitutions |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, beta-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4- carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Substitutions involving naturally occurring amino acids are generally made by mutating a nucleic acid encoding a recombinant Bhe Man2 polypeptide, and then expressing the variant polypeptide in an organism. Substitutions involving non-naturally occurring amino acids or chemical modifications to amino acids are generally made by chemically modifying a Bhe Man2 polypeptide after it has been synthesized by an organism.

In some embodiments, variant recombinant Bhe Man2 polypeptides are substantially identical to SEQ ID NO:2 or SEQ ID NO:3, meaning that they do not include amino acid substitutions, insertions, or deletions that do not significantly affect the structure, function, or expression of the polypeptide. Such variant recombinant Bhe Man2 polypeptides will include those designed to circumvent the present description. In some embodiments, variants recombinant Bhe Man2 polypeptides, compositions and methods comprising these variants are not substantially identical to SEQ ID NO:2 or SEQ ID NO:3, but rather include amino acid substitutions, insertions, or deletions that affect, in certain circumstances, substantially, the structure, function, or expression of the polypeptide herein such that improved characteristics, including, e.g., improved specific activity to hydrolyze a mannan-containing lignocellulosic substrate, more rapid viscosity reduction when used to treat high solids biomass substrates, improved expression in a desirable host organism, improved thermostability, pH stability, etc, as compared to that of a polypeptide of SEQ ID NO:2 or SEQ ID NO:3 can be achieved.

In some embodiments, the recombinant Bhe Man2 polypeptide (including a variant thereof) has beta-mannanase activity. Beta-mannanase activity can be determined using an assay measuring the release of reducing sugars from a galactomannan substrate, for example, in accordance with the description of Example 5. Beta-mannanase activity can be determined by combining with a cellulase and/or hemicellulase mixture, followed by using such a mixture to treat a suitable mannan-containing biomass substrate, such as, for example, a woody substrate, etc., in accordance with the protocols and conditions described in, for example, Example 9, or by suitable assays, or methods of activity measurement known in the art.

Recombinant Bhe Man2 polypeptides include fragments of "full-length" Bhe Man2 polypeptides that retain beta-mannanase activity. Preferably those functional fragments (i.e., fragments that retain beta-mannanase activity) are at least 80 amino acid residues in length (e.g., at least 80 amino acid residues, at least 100 amino acid residues, at least 120 amino acid residues, at least 140 amino acid residues, at least 160 amino acid residues, at least 180 amino acid residues, at least 200 amino acid residues, at least 220 amino acid residues, at least 240 amino acid residues, at least 260 amino acid residues, at least 280 amino acid residues, at least 300 amino acid residues in length or longer). Such fragments suitably retain the active site of the full-length precursor polypeptides or full length mature polypeptides but may have deletions of non-critical amino acid residues. The activity of fragments can be readily determined using the methods of measuring beta-mannanase activity described herein, for example the assay described in Example 5, and the hydrolysis performance measurements as those described in Example 9, or by suitable assays or other means of activity measurements known in the art.

In some embodiments, the Bhe Man2 amino acid sequences and derivatives are produced as an N- and/or C-terminal fusion protein, for example, to aid in extraction, detection and/or purification and/or to add functional properties to the Bhe Man2 polypeptides. Examples of fusion protein partners include, but are not limited to, glutathione-S-transferase (GST), 6×His, GAL4 (DNA binding and/or transcriptional activation domains), FLAG-, MYC-tags or other tags known to those skilled in the art. In some embodiments, a proteolytic cleavage site is provided between the fusion protein partner and the polypeptide sequence of interest to allow removal of fusion sequences. Suitably, the fusion protein does not hinder the activity of the recombinant Bhe Man2 polypeptide. In some embodiments, the recombinant Bhe Man2 polypeptide is fused to a functional domain including a leader peptide, propeptide, binding domain and/or catalytic domain. Fusion proteins are optionally linked to the recombinant Bhe Man2 polypeptide through a linker sequence that joins the Bhe Man2 polypeptide and the fusion domain without significantly affecting the properties of either component. The linker optionally contributes functionally to the intended application.

The present disclosure provides host cells that are engineered to express one or more Bhe Man2 polypeptides of the disclosure. Suitable host cells include cells of any microorganism (e.g., cells of a bacterium, a protist, an alga, a fungus (e.g., a yeast or filamentous fungus), or other microbe), and are preferably cells of a bacterium, a yeast, or a filamentous fungus.

Suitable host cells of the bacterial genera include, but are not limited to, cells of *Escherichia, Bacillus, Lactobacillus, Pseudomonas,* and *Streptomyces*. Suitable cells of bacterial species include, but are not limited to, cells of *Escherichia coli, Bacillus subtilis, Bacillus hemicellulosilyticus, Lactobacillus brevis, Pseudomonas aeruginosa,* and *Streptomyces lividans*.

Suitable host cells of the genera of yeast include, but are not limited to, cells of *Saccharomyces, Schizosaccharomyces, Candida, Hansenula, Pichia, Kluyveromyces,* and *Phaffia*. Suitable cells of yeast species include, but are not limited to, cells of *Saccharomyces cerevisiae, Schizosaccharomyces pombe, Candida albicans, Hansenula polymorpha, Pichia pastoris, P. canadensis, Kluyveromyces marxianus,* and *Phaffia rhodozyma*.

Suitable host cells of filamentous fungi include all filamentous forms of the subdivision *Eumycotina*. Suitable cells of filamentous fungal genera include, but are not limited to, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes,* and *Trichoderma*.

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei,* and *Trichoderma viride*.

Methods of transforming nucleic acids into these organisms are known in the art. For example, a suitable procedure for transforming *Aspergillus* host cells is described in EP 238 023.

In some embodiments, the recombinant Bhe Man2 polypeptide is fused to a signal peptide to, for example, facilitate extracellular secretion of the recombinant Bhe Man2 polypeptide. For example, in certain embodiments, the signal peptide is a non-native signal peptide such as the *B. subtilis* AprE signal peptide of SEQ ID NO:13. In some embodiments, the Bhe Man2 polypeptide has an N-terminal extension of Ala-Gly-Lys between the mature form and the signal polypeptide. In particular embodiments, the recombinant Bhe Man2 polypeptide is expressed in a heterologous organism as a secreted polypeptide. The compositions and methods herein thus encompass methods for expressing a Bhe Man2 polypeptide as a secreted polypeptide in a heterologous organism.

The disclosure also provides expression cassettes and/or vectors comprising the above-described nucleic acids. Suitably, the nucleic acid encoding a Bhe Man2 polypeptide of the disclosure is operably linked to a promoter. Promoters are well known in the art. Any promoter that functions in the host cell can be used for expression of a beta-mannanase and/or any of the other nucleic acids of the present disclosure. Initiation control regions or promoters, which are useful to drive expression of a beta-mannanase nucleic acids and/or any of the other nucleic acids of the present disclosure in various host cells are numerous and familiar to those skilled in the art (see, for example, WO 2004/033646 and references cited therein). Virtually any promoter capable of driving these nucleic acids can be used.

Specifically, where recombinant expression in a filamentous fungal host is desired, the promoter can be a filamentous fungal promoter. The nucleic acids can be, for example, under the control of heterologous promoters. The nucleic acids can also be expressed under the control of constitutive or inducible promoters. Examples of promoters that can be used include, but are not limited to, a cellulase promoter, a xylanase promoter, the 1818 promoter (previously identified as a highly expressed protein by EST mapping *Trichoderma*). For example, the promoter can suitably be a cellobiohydrolase, endoglucanase, or beta-glucosidase promoter. A particulary suitable promoter can be, for example, a *T. reesei* cellobiohydrolase, endoglucanase, or beta-glucosidase promoter. For example, the promoter is a cellobiohydrolase I (cbh1) promoter. Non-limiting examples of promoters include a cbh1, cbh2, egl1, egl2, egl3, egl4, egl5, pki1, gpd1, xyn1, or xyn2 promoter. Additional non-limiting examples of promoters include a *T. reesei* cbh1, cbh2, egl1, egl2, egl3, egl4, egl5, pki1, gpd1, xyn1, or xyn2 promoter.

The nucleic acid sequence encoding a Bhe Man2 polypeptide herein can be included in a vector. In some aspects, the vector contains the nucleic acid sequence encoding the Bhe Man2 polypeptide under the control of an expression control sequence. In some aspects, the expression control sequence is a native expression control sequence. In some aspects, the expression control sequence is a non-native expression control sequence. In some aspects, the vector contains a selective marker or selectable marker. In some aspects, the nucleic acid sequence encoding the Bhe Man2 polypeptide is integrated into a chromosome of a host cell without a selectable marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Suitable vectors can be maintained in low, medium, or high copy number in the host cell. Protocols for obtaining and using such vectors are known to those in the art (see, for example, Sambrook et al., Molecular Cloning: A Laboratory Manual, 2$^{nd}$ ed., Cold Spring Harbor, 1989).

In some aspects, the expression vector also includes a termination sequence. Termination control regions may also be derived from various genes native to the host cell. In some aspects, the termination sequence and the promoter sequence are derived from the same source.

A nucleic acid sequence encoding a Bhe Man2 polypeptide can be incorporated into a vector, such as an expression vector, using standard techniques (Sambrook et al., Molecular Cloning: A Laboratory Manual, Cold Spring Harbor, 1982).

In some aspects, it may be desirable to over-express a Bhe Man2 polypeptide and/or one or more of any other nucleic acid described in the present disclosure at levels far higher than currently found in naturally-occurring cells. In some embodiments, it may be desirable to under-express (e.g., mutate, inactivate, or delete) an endogenous beta-mannanase and/or one or more of any other nucleic acid described in the present disclosure at levels far below that those currently found in naturally-occurring cells.

B. Bhe Man2-Encoding Polynucleotides

Another aspect of the compositions and methods described herein is a polynucleotide or a nucleic acid sequence that encodes a recombinant Bhe Man2 polypeptide (including variants and fragments thereof) having beta-mannanase activity. In some embodiments the polynucleotide is provided in the context of an expression vector for directing the expression of a Bhe Man2 polypeptide in a heterologous organism, such as one identified herein. The polynucleotide that encodes a recombinant Bhe Man2 polypeptide may be operably-linked to regulatory elements (e.g., a promoter, terminator, enhancer, and the like) to assist in expressing the encoded polypeptides.

An example of a polynucleotide sequence encoding a recombinant Bhe Man2 polypeptide has the nucleotide sequence of SEQ ID NO:1. Similar, including substantially identical, polynucleotides encoding recombinant Bhe Man2 polypeptides and variants may occur in nature, e.g., in other strains or isolates of *Bacillus hemicellulosilyticus*, or *Bacillus* sp. In view of the degeneracy of the genetic code, it will be appreciated that polynucleotides having different nucleotide sequences may encode the same Bhe Man2 polypeptides, variants, or fragments.

In some embodiments, polynucleotides encoding recombinant Bhe Man2 polypeptides have a specified degree of amino acid sequence identity to the exemplified polynucleotide encoding a Bhe Man2 polypeptide, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or even at least 99% sequence identity to the amino acid sequence of SEQ ID NO:2, or to the mature sequence of SEQ ID NO:3. Homology can be determined by amino acid sequence alignment, e.g., using a program such as BLAST, ALIGN, or CLUSTAL, as described herein.

In some embodiments, the polynucleotide that encodes a recombinant Bhe Man2 polypeptide is fused in frame behind (i.e., downstream of) a coding sequence for a signal peptide for directing the extracellular secretion of a recombinant Bhe Man2 polypeptide. As described herein, the term "heterologous" when used to refer to a signal sequence used to express a polypeptide of interest, it is meant that the signal sequence and the polypeptide of interest are from different organisms. Heterologous signal sequences include, for example, those from other fungal cellulase genes, such as, e.g., the signal sequence of *Trichoderma reesei* CBH1. Expression vectors may be provided in a heterologous host cell suitable for expressing a recombinant Bhe Man2 polypeptide, or suitable for propagating the expression vector prior to introducing it into a suitable host cell.

In some embodiments, polynucleotides encoding recombinant Bhe Man2 polypeptides hybridize to the polynucleotide of SEQ ID NO:1 (or to the complement thereof) under specified hybridization conditions. Examples of conditions are intermediate stringency, high stringency and extremely high stringency conditions, which are described herein.

Bhe Man2 polynucleotides may be naturally occurring or synthetic (i.e., man-made), and may be codon-optimized for expression in a different host, mutated to introduce cloning sites, or otherwise altered to add functionality.

The nucleic acid sequence encoding the coding region of Bhe Man2 polypeptide derived from *Bacillus hemicellulosilyticus* is as follows (SEQ ID NO: 1), wherein the nucleic acid sequence encoding the predicted signal peptide sequence is italicized:

*ATGAAAAAAAGTCTATCTCAGATTTATCACTTAATTATTTGCGCACTTATT*

*GCTAGTGTGGGGATCATGGGAATTACCACATCTCCATCAGCAGCAAGTTCA*

GGCTTTTATGTTGATGGCAATACGTTATATGACGCAAACGGGCAACCATTT

GTCATGAGAGGTATTAACCATGGACATGCTTGGTATAAAGACACCGCTTCA

ACAGCTATTCCTGCCATTGCAGAGCAAGGCGCCAACACGATACGTATTGTT

TTATCAGATGGCGGTCAATGGGAAAAAGACGACATTGACACCGTTCGTGAA

GTTATTGAGCTTGCGGAGCAAAATAAAATGGTGGCTGTCGTTGAAGTTCAT

GATGCCACGGGCCGCGATTCGCGCAGTGATTTAAATCGAGCCGTTGATTAT

TGGATAGAAATGAAAGATGCGCTTATCGGTAAAGAAGATACGGTTATTATT

AACATTGCAAACGAGTGGTATGGGAGTTGGGATGGCTCAGCTTGGGCCGAT

GGCTATATTGATGTCATTCCGAAGCTTCGCGATGCCGGCTTAACACACACC

TTAATGGTTGATGCAGCAGGATGGGGGCAATATCCGCAATCTATTCATGAT

TACGGACAAGATGTGTTTAATGCAGATCCGTTAAAAAATACGATGTTCTCC

ATCCATATGTATGAGTATGCTGGTGGTGATGCTAACACTGTTAGATCAAAT

ATTGATAGAGTCATAGATCAAGACCTTGCTCTCGTAATAGGTGAATTCGGT

CATAGACATACTGATGGTGATGTTGATGAAGATACAATCCTTAGTTATTCT

GAAGAAACTGGCACAGGGTGGCTCGCTTGGTCTTGGAAAGGCAACAGTACC

GAATGGGACTATTTAGACCTTTCAGAAGACTGGGCTGGTCAACATTTAACT

GATTGGGGGAATAGAATTGTCCACGGGGCCGATGGCTTACAGGAAACCTCC

-continued

```
AAACCATCCACCGTATTTTCAGATGATAACGGTGGTAGCCCTGAACCGCCA

ACTGCTACTACCTTGTATGACTTTGAAGGAAGTACACAAGGTTGGCATGGA

AGCAACGTAGCCGGTGGCCCTTGGTCCGTAACAGAGTGGGGTACTTCAGGT

AACTACTCTTTAAAAGCCGATGTAAATTTAACCTCAAATTCTTCACATGAA

CTGTATAGTGAACAAAGTCGTAATCTACACGGATACTCTCAGCTCAACGCA

ACCGTTCGCCATGCCAATTGGGGAAATCACGGTAATGGCATGAATGCAAGA

CTTTACGTGAAAACGGGCTCTGATTATACATGGTATAGCGGTCCTTTTACA

CGTATCAATAGCTCCAACTCAGGTACAACGTTATCTTTTGATTTAAACAAC

ATCGAAAATAGTCATCATGTTAGGGAAATAGGCGTGCAATTTTCAGCGGCA

GATAATAGCAGCGGTCAAACTGCTCTATACGTTGATAATGTTACTTTAAGA
```

As is well known to those of ordinary skill in the art, due to the degeneracy of the genetic code, polynucleotides having significantly different sequences can nonetheless encode identical, or nearly identical, polypeptides. As such, aspects of the present compositions and methods include polynucleotides encoding Bhe Man2 polypeptides or derivatives thereof that contain a nucleic acid sequence that is at least 70% identical to SEQ ID NO:1, including at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO:1. In some embodiments, Bhe Man2 polypeptides contain a nucleic acid sequence that is identical to SEQ ID NO: 1.

In some embodiments, polynucleotides may include a sequence encoding a signal peptide. Many convenient signal sequences may be suitably employed.

C. Purification from Natural Isolates

The Bhe Man2 polypeptides can be purified from natural isolates (e.g., from a strain of *Bacillus hemicellulosilyticus*) by known and commonly employed methods. For example, cells containing a Bhe Man2 polypeptide can be disrupted by various physical or chemical means, such as freeze-thaw cycling, sonication, mechanical disruption, or cell lysing agents. Cell supernatants may be collected (for example from cells that secrete the protein into the medium). The Bhe Man2 polypeptide can be recovered from the medium and/or lysate by conventional techniques including separations of the cells/debris from the medium by centrifugation, filtration, and precipitation of the proteins in the supernatant or filtrate with a salt, for example, ammonium sulphate. The Bhe Man2 polypeptide can then be purified from the disrupted cells by procedures such as: fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and affinity chromatography. Various methods of protein purification may be employed and such methods are known in the art and described for example in Deutscher, *Methods in Enzymology*, 182 (1990); Scopes, *Protein Purification: Principles and Practice*, Springer-Verlag, New York (1982).

D. Chemical Synthesis

Alternatively, the Bhe Man2 polypeptide sequence, or portions thereof, may be produced by direct peptide synthesis using solid-phase techniques (see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of a Bhe Man2 polypeptide may be chemically synthesized separately and combined using chemical or enzymatic methods to produce a full-length Bhe Man2.

E. Recombinant Methods of Making

Isolation of DNA Encoding the Bhe Man2 Polypeptide

DNA encoding a Bhe Man2 polypeptide may be obtained from a cDNA library prepared from a microorganism believed to possess the Bhe Man2 mRNA (e.g., *Bacillus hemicellulosilyticus*) and to express it at a detectable level. The Bhe Man2-encoding gene may also be obtained from a genomic library or by oligonucleotide synthesis.

Libraries can be screened with probes (such as antibodies to a Bhe Man2 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding Bhe Man2 is to use PCR methodology (Sambrook et al., supra; Dieffenbach et al., *PCR Primer: A Laboratory Manual* (Cold Spring Harbor Laboratory Press, 1995)).

In known techniques for screening a cDNA library, the oligonucleotide sequences selected as probes should be of sufficient length and sufficiently unambiguous that false positives are minimized. The oligonucleotide can be labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., *Molecular Cloning: A Laboratory Manual* (New York: Cold Spring Harbor Laboratory Press, 1989).

Nucleic acids having protein coding sequence may be obtained by screening selected cDNA or genomic libraries using the deduced amino acid sequence disclosed herein for the first time, and, if necessary, using conventional primer extension procedures as described in Sambrook et al., *Molecular Cloning: A Laboratory Manual* (New York: Cold Spring Harbor Laboratory Press, 1989), to detect precursors and processing intermediates of mRNA that may not have been reverse-transcribed into cDNA.

Selection and Transformation of Host Cells

Host cells are transfected or transformed with expression or cloning vectors described herein for Bhe Man2 production. The host cells are cultured in conventional nutrient media modified as appropriate for inducing promoters, selecting transformants, or amplifying the genes encoding the desired sequences. The culture conditions, such as media, temperature, pH and the like, can be selected by the ordinarily skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., *Molecular Cloning: A Laboratory Manual* (New York: Cold Spring Harbor Laboratory Press, 1989).

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., *Molecular Cloning: A Laboratory Manual* (New York: Cold Spring Harbor Laboratory Press, 1989), or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. Transformations into yeast can be carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, microporation, biolistic bombardment, bacterial protoplast fusion with intact cells, or polycations, e.g., polybrene, polyornithine, may also be used.

Suitable host cells for cloning or expressing the DNA in the vectors herein include prokaryote, yeast, or filamentous fungal cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). In addition to prokaryotes, eukaryotic microorganisms such as filamentous fungi or yeast are suitable cloning or expression hosts for vectors encoding Bhe Man2 polypeptides. *Saccharomyces cerevisiae* is a commonly used lower eukaryotic host microorganism.

In some embodiments, the microorganism to be transformed includes a strain derived from *Trichoderma* sp. or *Aspergillus* sp. Exemplary strains include *T. reesei* which is useful for obtaining overexpressed protein or *Aspergillus niger* var. *awamori*. For example, *Trichoderma* strain RL-P37, described by Sheir-Neiss et al. in *Appl. Microbiol. Biotechnology*, 20 (1984) pp. 46-53 is known to secrete elevated amounts of cellulase enzymes. Functional equivalents of RL-P37 include *Trichoderma reesei* (*longibrachiatum*) strain RUT-C30 (ATCC No. 56765) and strain QM9414 (ATCC No. 26921). Another example includes overproducing mutants as described in Ward et al. in *Appl. Microbiol. Biotechnology* 39:738-743 (1993). For example, it is contemplated that these strains would also be useful in overexpressing a *Bacillus hemicellulosilyticus* Bhe Man2 polypeptide, or a variant thereof. The selection of the appropriate host cell is deemed to be within the skill in the art.

Preparation and Use of a Replicable Vector

DNA encoding the Bhe Man2 protein or derivatives thereof (as described above) is prepared for insertion into an appropriate microorganism. According to the present compositions and methods, DNA encoding a Bhe Man2 polypeptide includes all of the DNA necessary to encode for a protein which has functional Bhe Man2 activity. As such, embodiments of the present compositions and methods include DNA encoding a Bhe Man2 polypeptide derived from *Bacillus* sp., including, *Bacillus hemicellulosilyticus*.

The DNA encoding Bhe Man2 may be prepared by the construction of an expression vector carrying the DNA encoding Bhe Man2. The expression vector carrying the inserted DNA fragment encoding the Bhe Man2 may be any vector which is capable of replicating autonomously in a given host organism or of integrating into the DNA of the host, typically a plasmid, cosmid, viral particle, or phage. Various vectors are publicly available. It is also contemplated that more than one copy of DNA encoding a Bhe Man2 may be recombined into the strain to facilitate overexpression.

In certain embodiments, DNA sequences for expressing Bhe Man2 include the promoter, gene coding region, and terminator sequence all originate from the native gene to be expressed. Gene truncation may be obtained by deleting away undesired DNA sequences (e.g., coding for unwanted domains) to leave the domain to be expressed under control of its native transcriptional and translational regulatory sequences. A selectable marker can also be present on the vector allowing the selection for integration into the host of multiple copies of the Bhe Man2 gene sequences.

In other embodiments, the expression vector is preassembled and contains sequences required for high level transcription and, in some cases, a selectable marker. It is contemplated that the coding region for a gene or part thereof can be inserted into this general purpose expression vector such that it is under the transcriptional control of the expression cassette's promoter and terminator sequences. For example, pTEX is such a general purpose expression vector. Genes or part thereof can be inserted downstream of the strong cbh1 promoter.

In the vector, the DNA sequence encoding the Bhe Man2 of the present compositions and methods should be operably linked to transcriptional and translational sequences, e.g., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular production (secretion) of the Bhe Man2 or derivatives thereof. The DNA encoding the signal sequence can be that which is naturally associated with the gene to be expressed. However the signal sequence from any suitable source, for example an exo-cellobiohydrolases or endoglucanase from *Trichoderma*, a xylanase from a bacterial species, e.g., from *Streptomyces coelicolor*, etc., are contemplated in the present compositions and methods.

The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

A desired Bhe Man2 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector or it may be a part of the Bhe Man2-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990.

Both expression and cloning vectors may contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria and the 2μ plasmid origin is suitable for yeast.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. A suitable selection gene for use in yeast is the trp1 gene present in the yeast plasmid YRp7 (Stinchcomb et al., *Nature*, 282:39 (1979); Kingsman et al., *Gene*, 7:141 (1979); Tschemper et al., *Gene*, 10:157 (1980)). The trp1 gene provides a selection marker for a mutant strain of yeast lacking the ability to grow in tryptophan, for example, ATCC No. 44076 or PEP4-1 (Jones, *Genetics*, 85:12 (1977)). An exemplary selection gene for use in *Trichoderma* sp is the pyr4 gene.

Expression and cloning vectors usually contain a promoter operably linked to the Bhe Man2-encoding nucleic acid sequence. The promoter directs mRNA synthesis. Promoters recognized by a variety of potential host cells are well known. Promoters include a fungal promoter sequence, for example, the promoter of the cbh1 or egl1 gene.

Promoters suitable for use with prokaryotic hosts include the β-lactamase and lactose promoter systems (Chang et al., *Nature*, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter (deBoer et al., *Proc. Natl. Acad. Sci. USA*, 80:21-25 (1983)). Additional promoters, e.g., the A4 promoter from *A. niger*, also find use in bacterial expression systems, e.g., in *S. lividans*. Promoters for use in bacterial systems also may contain a Shine-Dalgarno (S.D.) sequence operably linked to the DNA encoding a Bhe Man2 polypeptide.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Expression vectors used in eukaryotic host cells (e.g. yeast, fungi, insect, plant) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding a Bhe Man2 polypeptide.

Purification of a Bhe Man2 Polypeptide

Forms of Bhe Man2 polypeptides (or Bhe Man2 polypeptide derivatives) may be recovered from culture medium or from host cell lysates by the methods described above for isolation and purification from natural isolates. Additional techniques can be used depending on the host cell employed and any variant structures in the recombinant enzyme. For example, if the recombinant enzyme is membrane-bound, it can be released from the membrane using a suitable detergent solution (e.g. Triton-X 100) or by enzymatic cleavage. Purification of recombinant enzyme may also employ protein A Sepharose columns to remove contaminants such as IgG and metal chelating columns to bind epitope-tagged forms of the Bhe Man2 polypeptide. The purification step(s) selected will depend, for example, on the nature of the production process used, the particular Bhe Man2 polypeptide that is produced, and any variant structure for the recombinant enzyme. Antibodies directed to a Bhe Man2 polypeptide or epitope tags thereon may also be employed to purify the protein, e.g., anti-Bhe Man2 antibodies attached to a solid support.

4. Derivatives of Bhe Man2

As described above, in addition to the native sequence of Bhe Man2 described herein (e.g., as depicted in full length as SEQ ID NO:2, and in the mature form as SEQ ID NO:3), it is contemplated that Bhe Man2 derivatives can be prepared with altered amino acid sequences. In general, Bhe Man2 derivatives would be capable of conferring, as a native Bhe Man2 polypeptide, to a cellulase and/or hemicellulase mixture or composition either one or both of an improved capacity to hydrolyze a lignocellulosic biomass substrate, in particular one that is mannan-containing, and an improved capacity to reduce viscosity of a biomass substrate mixture, particularly one that is at a high solids level. Such derivatives may be made, for example, to improve expression in a particular host, improve secretion (e.g., by altering the signal sequence), to introduce epitope tags or other sequences that can facilitate the purification and/or isolation of Bhe Man2 polypeptides. In some embodiments, derivatives may confer more capacity to hydrolyze a lignocellulosic biomass substrate to a cellulase and/or hemicellulase mixture or compostion, as compared to the native Bhe Man2 polypeptide. In some embodiments, derivatives may confer a higher viscosity reduction benefit (e.g., an improvement or even higher speed and/or extent of viscosity reduction) to a cellulase and/or hemicellulase mixture, as compared to the native Bhe Man2 polypeptide.

Bhe Man2 polypeptide derivatives can be prepared by introducing appropriate nucleotide changes into the Bhe Man2-encoding DNA, or by synthesis of the desired Bhe Man2 polypeptides. Those skilled in the art will appreciate that amino acid changes may alter post-translational processes of the Bhe Man2 polypeptides, such as changing the number or position of glycosylation sites.

Derivatives of the native sequence Bhe Man2 polypeptide or of various domains of the Bhe Man2 described herein can be made, for example, using any of the techniques and guidelines for conservative and non-conservative mutations set forth, for instance, in U.S. Pat. No. 5,364,934. Sequence variations may be a substitution, deletion or insertion of one or more codons encoding the Bhe Man2 polypeptide that results in a change in the amino acid sequence of the Bhe Man2 polypeptide as compared with the native sequence Bhe Man2 polypeptide. Optionally, the sequence variation is by substitution of at least one amino acid with any other amino acid in one or more of the domains of the Bhe Man2 polypeptide.

Guidance in determining which amino acid residue may be inserted, substituted or deleted without adversely affecting the desired Bhe Man2 beta-mannanase activity may be found by comparing the sequence of the polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting derivatives for functional activity using techniques known in the art.

The sequence variations can be made using methods known in the art such as oligonucleotide-mediated (site-directed) mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London SerA*, 317:415 (1986)) or other known techniques can be performed on the cloned DNA to produce the Bhe Man2-encoding DNA with a variant sequence.

Scanning amino acid analysis can also be employed to identify one or more amino acids along a contiguous sequence. Among the scanning amino acids the can be employed are relatively small, neutral amino acids. Such amino acids include alanine, glycine, serine, and cysteine. Alanine is often used as a scanning amino acid among this group because it eliminates the side-chain beyond the beta-carbon and is less likely to alter the main-chain conformation of the derivative. Alanine is also often used because it is the most common amino acid. Further, it is frequently found in both buried and exposed positions (Creighton, *The Proteins*, (W.H. Freeman & Co., N.Y.); Chothia, *J. Mol. Biol.*, 150:1 (1976)). If alanine substitution does not yield adequate amounts of derivative, an isosteric amino acid can be used.

5. Anti-Bhe Man2 Antibodies

The present compositions and methods further provide anti-Bhe Man2 antibodies. Exemplary antibodies include polyclonal and monoclonal antibodies, including chimeric and humanized antibodies.

The anti-Bhe Man2 antibodies of the present compositions and methods may include polyclonal antibodies. Any convenient method for generating and preparing polyclonal and/or monoclonal antibodies may be employed, a number of which are known to those ordinarily skilled in the art.

Anti-Bhe Man2 antibodies may also be generated using recombinant DNA methods, such as those described in U.S. Pat. No. 4,816,567.

The antibodies may be monovalent antibodies, which may be generated by recombinant methods or by the digestion of antibodies to produce fragments thereof, particularly, Fab fragments.

D. Cell Culture Media

Generally, the microorganism is cultivated in a cell culture medium suitable for production of the Bhe Man2 polypeptides described herein. The cultivation takes place in a suitable nutrient medium comprising carbon and nitrogen sources and inorganic salts, using procedures and variations known in the art. Suitable culture media, temperature ranges and other conditions for growth and cellulase production are known in the art. As a non-limiting example, a typical temperature range for the production of cellulases by *Trichoderma reesei* is 24° C. to 37° C., for example, between 25° C. and 30° C.

a. Cell Culture Conditions

Materials and methods suitable for the maintenance and growth of fungal cultures are well known in the art. In some aspects, the cells are cultured in a culture medium under conditions permitting the expression of one or more beta-mannanase polypeptides encoded by a nucleic acid inserted into the host cells. Standard cell culture conditions can be used to culture the cells. In some aspects, cells are grown and maintained at an appropriate temperature, gas mixture, and pH. In some aspects, cells are grown at in an appropriate cell medium.

6. Compositions Comprising a Recombinant Beta-Mannanase Bhe Man2 Polypeptide The present disclosure provides engineered enzyme compositions (e.g., cellulase compositions) or fermentation broths enriched with a recombinant Bhe Man2 polypeptides. In some aspects, the composition is a cellulase composition. The cellulase composition can be, e.g., a filamentous fungal cellulase composition, such as a *Trichoderma* cellulase composition. The cellulase composition can be, in some embodiments, an admixture or physical mixture, of various cellulases originating from different microorganisms; or it can be one that is the culture broth of a single engineered microbe co-expressing the celluase genes; or it can be one that is the admixture of one or more individually/separately obtained cellulases with a mixture that is the culture broth of an engineered microbe co-expressing one or more cellulase genes.

In some aspects, the composition is a cell comprising one or more nucleic acids encoding one or more cellulase polypeptides. In some aspects, the composition is a fermentation broth comprising cellulase activity, wherein the broth is capable of converting greater than about 50% by weight of the cellulose present in a biomass sample into sugars. The term "fermentation broth" and "whole broth" as used herein refers to an enzyme preparation produced by fermentation of an engineered microorganism that undergoes no or minimal recovery and/or purification subsequent to fermentation. The fermentation broth can be a fermentation broth of a filamentous fungus, for example, a *Trichoderma, Humicola, Fusarium, Aspergillus, Neurospora, Penicillium, Cephalosporium, Achlya, Podospora, Endothia, Mucor, Cochliobolus, Pyricularia, Myceliophthora* or *Chrysosporium* fermentation broth. In particular, the fermentation broth can be, for example, one of *Trichoderma* sp. such as a *Trichoderma reesei*, or *Penicillium* sp., such as a *Penicillium funiculosum*. The fermentation broth can also suitably be a cell-free fermentation broth. In one aspect, any of the cellulase, cell, or fermentation broth compositions of the present invention can further comprise one or more hemicellulases.

In some aspects, the whole broth composition is expressed in *T. reesei* or an engineered strain thereof. In some aspects the whole broth is expressed in an integrated strain of *T. reesei* wherein a number of cellulases including a Bhe Man2 polypeptide has been integrated into the genome of the *T. reesei* host cell. In some aspects, one or more components of the polypeptides expressed in the integrated *T. reesei* strain have been deleted.

In some aspects, the whole broth composition is expressed in *A. niger* or an engineered strain thereof.

Alternatively, the recombinant Bhe Man2 polypeptides can be expressed intracellularly. Optionally, after intracellular expression of the enzyme variants, or secretion into the periplasmic space using signal sequences such as those mentioned above, a permeabilisation or lysis step can be used to release the recombinant Bhe Man2 polypeptide into the supernatant. The disruption of the membrane barrier is effected by the use of mechanical means such as ultrasonic waves, pressure treatment (French press), cavitation, or by the use of membrane-digesting enzymes such as lysozyme or enzyme mixtures.

In some aspects, the polynucleotides encoding the recombinant Bhe Man2 polypeptide are expressed using a suitable cell-free expression system. In cell-free systems, the polynucleotide of interest is typically transcribed with the assistance of a promoter, but ligation to form a circular expression vector is optional. In some embodiments, RNA is exogenously added or generated without transcription and translated in cell-free systems.

7. Uses of Bhe Man2 Polypeptides to Hydrolyze a Lignocellulosic Biomass Substrate In some aspects, provided herein are methods for converting lignocelluloses biomass to sugars, the method comprising contacting the biomass substrate with a composition disclosed herein comprising a Bhe Man2 polypeptide in an amount effective to convert the biomass substrate to fermentable sugars. Suitably the biomass substrate comprises GGM and/or GM. In certain embodiments, a suitable biomass substrate may contain up to about 2 wt. % or more, about 3 wt. % or more, about 4 wt. % or more, about 5 wt. % or more, etc. of GGM and/or GM.

In some aspects, the method further comprises pretreating the biomass with acid and/or base and/or mechanical or other physical means In some aspects the acid comprises phosphoric acid. In some aspects, the base comprises sodium hydroxide or ammonia. In some aspects, the mechanical means may include, for example, pulling, pressing, crushing, grinding, and other means of physically breaking down the lignocellulosic biomass into smaller physical forms. Other physical means may also include, for example, using steam or other pressurized fume or vapor to "loosen" the lignocellulosic biomass in order to increase accessibility by the enzymes to the cellulose and hemicellulose. In certain embodiments, the method of pretreatment may also involve enzymes that are capable of breaking down the lignin of the lignocellulosic biomass substrate, such that the accessibility of the enzymes of the biomass hydrolyzing enzyme composition to the cellulose and the hemicelluloses of the biomass is increased.

Biomass:

The disclosure provides methods and processes for biomass saccharification, using the enzyme compositions of the disclosure, comprising a Bhe Man2 polypeptide. The term "biomass," as used herein, refers to any composition comprising cellulose and/or hemicellulose (optionally also lignin in lignocellulosic biomass materials). Particularly suitable are lignocellulosic biomass materials comprising measureable amounts of galactoglucomannans (GGMs) and/or glucomannan (GMs). Such biomass materials may include, for example, a KRAFT-alkaline pretreated industrial unbleached softwood pulp, FPP-27, which can be obtained from Agence Nationale de la Recherche, France, which contains about 6.5 wt. % mannan; a SPORL-pretreated softwood (Zhu J. Y. et al., (2010) Appl. Microbiol. Biotechnol. 86(5):1355-65; Tian S. et al., (2010) Bioresour. Technol. 101:8678-85), which contains about 4.5 wt. % mannan; spruce, which may contain over 10 wt. % of mannan. As used herein, biomass includes, without limitation, certain softwood trees such as spruce, pine, aspen trees, and wastes derived therefrom, seeds, grains, tubers, plant waste (such as, for example, empty fruit bunches of the palm trees, or palm fibre wastes) or byproducts of food processing or industrial processing (e.g., stalks), corn (including, e.g., cobs, stover, and the like), grasses (including, e.g., Indian grass, such as *Sorghastrum nutans*; or, switchgrass, e.g., *Panicum* species, such as *Panicum virgatum*), perennial canes (e.g., giant reeds), wood (including, e.g., wood chips, processing waste), paper, pulp, and recycled paper (including, e.g., newspaper, printer paper, and the like). Other biomass materials include, without limitation, potatoes, soybean (e.g., rapeseed), barley, rye, oats, wheat, beets, and sugar cane bagasse.

The disclosure therefore provides methods of saccharification comprising contacting a composition comprising a biomass material, for example, a material comprising xylan, hemicellulose, and in particular, galactoglucomannans (GGMs) and/or glucomannans (GMs), cellulose, and/or a fermentable sugar, with a Bhe Man2 polypeptide of the disclosure, or a Bhe Man2 polypeptide encoded by a nucleic acid or polynucleotide of the disclosure, or any one of non-naturally occurring the cellulase and/or hemicellulase compositions comprising a Bhe Man2 polypeptide, or products of manufacture of the disclosure.

The saccharified biomass (e.g., lignocellulosic material processed by enzymes of the disclosure) can be made into a number of bio-based products, via processes such as, e.g., microbial fermentation and/or chemical synthesis. As used herein, "microbial fermentation" refers to a process of growing and harvesting fermenting microorganisms under suitable conditions. The fermenting microorganism can be any microorganism suitable for use in a desired fermentation process for the production of bio-based products. Suitable fermenting microorganisms include, without limitation, filamentous fungi, yeast, and bacteria. The saccharified biomass can, for example, be made it into a fuel (e.g., a biofuel such as a bioethanol, biobutanol, biomethanol, a biopropanol, a biodiesel, a jet fuel, or the like) via fermentation and/or chemical synthesis. The saccharified biomass can, for example, also be made into a commodity chemical (e.g., ascorbic acid, isoprene, 1,3-propanediol), lipids, amino acids, polypeptides, and enzymes, via fermentation and/or chemical synthesis.

Pretreatment:

Prior to saccharification or enzymatic hydrolysis and/or fermentation of the fermentable sugars resulting from the saccharifiction, biomass (e.g., lignocellulosic material) is preferably subject to one or more pretreatment step(s) in order to render xylan, hemicellulose, cellulose and/or lignin material more accessible or susceptible to the enzymes in the enzymatic composition (for example, the enzymatic composition of the present invention comprising a Bhe Man2 polypeptide) and thus more amenable to hydrolysis by the enzyme(s) and/or the enzyme compositions.

In some aspects, a suitable pretreatment method may involve subjecting biomass material to a catalyst comprising a dilute solution of a strong acid and a metal salt in a reactor. The biomass material can, e.g., be a raw material or a dried material. This pretreatment can lower the activation energy, or the temperature, of cellulose hydrolysis, ultimately allowing higher yields of fermentable sugars. See, e.g., U.S. Pat. Nos. 6,660,506; 6,423,145.

In some aspects, a suitable pretreatment method may involve subjecting the biomass material to a first hydrolysis step in an aqueous medium at a temperature and a pressure chosen to effectuate primarily depolymerization of hemicellulose without achieving significant depolymerization of cellulose into glucose. This step yields a slurry in which the liquid aqueous phase contains dissolved monosaccharides resulting from depolymerization of hemicellulose, and a solid phase containing cellulose and lignin. The slurry is then subject to a second hydrolysis step under conditions that allow a major portion of the cellulose to be depolymerized, yielding a liquid aqueous phase containing dissolved/soluble depolymerization products of cellulose. See, e.g., U.S. Pat. No. 5,536,325.

In further aspects, a suitable pretreatment method may involve processing a biomass material by one or more stages of dilute acid hydrolysis using about 0.4% to about 2% of a strong acid; followed by treating the unreacted solid lignocellulosic component of the acid hydrolyzed material with alkaline delignification. See, e.g., U.S. Pat. No. 6,409,841.

In yet further aspects, a suitable pretreatment method may involve pre-hydrolyzing biomass (e.g., lignocellulosic materials) in a pre-hydrolysis reactor; adding an acidic liquid to the solid lignocellulosic material to make a mixture; heating the mixture to reaction temperature; maintaining reaction temperature for a period of time sufficient to fractionate the lignocellulosic material into a solubilized portion containing at least about 20% of the lignin from the lignocellulosic material, and a solid fraction containing cellulose; separating the solubilized portion from the solid fraction, and removing the solubilized portion while at or near reaction temperature; and recovering the solubilized portion. The cellulose in the solid fraction is rendered more amenable to enzymatic digestion. See, e.g., U.S. Pat. No. 5,705,369. In a variation of this aspect, the pre-hydrolyzing can alternatively or further involve pre-hydrolysis using enzymes that are, for example, capable of breaking down the lignin of the lignocellulosic biomass material.

In yet further aspects, suitable pretreatments may involve the use of hydrogen peroxide $H_2O_2$. See Gould, 1984, Biotech. and Bioengr. 26:46-52.

In further aspects, suitable pretreatment of the lignocellulosic biomass materials, in particular those comprising measurable amounts of galactoglucomannans (GGMs) and/or glucomannans (GMs), may include the KRAFT alkaline pretreatment method employed by, for example, the Agence Nationale de la Recherche, France. The KRAFT pretreatment method is a well-known and widely used method to convert wood into wood pulp, typically including the treatment of wood chips with a mixture of sodium hydroxide and sodium sulfide, known in the industry as "white liquor," which breaks down the bonds that link lignin to the cellulose. It is a long-practiced method, mostly in the paper and pulp industry, originally invented by Carl F. Dahl in 1879, as described in U.S. Pat. No. 296,935, issued in 1884. Also included are the SPORL pretreatment method developed by the United States Department of Agriculture specifically for certain softwood biomass feedstocks, for example, for pine, spruce and aspen tree materials, such as described in Zhu et al., (2009) Bioresource Technol. 100:2411-18. The SPORL pretreatment method involves using sulfite to treat wood chips of such softwoods under acidic conditions followed by mechanical size reduction using disk refining. The SPORL method was reported to produce a reduced amount of fermentation inhibitors such as hydroxyl-methyl furfural and/or furfural.

In other aspects, pretreatment can also comprise contacting a biomass material with stoichiometric amounts of sodium hydroxide and ammonium hydroxide at a very low concentration. See Teixeira et al., (1999), Appl. Biochem. and Biotech. 77-79:19-34.

In some embodiments, pretreatment can comprise contacting a lignocellulose with a chemical (e.g., a base, such as sodium carbonate or potassium hydroxide) at a pH of about 9 to about 14 at moderate temperature, pressure, and pH. See Published International Application WO2004/081185. Ammonia is used, for example, in a preferred pretreatment method. Such a pretreatment method comprises subjecting a biomass material to low ammonia concentration under conditions of high solids. See, e.g., U.S. Patent Publication No. 20070031918 and Published International Application WO 06110901.

A. The Saccharification Process

In some aspects, provided herein is a saccharification process comprising treating a lignocellulosic biomass material, in particular, one comprising a measurable amount of galactoglucomannans (GGMs) and/or glucomannans (GMs), with an enzyme composition comprising a polypeptide, wherein the polypeptide has beta-mannanase activity and wherein the process results in at least about 50 wt. % (e.g., at least about 55 wt. %, 60 wt. %, 65 wt. %, 70 wt. %, 75 wt. %, or 80 wt. %) conversion of the biomass to fermentable sugars. In some aspects, the biomass comprises lignin. In some aspects the biomass comprises cellulose. In some aspects the biomass comprises hemicelluloses. In some aspects, the biomass comprising cellulose further comprises one or more of mannan, xylan, galactan, and/or arabinan. In certain particular aspects, the biomass comprising cellulose as well as at least a measurable level of galactoglucomannan and/or glucomannan. In some aspects, the biomass may be, without limitation, softwood plants (e.g., pine, spruce, aspen trees), seeds, grains, tubers, plant waste (e.g., empty fruit bunch from palm trees, or palm fibre waste) or byproducts of food processing or industrial processing (e.g., stalks), corn (including, e.g., cobs, stover, and the like), grasses (including, e.g., Indian grass, such as *Sorghastrum nutans*; or, switchgrass, e.g., *Panicum* species, such as *Panicum virgatum*), perennial canes (e.g., giant reeds), woody materials (including, e.g., wood chips, processing waste), paper, pulp, and recycled paper (including, e.g., newspaper, printer paper, and the like), potatoes, soybean (e.g., rapeseed), barley, rye, oats, wheat, beets, and sugar cane bagasse.

In some aspects, the material comprising biomass is subject to one or more pretreatment methods/steps prior to treatment with the Bhe Man2 polypeptide or the composition comprising the Bhe Man2 polypeptide. In some aspects, the saccharification or enzymatic hydrolysis further comprises treating the biomass with an enzyme composition comprising a Bhe Man2 polypeptide of the invention. The enzyme composition may, for example, comprise one or more cellulases, for example, one or more endoglucanases, one or more cellobiohydrolases, and/or one or more beta-glucosidases, in addition to the Bhe Man2 polypeptide. Alternatively, the enzyme composition may comprise one or more other hemicellulases, for example, one or more other beta-mannanases, one or more xylanases, one or more beta-xylosidases, and/or one or more L-arabinofuranosidases. In certain embodiments, the enzyme composition comprises a Bhe Man2 polypeptide of the invention, one or more cellulases, one or more other hemicellulases. In some embodiments, the enzyme composition is a fermentation broth composition, optionally subject to some post-production/fermentation processing. In certain embodiments, the enzyme composition is a whole broth formulation.

In some aspects, provided is a saccharification process comprising treating a lignocellulosic biomass material with a composition comprising a polypeptide, wherein the polypeptide has at least about 70% (e.g., at least about 70%, 75%, 80%, 85%, 90%, 91%, 92%, 93%, 94%, 95%, 96%, 97%, 98%, 99%) sequence identity to SEQ ID NO:2, or to the mature sequence of SEQ ID NO:3, and wherein the process results in at least about 50% (e.g., at least about 55%, 60%, 65%, 70%, 75%, 80%, 85%, or 90%) by weight conversion of biomass to fermentable sugars. In some aspects, lignocellulosic biomass material has been subject to one or more pretreatment methods/steps as described herein.

Other aspects and embodiments of the present compositions and methods will be apparent from the foregoing description and following examples.

EXAMPLES

The following examples are put forth so as to provide those of ordinary skill in the art with a complete disclosure and description of how to make and use the present compositions and methods, and are not intended to limit the scope of what the inventors regard as their inventive compositions and methods nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Cloning of *Bacillus Hemicellulosilyticus* Glycosyl Hydrolase Bhe Man2

*Bacillus hemicellulosilyticus* was selected as a potential source for various glycosyl hydrolases and other enzymes, useful for industrial applications. Genomic DNA for sequencing was obtained by first growing a strain of *Bacillus hemicellulosilyticus* on LB agar plates at 37° C. for 24 hours. Cell material was scraped from the plates and used to prepare genomic DNA using phenol/chloroform extraction. The genomic DNA was used for sequencing and to amplify the bhe Man2 gene for expression cloning. The entire genome of *Bacillus hemicellulosilyticus* was sequenced using Illumina® sequencing by synthesis (SBS) technology (website: baseclear.com/sequencing/illumina-sequencing. Genome sequencing and assembly of the sequence data was performed by BaseClear (Leiden, The Netherlands). Contigs were annotated by BioXpr (Namur, Belgium). The nucleic acid sequence of the bhe Man2 gene was identified using homology alignments by BLASTP to other mannanases from bacteria.

The nucleic acid sequence of this gene, bhe Man2, is listed as SEQ ID NO:1. The amino acid sequence of the protein encoded by the bhe Man2 gene is listed as SEQ ID NO:2. At the N-terminus, the protein is predicted to have a signal peptide with a length of 32 amino acids as determined by the Signal P 3.0 program (website: cbs.dtu/services/SignalP) set to SignalP-NN system (Emanuelsson et al., Nature Protocols, 2: 953-971, 2007). The presence of a signal sequence suggests that Bhe Man2 is a secreted glycosyl hydrolase.

Example 2

Expression of *Bacillus Hemicellulosilyticus* Bhe Man2 in *Bacillus subtilis* Host The Bhe Man2 gene was amplified by PCR from *Bacillus hemicellulosilyticus* genomic DNA using the following primers:

```
Primer 1 (BssHII)
                                      (SEQ ID NO: 7)
5'-TGAGCGCGCA GGCTGCTGGA AAAAGTTCAG
GCTTTTATGT TGATGG-3'

Primer 2 (BamHI)
                                      (SEQ ID NO: 8)
5'-CGCGGATCCT TATCTTAAAG TAACATTATC
AACGTATAG-3'
```

The forward primer contains part of the aprE signal sequence and the starting sequence of the mature Bhe Man2 chain. The reverse primer contains the end of the gene sequence, stop codon, the BamHI site, and 3 extra protecting codons. This amplified bhe Man2 gene was cloned into the expression plasmid p2JM by BssHII/BamHI double digestion and ligation. The *Bacillus subtilis* expression vector p2JM103BBI (Vogtentanz, *Protein Expr Purif,* 55:40-52, 2007) was digested with the restriction enzymes BssHII and BamHI. Ligation of this DNA fragment to the PCR amplified gene encoding the bhe Man2 mature protein resulted in the addition of three codons, Ala-Gly-Lys, between the 3' end of the *Bacillus subtilis* AprE pro-peptide and the 5' end of the bhe Man2 gene. The resulting plasmid was labeled pML356 (aprE-BhcnmanA). Following the signal peptidase cleavage in the host, the recombinant Bhe Man2 polypeptide produced in this manner would have 3 additional amino acids, Ala-Gly-Lys, at its amino-terminus.

The sequence of the bhe Man2 gene expressed from the pML356 was confirmed by DNA sequencing (SEQ ID NO:9). The amino acid sequence of the Bhe Man2 polypeptide expressed from the plasmid pML356 is set forth as SEQ ID NO:10, with the signal sequence shown in italics and the three additional residues shown in bold. The amino acid sequence of Bhe Man3 mature polypeptide expressed from the pML356 is set forth as SEQ ID NO:11, with the three residues amino-terminal extension based on the predicted cleavage site shown in bold. After the terminal extension residues were cleaved, the mature Bhe Man2 polypeptide has the sequence of SEQ ID NO:12.

The Bhe Man2 polypeptide was produced in *Bacillus subtilis* host cells, as described above, and was secreted into the extracellular culture medium after expression was complete. Accordingly the expression culture medium was filtered and concentrated, and used for protein purification.

Example 3

Purification of Beta-Mannanase Bhe Man2 from a Culture Medium of *Bacillus subtilis*

Ammonium sulphate was first added to concentrated supernatant to a final concentration of 1.0 M. Purification of Bhe Man2 from the filtered and concentrated culture medium supernatant then took place using three different chromatography columns: (1) a 20-mL phenyl Sepharose Fast Flow column pre-equilibrated with 20 mM Tris-HCL buffer, pH 8.0, containing 1 M ammonium sulphate, which was eluted with a linear salt gradient from 1 M to 0 M ammonium sulphate in a 20 mM Tris-HCl buffer at pH 8.0; (2) the active fractions in the eluate of column (1) were collected and desalted into a 20 mM Tris-HCl buffer, pH 8.0, before loading onto a 20 mL Q sepharose Fast Flow column pre-equilibrated with a 20 mM Tris-HCl buffer, pH 8.0, which was eluted with a linear salt gradient from 0 to 0.5 M NaCl in the loading buffer; and (3) the active fractions in the eluate of column (2) were collected, and ammonium sulphate was added to such collected fractions a final concentration of 1 M, and the collected fractions were filtered, and applied to a 20 mL phenyl Sepharose Fast Flow column pre-equilibrated with a 20 mM Tris-HCl buffer, pH 8.0, containing 1 M ammonium sulphate, which was then eluted with a linear salt gradient from 1 M to 0 M of ammonium sulphate in 20 mM Tris-HCl buffer, pH 8.0.

The purity of the polypeptide was determined using SDS-PAGE, and the predicted molecular weight of Bhe Man2 polypeptide, which has 464 amino acid residues and an estimated molecular weight of about 51 kDa, was used to confirm the identity of the Bhe Man2 polypeptide. The purified Bhe Man2 polypeptide was used to perform the pH profile, temperature profile, and thermostability profile studies below.

Example 4

Expression of *Bacillus Hemicellulosilyticus* Beta-Mannanase Bhe Man2 in a *T. reesei* Host The Bhe Man2 gene can be amplified from *Bacillus hemicellulosilyticus* genomic DNA using PCR, with the native signal sequence and a CACC sequence added to the 5' end of the forward primer for directional Gateway cloning (Invitrogen, Carlsbad, Calif.). Alternatively, a *T. reesei* cbhI signal sequence might be employed, substituting for the native signal sequence. The PCR product of the bhe Man2 gene can be purified using a Qiaquick PCR Purification Kit (Qiagen). The purified PCR product can then be cloned into the pENTR/D-TOPO vector, transformed into One Shot® TOP10 Chemically Competent *E. coli* cells (Invitrogen), and then plated onto LA plates containing 50 ppm kanamycin. Plasmid DNA can then be obtained from the *E. coli* transformants, using a QIAspin plasmid preparation kit (Qiagen).

The nucleotide sequence of the inserted DNA can then be confirmed as SEQ ID NO:1 using well-known sequencing methods. The pENTR/D-TOPO_Bhe Man2 vector including the confirmed bhe Man2 gene sequence can then be recombined with the expression vector pTrex3gM (see, e.g., International Published Patent Application WO 05/001036, FIG. 2), using an LR Clonase® reaction (see, protocols by Invitrogen).

The product of the LR Clonase® reaction (i.e., the vector pTrex3gM_Bhe Man2) can then be transformed into *E. coli* One Shot® TOP10 Chemically Competent cells (Invitrogen) and plated on LA medium containing 50 ppm carbenicillin. The pTrex3gM vector also contains the *Aspergillus tubingensis* amdS gene, encoding acetamidase, as a selectable marker for transformation of *T. reesei*. The pTrex3gM vector further contains a cbhI promoter and terminator, which flank the bhe Man2 sequence.

Thereafter, about 0.5 to 1 µg of the expression vector pTrex3gM_Bhe Man2 (or a fragment amplified by PCR) can be used to transform a *T. reesei* strain with its major cellulase genes deleted, for example, a six-fold deletion strain as described in, e.g., in International Patent Application Publication No. WO 2010/141779), using the PEG-protoplast method with modifications as described herein.

For protoplast preparation, spores can be grown for 16-24 hours at 24° C. in a *Trichoderma* Minimal Medium MM, containing 20 g/L glucose, 15 g/L $KH_2PO_4$, pH 4.5, 5 g/L $(NH_4)_2SO_4$, 0.6 g/L $MgSO_4 \times 7H_2O$, 0.6 g/L $CaCl_2 \times 2H_2O$, 1 mL of 1000× *T. reesei* Trace elements solution (5 g/L $FeSO_4 \times 7H_2O$, 1.4 g/L $ZnSO_4 \times 7H_2O$, 1.6 g/L $MnSO_4 \times H_2O$, 3.7 g/L $CoCl_2 \times 6H_2O$) with shaking at 150 rpm. Germinating spores can then be harvested by centrifugation and treated with 50 mg/mL of Glucanex G200 (Novozymes AG) solution to lyse the fungal cell walls. Further preparation of the protoplasts can be performed in accordance with a method described by Penttila et al. Gene 61(1987)155-164. The transformation mixture, containing about 1 µg of DNA and at least $1 \times 10^7$ protoplasts in a total volume of 200 µL, can then be treated with 2 mL of 25% PEG solution, diluted with 2 volumes of 1.2 M sorbitol/10 mM Tris, pH7.5, 10 mM $CaCl_2$, mixed with 3% selective top agarose MM containing 20 mM acetamide. The resulting mixture is then poured onto 2% selective agarose plate containing acetamide. Followed by that, plates are incubated for 7-10 days at 28° C. Single transformants are then transferred onto fresh MM plates containing acetamide. Spores from independent clones are then used to inoculate a fermentation medium in either 96-well microtiter plates or shake flasks.

Secreted protein from the culture broths can be purified, optionally subject to some post-fermentation processing, or can be used directly for saccharification or hydrolyzing mannan-containing lignocellulosic biomass substrates

Example 5

The Beta-Mannanase Activity of Bhe Man2

The beta-1,4 mannanase activity of Bhe Man2 was measured using 1% galactomannan (Carob; Low Viscosity) (P-GALML; Lot 10501) purchased from Megazyme International Ireland (Bray, Ireland) as a substrate. The assay was performed in a 50 mM sodium acetate buffer, pH 5.0, containing 0.005% Tween-80, whereby the polypeptide and the substrate were incubated at 50° C. for 10 minutes. Alternatively the assay was performed in a 50 mM HEPES buffer, pH 8.2, containing 0.005% Tween-80, whereby the polypeptide and the substrate were incubated at 30° C. for 30 minutes.

The reducing sugar(s) released from the hydrolysis reaction was quantified using a PAHBAH (p-Hydroxy benzoic acid hydrazide) assay as described by Lever (1972) *Anal. Biochem.* 47:248. A standard curve was prepared using various amounts of mannose as standards, and the specific enzyme activity units were calculated. Specifically one mannanase unit was defined as the amount of enzyme required to generate 1 micromole of mannose reducing sugar equivalents per minute under a given set of conditions.

As measured, the specific activity of the purified Bhe Man2 polypeptide was about 22 units/mg at pH 5.0, and about 46 units/mg at pH 8.2.

Example 6

The pH Profile of Bhe Man2

Activity assays were performed in a sodium citrate/sodium phosphate buffer, having various pH values in a range between pH 2 and pH 9. Twenty five (25) µL of a 0.5 M sodium citrate/sodium phosphate buffer was added to 65 µL of locust bean gum (1% aqueous solution) in a 96-well plate, and the substrate was equilibrated at the assay temperature of 50° C. prior to the addition of enzyme. After carrying on for 10 minutes, the enzyme reaction was stopped by transferring 10 µL of the reaction mixture to a 96-well PCR plate well, which contained 100 µL of PAHBAH solution. The PCR plate was then incubated at 95° C. for 5 minutes in a Bio-Rad DNA Engine. The PCR plate was subsequently cooled on ice and 100 µL of the mixture in the well was transferred to a new 96-well assay plate.

The amount of reducing sugar(s) released from the substrate was determined by measuring the optical density of the reaction mixture following the completion of the reaction as described above at 410 nm in a spectrophotometer. The enzyme activity at each pH was reported as relative activity where the activity at the pH optimum was normalized to 100%.

The pH profile of Bhe Man2 is shown in FIG. 3. Bhe Man2 was found to have an optimum pH at about pH 8.0 to pH 9.0. The polypeptide was also found to retain greater than 70% of its maximum activity between pH 6.0 and pH 9.0.

Example 7

The Temperature Profile of Bhe Man2

The temperature optimum of purified Bhe Man2 polypeptide was determined by measuring the beta-mannanase of Bhe Man2 at various temperatures between 40° C. and 84° C., in a 50 mM sodium citrate buffer, pH 6.0, for 10 minutes. The activity was reported as relative activity where the activity at the temperature optimum was normalized to 100%. The temperature profile of Bhe Man2 is shown in FIG. 4.

Bhe Man2 was found to have an optimum temperature of 64° C., and was found to retain greater than 80% of maximum activity between 50° C. and 74° C.

Example 8

The Thermostability Profile of Bhe Man2

The thermostability of Bhe Man2 was determined in a 50 mM sodium citrate buffer, pH 6.0. The enzyme was incubated in a PCR thermal cycler at the desired temperature for 2 hours. The remaining or residual activity of each sample was measured as described in Example 5 above. The activity of a control Bhe Man2 sample kept on ice was used to define a 100%-retained activity. The thermostability profile of Bhe Man2 is shown in FIG. 5.

Bhe Man2 retained about 50% activity over a 2-hour incubation period at 75° C. At least 95% of the beta-mannanase activity was maintained after a 2-hour incubation period at temperatures lower than 55° C., indicating that Bhe Man2 was remarkably thermostable.

Example 9

Hydrolysis of an Alkaline KRAFT-Pretreated Softwood Biomass Substrate Using an Enzyme Composition Comprising Bhe Man2

An alkaline KRAFT-pretreated softwood substrate FPP-27 was obtained from Agence Nationale de la Recherche, France (ARN-05-BIOE-007) through a research project funded by L'Agence Nationale de l'Environmental et de la Maitrise de l'Energie (ADEME 0501 C0099), and a composition analysis was conducted, indicating the following content of the biomass: ~2.5 wt. % Klason lignin; ~81.4 wt. % glycan; ~7.9 wt. % xylan, ~0.8 wt. % galactan; and ~6.5 wt. % mannan. The substrate, in an amount of 1.93 g, at a dry solids loading level of 8.6% and total cellulose loading of 7% was mixed with an Accellerase® TRIO™ sample (which was pre-diluted into the desired concentration, as needed, using 0.05 M sodium citrate buffer, pH 5.0) at 10 mg/g glucan into a reaction mixture as a control. The substrate, in an amount of 1.93 g, at the same dry solids loading level of 8.6% and total cellulose loading of 7%, was mixed with a blended enzyme having 9 mg/g glucan of Accellerase® TRIO™ and 1 mg/g glucan of Bhe Man2, or 1 mg/g glucan of ScoMan1, or 1 mg/g glucan of Bsp Man1, or 1 mg/g glucan of Msp Man2, in a reaction mixture. The reaction mixtures and the control mixture were adjusted to pH 5 using a 0.1 M sodium citrate buffer. A 5% sodium azide was added to each of the reaction mixtures and control mixture to control microbial growth.

The reaction mixture and the control mixture are then incubated in a New Brunswick Scientific Innova 44 Incubator Shaker at 50° C., with gentle agitation at 200 rpm. After 24 hours, 48 hours, 72 hours, a small sample of about 200 µL was taken from each of the reaction mixture, diluted in 200 µL of MilliQ water, followed by filtration through a 0.2 µm filter. The filtrate was then injected into a Waters HPLC, equipped with a Waters 2695 Separation Module, set at a flow rate of 0.6 mL/min, and a mobile phase of MilliQ water degassed with 0.2 µm filter; a Phenomenex Rezex RCM 300×7.8 mm column, and in tandem, an RPM 300×7.8 mm column; a Phenomenex Security Guard Kit, including a Carbo-Ca 4×3.0 mm security guard cartridge; and a Waters 2414 Refractive Index Detector, set at an operating temperature of 50° C. The reaction mixtures as well as the control sample were analyzed for the amount of glucose, xylose and mannose. The results are presented in FIGS. 6A-6C.

The reaction mixtures were allowed to continue for as long as 72 hours, and the total carbohydrate conversion during the time period of 24-72 hours of each of the samples were plotted and presented as time courses in FIG. 7.

Example 10

Viscosity Reduction by Bhe Man2

An FPP-27 KRAFT-pretreated softwood pulp can be used, which has been determined via a composition analysis to contain the following: ~2.5 wt. % Klason lignin; ~81.4 wt. % glycan; ~7.9 wt. % xylan, ~0.8 wt. % galactan; and ~6.5 wt. % mannan. Alternatively the same SPORL-pretreated softwood substrate can be used, which has been determined by a composition analysis to contain the following: ~32.4 wt. % klason lignin; ~49.4 wt. % glucan; ~3.4 wt. % xylan; and ~4.6 wt. % mannan. As a control substrate, an acid-pretreated whole hydrolysate corn stover (whPCS) (see, e.g., website: nrel.gov/docs/fy11osti/47764.pdf), which does not contain any GGM or GM, but contains ~33.8 wt. % glucan, no xylan, and ~2.2 wt. % galactan, can be used.

An amount of 1.93 g of such a substrate (including, for example the FPP-27 substrate or the SPORL-pretreated softwood substrate, and the control whPCS substrate), at a dry solids loading level of 8.6% and a total glucan loading of 7.0%, can then be mixed with 10 mg/g glucan of Accellerase® TRIO™ as a control mixture, and with 1 mg/g glucan of Bhe Man2 plus 9 mg/g glucan of Accellerase® TRIO™ in a reaction mixture. The reaction mixture and the control mixture are then adjusted to pH 5.0 using a 0.1 M sodium citrate buffer, and incubation can take place with gentle agitation at a temperature of about 50° C., for at least 16 hours.

After at least 16 hours of incubation, the viscosity of each of the resulting mixtures (about 2-3 grams of sample) can be determined using the Rapid Visco Analyzer Super 4 Viscometer. (Newport Scientific). The Bhe Man2 polypeptide, when mixed with Accellerase® TRIO™ in the above-described proportions, impart a substantial viscosity reduction benefit, such as, for example, achieving at least a 20% reduced viscosity at the 16-hour incubation point.

Although the foregoing compositions and methods has been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the present compositions and methods. It will be appreciated that those skilled in the art will be able to devise various arrangements which, although not explicitly described or shown herein, embody the principles of the present compositions and methods and are included within its spirit and scope. Furthermore, all examples and conditional language recited herein are principally intended to aid the reader in understanding the principles of the present compositions and methods and the concepts contributed by the inventors to furthering the art, and are to be construed as being without limitation to such specifically recited examples and conditions. Moreover, all statements herein reciting principles, aspects, and embodiments of the present compositions and methods as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present compositions and methods, therefore, is not intended to be limited to the exemplary embodiments shown and described herein.

We claim:

1. A recombinant nucleic acid which comprises a nucleic acid encoding a recombinant polypeptide comprising the amino acid sequence of SEQ ID NO:2 or SEQ ID NO:3 and a heterologous nucleic acid, wherein the recombinant polypeptide has beta-mannanase activity, and wherein said nucleic acid encoding the recombinant polypeptide is operably linked to the heterologous nucleic acid.

2. The recombinant nucleic acid of claim 1, wherein the heterologous nucleic acid encodes a signal peptide sequence selected from any one of SEQ ID NOs:13-41.

3. A host cell comprising the recombinant nucleic acid of claim 1, wherein the host cell is a microorganism.

4. The host cell of claim 3 wherein the heterologous nucleic acid encodes a signal peptide sequence.

5. The host cell of claim 4 wherein the signal peptide sequence is selected from any one of SEQ ID NOs: 13-41.

6. The host cell of claim 3 wherein the host cell is a bacterial cell or a fungal cell.

7. The host cell of claim 3 wherein the host cell is *Trichoderma reesei*.

8. The recombinant nucleic acid of claim 1, wherein the recombinant polypeptide comprises the amino acid sequence of SEQ ID NO: 2.

9. The recombinant nucleic acid of claim 1, wherein the recombinant polypeptide comprises the amino acid sequence of SEQ ID NO: 3.

10. The host cell of claim 3, wherein the recombinant polypeptide comprises the amino acid sequence of SEQ ID NO: 2.

11. The host cell of claim 3, wherein the recombinant polypeptide comprises the amino acid sequence of SEQ ID NO: 3.

* * * * *